US010105321B2

(12) United States Patent
Tygesen et al.

(10) Patent No.: US 10,105,321 B2
(45) Date of Patent: *Oct. 23, 2018

(54) PHARMACEUTICAL COMPOSITIONS RESISTANT TO ABUSE

(71) Applicant: Egalet Ltd., London (GB)

(72) Inventors: Peter Holm Tygesen, Smoerum (DK); Jan Martin Oevergaard, Frederikssund (DK); Karsten Lindhardt, Haslev (DK); Louise Inoka Lyhne-Iversen, Gentofte (DK); Martin Rex Olsen, Holbaek (DK); Anne-Mette Haahr, Birkeroed (DK); Jacob Aas Hoeilund-Jensen, Frederikssund (DK); Pernille Kristine Hoeyrup Hemmingsen, Bagsvaerd (DK)

(73) Assignee: EGALET LTD., London (GB)

( * ) Notice: Subject to any disclaimer, the term of this patent is extended or adjusted under 35 U.S.C. 154(b) by 28 days.

This patent is subject to a terminal disclaimer.

(21) Appl. No.: 15/293,867

(22) Filed: Oct. 14, 2016

(65) Prior Publication Data

US 2017/0100341 A1    Apr. 13, 2017

Related U.S. Application Data

(63) Continuation of application No. 14/859,800, filed on Sep. 21, 2015, now Pat. No. 9,498,446, which is a continuation of application No. 14/062,719, filed on Oct. 24, 2013, now Pat. No. 9,168,228, which is a continuation of application No. 12/701,429, filed on Feb. 5, 2010, now Pat. No. 8,603,526.

(60) Provisional application No. 61/150,620, filed on Feb. 6, 2009.

(30) Foreign Application Priority Data

Feb. 6, 2009 (DK) .................. 2009 00192

(51) Int. Cl.
| | |
|---|---|
| A61K 9/28 | (2006.01) |
| A61K 31/485 | (2006.01) |
| A61K 31/407 | (2006.01) |
| A61K 31/137 | (2006.01) |
| A61K 31/4458 | (2006.01) |
| A61K 31/5513 | (2006.01) |
| A61K 9/48 | (2006.01) |
| A61K 9/20 | (2006.01) |

(52) U.S. Cl.
CPC ............ *A61K 9/2853* (2013.01); *A61K 9/205* (2013.01); *A61K 9/2013* (2013.01); *A61K 9/2018* (2013.01); *A61K 9/2031* (2013.01); *A61K 9/2054* (2013.01); *A61K 9/2072* (2013.01); *A61K 9/288* (2013.01); *A61K 9/2866* (2013.01); *A61K 9/2893* (2013.01); *A61K 9/4808* (2013.01); *A61K 9/4816* (2013.01); *A61K 9/4833* (2013.01); *A61K 31/137* (2013.01); *A61K 31/407* (2013.01); *A61K 31/4458* (2013.01); *A61K 31/485* (2013.01); *A61K 31/5513* (2013.01)

(58) Field of Classification Search
None
See application file for complete search history.

(56) References Cited

U.S. PATENT DOCUMENTS

| | | | |
|---|---|---|---|
| 2,685,553 | A | 8/1954 | Carroll et al. |
| 4,034,758 | A | 7/1977 | Theeuwes |
| 4,449,983 | A | 5/1984 | Cortese et al. |
| 4,898,733 | A | 2/1990 | DePrince et al. |
| 5,019,396 | A | 5/1991 | Ayer et al. |
| 5,213,808 | A | 5/1993 | Bar Shalom et al. |
| 5,609,885 | A | 3/1997 | Rivera et al. |
| 5,869,097 | A | 2/1999 | Wong et al. |
| 6,103,261 | A | 8/2000 | Chasin et al. |
| 8,603,526 | B2 | 12/2013 | Tygesen et al. |
| 9,168,228 | B2 | 10/2015 | Tygesen et al. |
| 9,358,295 | B2 | 6/2016 | Tygesen et al. |
| 9,498,446 | B2 | 11/2016 | Tygesen et al. |
| 2003/0118641 | A1 | 6/2003 | Maloney et al. |
| 2003/0133976 | A1 | 7/2003 | Pather et al. |
| 2004/0151772 | A1 | 8/2004 | Andersen et al. |
| 2005/0053655 | A1 | 3/2005 | Yang et al. |
| 2005/0158382 | A1 | 7/2005 | Cruz et al. |
| 2006/0193912 | A1 | 8/2006 | Ketsela et al. |
| 2007/0003617 | A1 | 1/2007 | Fischer et al. |
| 2007/0004797 | A1 | 1/2007 | Weyers et al. |
| 2007/0190142 | A1 | 8/2007 | Breitenbach et al. |
| 2007/0224129 | A1 | 9/2007 | Guimberteau et al. |
| 2007/0264346 | A1 | 11/2007 | Guimberteau et al. |
| 2008/0152595 | A1 | 6/2008 | Emigh et al. |
| 2008/0166407 | A1 | 7/2008 | Shalaby et al. |
| 2008/0299199 | A1 | 12/2008 | Bar Shalom et al. |

(Continued)

FOREIGN PATENT DOCUMENTS

| | | |
|---|---|---|
| EP | 0435726 | 8/1991 |
| EP | 0493513 | 7/1992 |

(Continued)

OTHER PUBLICATIONS

International Search Report and the Written Opinion of the International Searching Authority dated Jul. 8, 2008 in International Application No. PCT/DK2008/000016.

(Continued)

*Primary Examiner* — Tigabu Kassa

(74) *Attorney, Agent, or Firm* — Foley & Lardner LLP

(57) ABSTRACT

The present invention provides immediate release pharmaceutical compositions for oral administration that are resistant to abuse.

27 Claims, 23 Drawing Sheets

(56) References Cited

U.S. PATENT DOCUMENTS

| | | | |
|---|---|---|---|
| 2008/0311205 | A1 | 12/2008 | Habib et al. |
| 2009/0022790 | A1 | 1/2009 | Flath et al. |
| 2009/0202634 | A1 | 8/2009 | Jans et al. |
| 2009/0221621 | A1 | 9/2009 | Sathyan et al. |
| 2010/0203129 | A1 | 8/2010 | Andersen et al. |
| 2010/0203130 | A1 | 8/2010 | Tygesen et al. |
| 2010/0204259 | A1 | 8/2010 | Tygesen et al. |
| 2010/0239667 | A1 | 9/2010 | Hemmingsen et al. |
| 2010/0291205 | A1 | 11/2010 | Downie et al. |
| 2011/0159100 | A1 | 6/2011 | Andersen et al. |

FOREIGN PATENT DOCUMENTS

| | | |
|---|---|---|
| EP | 0406315 | 11/1992 |
| EP | 1213014 | 6/2002 |
| WO | WO 1989/009066 | 10/1989 |
| WO | WO 1991/004015 | 4/1991 |
| WO | WO 1995/022962 | 8/1995 |
| WO | WO 1999/051208 | 10/1999 |
| WO | WO 2000/041704 | 7/2000 |
| WO | WO 2003/026613 | 4/2003 |
| WO | WO 2003/075897 | 9/2003 |
| WO | WO 2003/082204 | 10/2003 |
| WO | WO 2004/093819 | 11/2004 |
| WO | WO 2004/093843 | 11/2004 |
| WO | WO 2005/016313 | 2/2005 |
| WO | WO 2006/026504 | 3/2006 |
| WO | WO 2006/058249 | 6/2006 |
| WO | WO 2006/106344 | 10/2006 |
| WO | WO 2007/131357 | 11/2007 |
| WO | WO 2008/023261 | 2/2008 |
| WO | WO 2010/032128 | 3/2010 |

OTHER PUBLICATIONS

International Search Report and the Written Opinion of the International Searching Authority dated Apr. 21, 2010 in International Application No. PCT/EP2010/000728.
International Search Report and the Written Opinion of the International Searching Authority dated May 28, 2010 in International Application No. PCT/DK2010/000019.
International Search Report and the Written Opinion of the International Searching Authority dated Jan. 28, 2009 in International Application No. PCT/US2008/056910.
International Search Report and the Written Opinion of the International Searching Authority dated Feb. 6, 2010 in International Application No. PCT/DK2010/050016.
International Type Search Report dated Jun. 17, 2009 in International Application No. DK 2009001925.
Office Action dated Oct. 17, 2012 in co-pending U.S. Appl. No. 12/701,429.
Notice of Allowance dated Jul. 24, 2013 in in co-pending U.S Appl. No. 12/701,429.
First Office Action dated Feb. 24, 2012 in co-pending U.S Appl. No. 12/701,248.
Second Office Action dated Jul. 20, 2012 in co-pending U.S Appl. No. 12/701,248.
Office Action dated Oct. 26, 2011 in U.S Appl. No. 12/523,045, now US 2010/0291205.
Office Action dated May 24, 2012 in U.S Appl. No. 12/523,045, now US 2010/0291205.
First Office Action dated Mar. 7, 2013 in co-pending U.S Appl. No. 12/602,953.
First Office Action dated Apr. 11, 2012 in co-pending U.S Appl. No. 12/694,197.
Final Office Action dated Sep. 14, 2012 in co-pending U.S Appl. No. 12/694,197.
First Office Action dated Nov. 14, 2011 in U.S Appl. No. 12/823,067.
Final Office Action dated Sep. 10, 2012 in U.S Appl. No. 12/823,067.
Notice of Allowance dated Jun. 11, 2013 in U.S Appl. No. 12/823,067.
Office Action dated Jan. 8, 2016 in U.S Appl. No. 12/523,045.
Office Action dated Jun. 22, 2016 in U.S Appl. No. 14/560,579.
Office Action dated Jan. 12, 2016 in U.S Appl. No. 14/560,579.
Notice of Allowance dated Feb. 9, 2016 in U.S Appl. No. 14/656,016 (U.S. Pat. No. 9,358,295).
Notice of Allowance dated Feb. 12, 2016 in U.S Appl. No. 14/496,561 (US 2015/0079150).
Office Action dated Feb. 22, 2016 in U.S Appl. No. 13/974,689 (US 2014/0120164).
Office Action dated Mar. 11, 2016 in U.S Appl. No. 14/446,234 (US 2015/0024048).
Notice of Allowance dated Jul. 15, 2016 in U.S Appl. No. 14/859,800 (U.S. Pat. No. 9,498,446).
Office Action dated Jun. 23, 2016 in U.S Appl. No. 13/933,052 (US 2014/0010873).
Notice of Allowance dated Dec. 2, 2016 in U.S Appl. No. 13/933,052 (US 2014/0010873).
Office Action dated Jul. 11, 2016 in U.S Appl. No. 12/523,045 (US 2010/0291205).
Office Action dated Jul. 22, 2016 in U.S Appl. No. 14/331,833 (US 2015/0037417).
Office Action dated Jul. 25, 2016 in U.S Appl. No. 13/974,689 (US 2014/0120164).
Office Action dated Aug. 9, 2016 in U.S Appl. No. 14/446,234 (US 2015/0024048).
Camu & Vanlersberghe, "Pharmacology of Systemic Analgesics." Best Practice and Research Clinical Anesthesiology, 2002; 16(4): 475-88.
Dahlstrom, et al., "Patient-Controlled Analgesic Therapy, Part IV: Pharmacokinetics and Analgesic Plasma Concentrations of Morphine." Clinical Pharmacokinetics, 1982; 7:266-79.
Fischer, et al., "Nonmedical Use of Prescription Opioids: Furthering a Meaningful Research Agenda," J. Pain. 9:6, Jun. 2008 490-493.
Graves et al., "Relationship Between Plasma Morphine Concentrations and pharmacologic Effects in Postoperative Patients Using Patient-Controlled Analgesia." Clinical Pharmacology, 1985; 4:41-7.
Haahr, et al. (Poster—Drug Abuse Resistant, Controlled Release using Egalet Dosage Units. Proceedings of the 34th Annual Meeting Exposition of the Controlled Release Society Jul. 7-11, 2007).
Hemmingsen, et al., "Drug Abuse Resistant, Controlled Release, Using Egalet Dosage Units" poster. Published Jun. 28, 2007.
Katikaneni, et al. Ethylcellulose Matrix controlled Release Tablets of a Water-Soluable Drug. International Journal of Pharmaceutics 123 pp. 119-125 1995.
L. Qui, et al., "Design Core-Shelled Polymer Cylinder for Potential Programmable Drug Delivery." Int. J. Pharm., 2001; 219:151-160.
Meyer, et al., "Awareness Topic: Mitigating the Risks of Ethanol Induced Dose Dumping from Oral Sustained/Controlled Release Dosage Forms," FDA's ACPS Meeting, Oct. 2005.
National Institute on Drug Abuse, Monitoring the Future, "National Results on Adolescent Drug Use—Overview of Key Findings 2009," http://www.monitoringthefuture.org/ (Originally Published in May 2010).
National Institute on Drug Abuse, Monitoring the Future, "National Results on Adolescent Drug Use—Overview of Key Findings 2008," http://www.samhsa.gov/ (Originally Published in May 2009).
National Institute on Drug Abuse, 2008 http://www.nida.nih.gov/drugpages/prescription.html (Last Accessed on Jul. 15, 2008).
Raehhal & Bohn, "Mu Opioid Receptor Regulation and Opiate Responsiveness." The AAPS Journal 2005; 7(3): Article 60.
(www.rxlist.com/miralax-drug.htm) as referenced Oct. 19, 2011.
Roberts, et al. "Enterohepatic Circulation: Physiological, Pharmacokinetic and Clinical Implications." Clin. Pharmacokinet., vol. 41, Issue 10, pp. 751-790, (2002).

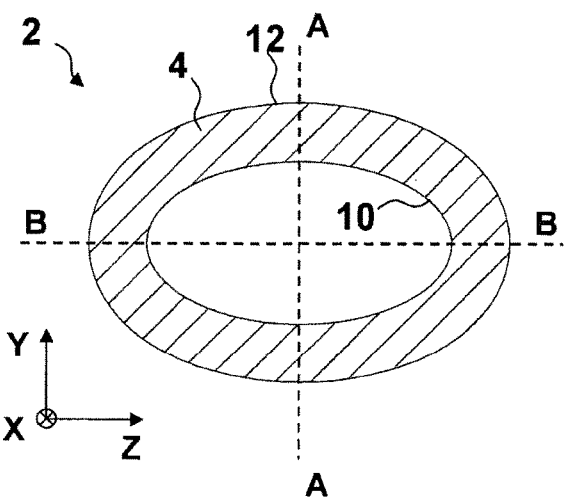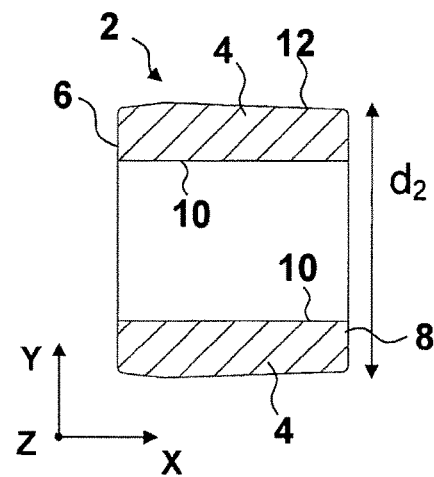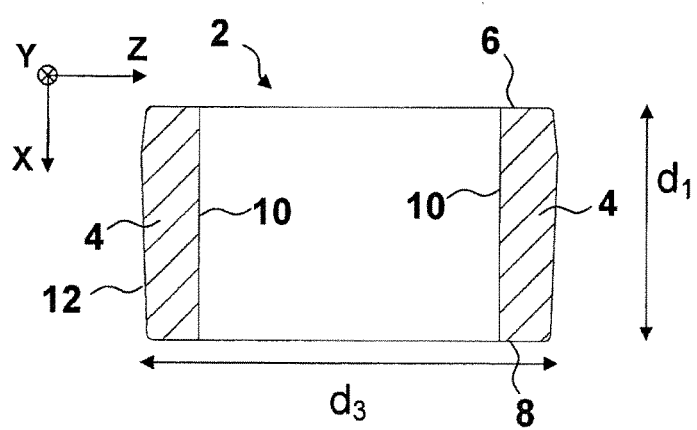

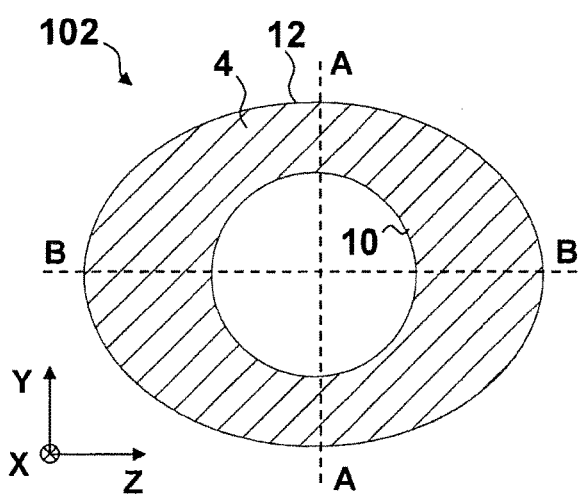
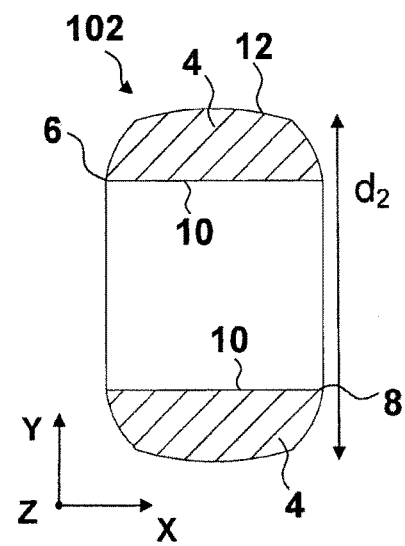
Fig. 2A    Fig. 2B
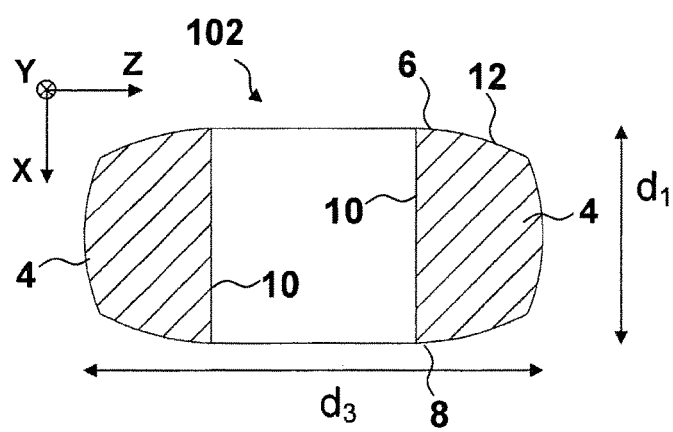
Fig. 2C

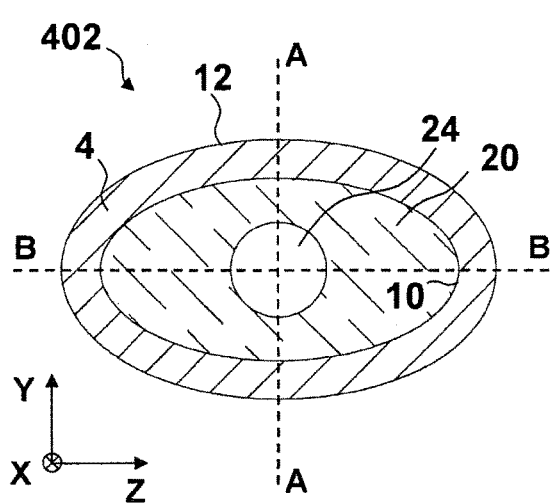
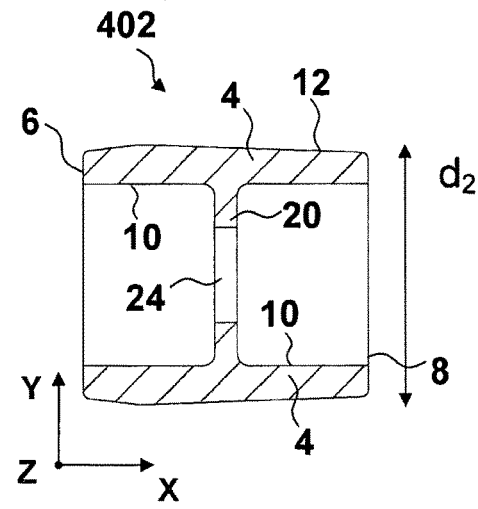
Fig. 5A     Fig. 5B
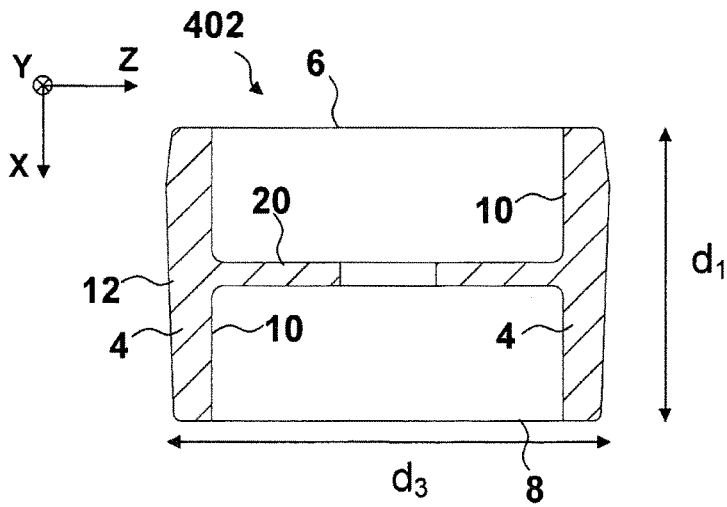
Fig. 5C

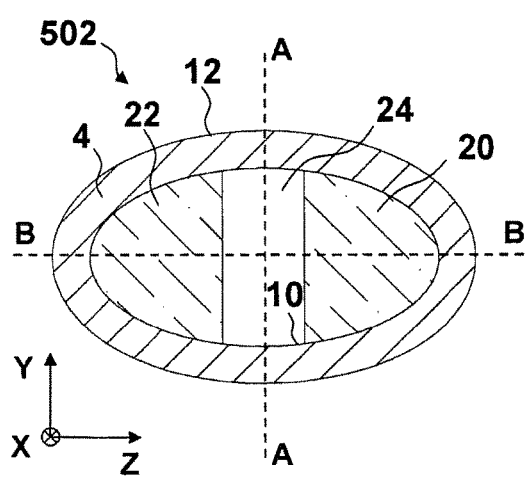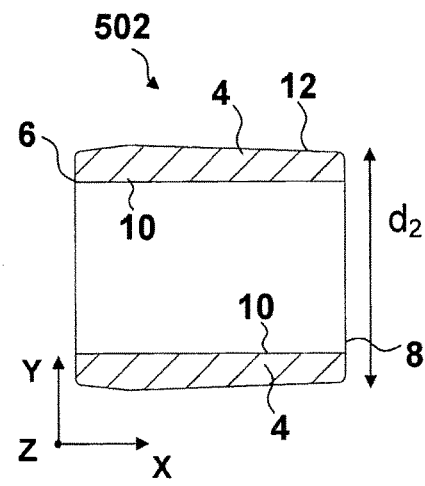
Fig. 6A          Fig. 6B
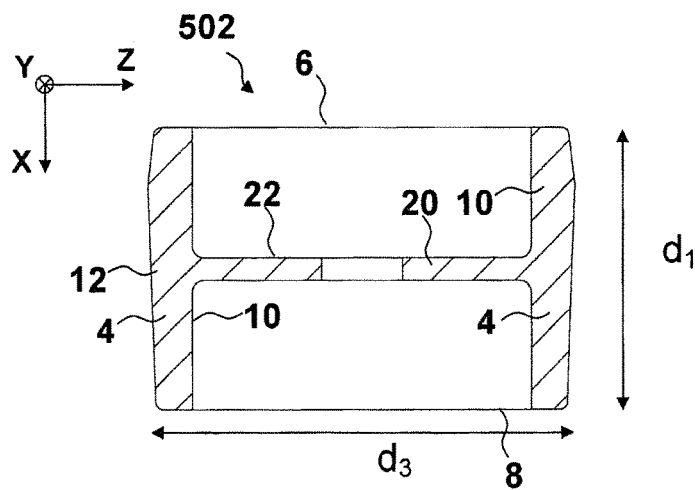
Fig. 6C

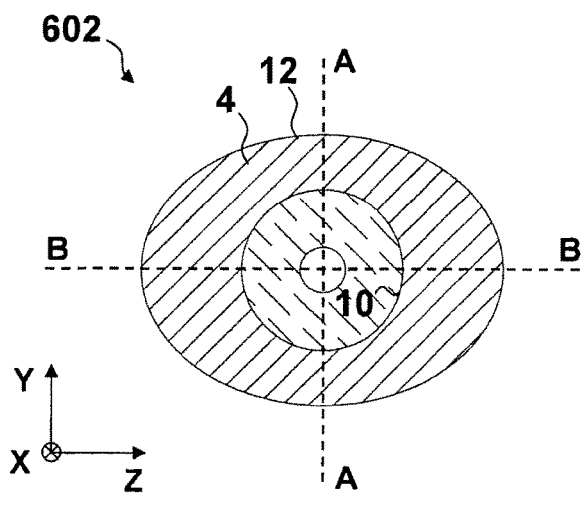
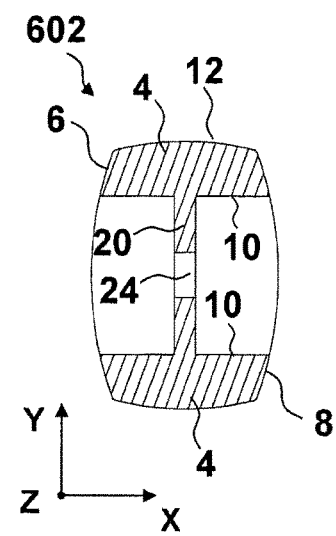
Fig. 7A   Fig. 7B
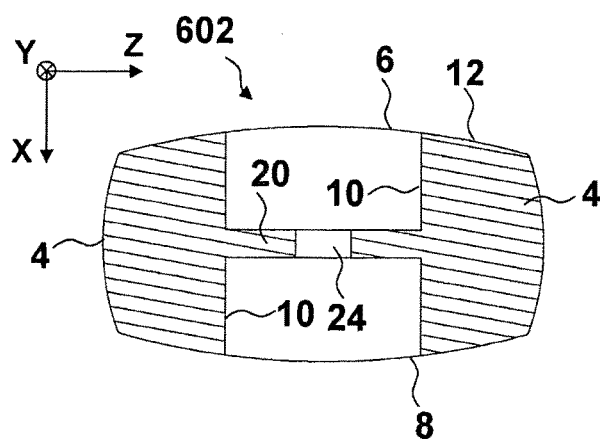
Fig. 7C

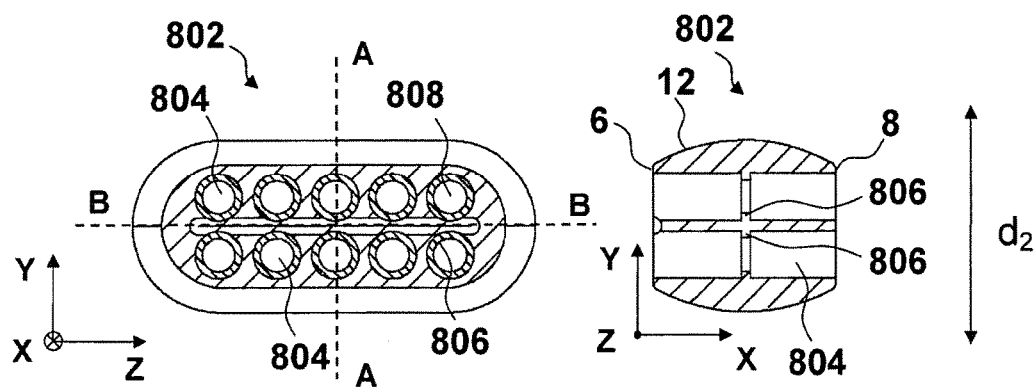
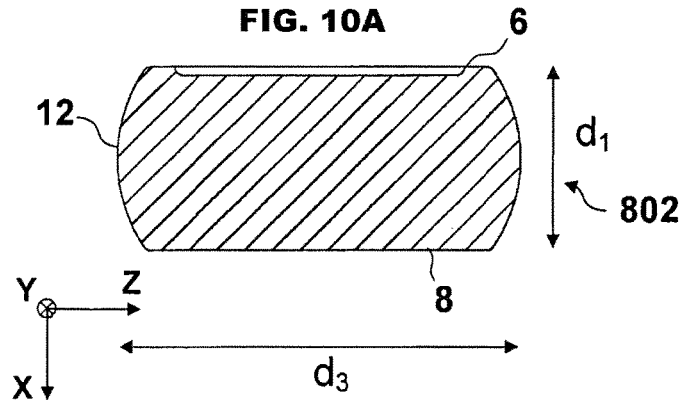
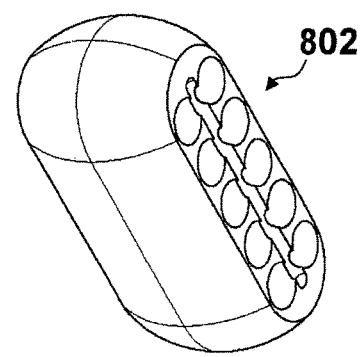
FIG. 10A
FIG. 10B
FIG. 10C
FIG. 10D

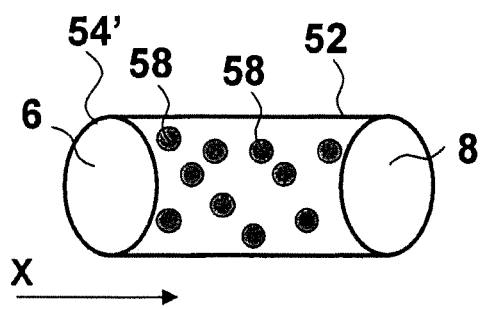
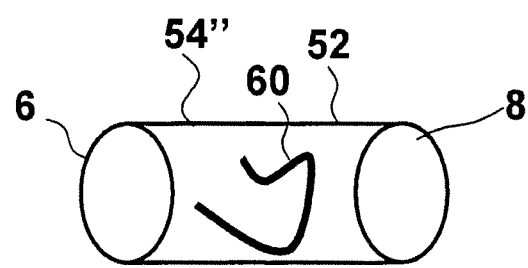
FIG. 13A  FIG. 13B
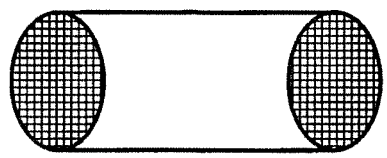
FIG. 13C

PHARMACEUTICAL COMPOSITIONS RESISTANT TO ABUSE

This application is a continuation of U.S. application Ser. No. 14/859,800, filed Sep. 21, 2015, now U.S. Pat. No. 9,498,446, which is a continuation of U.S. application Ser. No. 14/062,719, filed Oct. 24, 2013, now U.S. Pat. No. 9,168,228, which is a continuation of U.S. application Ser. No. 12/701,429, filed Feb. 5, 2010, now U.S. Pat. No. 8,603,526, which claims the benefit of priority of U.S. Provisional Application No. 61/150,620, filed Feb. 6, 2009, and Denmark Patent Application No. PA 2009 00192, filed Feb. 6, 2009.

All patent and non-patent references cited in the application are hereby incorporated by reference in their entirety.

FIELD OF THE INVENTION

The present invention relates to pharmaceutical compositions. In particular embodiments, pharmaceutical compositions in the form of unit dosage forms that are resistant to abuse are provided.

BACKGROUND

In recent years, increased attention has been drawn to the abuse of prescription drugs. The abuse, or non-medicinal use, of prescription medicines has been reported to be an increasing problem particularly in North America. This phenomenon has become an increasing epidemiological, public health and political concern (See, for example, Fischer and Rehm, J. Pain 9:6, 2008 490-493). In 2006, it was reported that 16.2 million Americans age 12 and older had taken a prescription pain reliever, tranquilizer, stimulant, or sedative for nonmedical purposes at least once in the year prior to being surveyed (National Survey on Drug Use and Health; http://www.samhsa.gov/). In another study, it reported that approximately 5.2% of $12^{th}$ graders abused OxyContin® for nonmedical purposes at least once in the year prior to being surveyed (Monitoring the Future http://www.monitoringthefuture.org/).

Methods for abusing prescription drugs are varied and include, for example, single or multiple step extraction, physical tampering followed by crushing, extraction, melting, volatilization or direct administration. For purposes of abuse, methods of administering drug substances obtained from prescription drug products or of the drug products themselves are similarly diverse and include, for example, injection, smoking, swallowing, sublingual or buccal administration, chewing, and administration as suppository (See, e.g., National Institute of Drug Abuse, 2008). Prescription drug products that typically misused primarily fall into three groups: 1) Opioids prescribed for pain; 2) CNS depressants prescribed for anxiety of sleep problems; and 3) Stimulants, prescribed, for example, for attention deficit hyperactivity, narcolepsy or obesity. In the context of controlled release opioid products, chewing of the drug product to break up and provide rapid release of a relatively large dose of the opioid drug substance is one of the most commonly used methods of abuse.

Because the potential for abuse of prescription drug products has become an important issue for the U.S. Food and Drug Administration (FDA), the pharmaceutical industry is striving to develop abuse resistant formulations in order to reduce the potential for misuse of prescription drugs. Examples of two abuse resistant drug products submitted to the FDA for approval include Remoxy™ and Embeda™. The Remoxy™ product is formulated to be an abuse resistant product for the delivery of oxycodone, while the Embeda™ product is formulated to be an abuse resistant product for the delivery of morphine. The Embeda™ product was approved by the FDA the on the $14^{th}$ of October, 2009.

Alcohol-induced dose dumping of drug substance from prescription drug products also presents potential abuse and safety problems. For purposes of the present disclosure, "dose dumping" refers to an unintended, rapid release of the entire amount or a significant fraction of the drug substance contained within a prescription drug product over a short or accelerated period of time. For purposes of abuse, alcohol-induced dose dumping may facilitate isolation or concentration of drug substances from a prescription drug product. Alternatively, dose dumping in the presence of alcohol may increase the ease with which a prescription drug product simply through the intake of an alcoholic beverage concomitantly with the prescription drug product. Moreover, alcohol-induced dose dumping may present safety issues outside the context of abuse. For example, a patient taking a prescription drug product for medicinal purposes may inadvertently cause delivery of a dose of drug substance that is too high or absorbed too quickly by self administering a drug product shortly before, simultaneously with or shortly after intake of an alcoholic beverage or another medicinal product containing alcohol (such as an over the counter cold or flu medicine). It has been reported that some modified-release oral dosage forms contain active drug substances and excipients that exhibit higher solubility in alcoholic solutions compared to water. Such products may exhibit a more rapid drug dissolution and release rate in the presence of ethanol.

SUMMARY

Pharmaceutical compositions resistant to abuse and methods of making and using such compositions are described herein. The pharmaceutical compositions described herein include an outer shell and a drug composition containing one or more active drug substances. The drug composition included in the pharmaceutical compositions described herein may be a matrix composition, and the terms "drug composition" and "matrix composition" are used interchangeably herein. Configurations, materials, and methods for producing abuse resistant pharmaceutical compositions having an outer shell positioned over a drug composition are detailed herein. In certain embodiments, the pharmaceutical compositions are provided as unit dosage forms suitable for oral administration.

The shell included in the pharmaceutical compositions described herein can be formulated to resist physical tampering, such as by chewing, crushing, chipping, grinding, or other applications of mechanical force that may compromise the physical integrity of the of the composition or result in particle size reduction. In certain embodiments, the shell included in the pharmaceutical compositions described herein is formulated to exhibit a hardness that resists physical tampering. In other embodiments, the shell is configured to resist physical tampering, such as by inclusion of one or more reinforcement elements. In still other embodiments, the shell is formulated and/or configured to maintain adherence between the shell and the drug composition, such that deformation and separation of the drug composition from the shell is made more difficult. Of course, it will be understood that the shell included in the pharmaceutical compositions described herein may incorporate each of the features of the embodiments described herein. The shell included in the pharmaceutical compositions described herein, therefore, can be formulated and configured to resist chewing, crushing, chipping, grinding and other methods that may otherwise result in particle size reduction of the pharmaceutical composition and, thereby, provides a pharmaceutical composition that is resistant to abuse.

The drug composition included in the pharmaceutical compositions described herein may be formulated to resist abuse. For example, the drug composition may be formulated in such a way that the composition maintains a desired release profile of drug substance even if the pharmaceutical composition is subjected to physical tampering. In some embodiments, the drug composition may incorporate a gelling agent, which can render the pharmaceutical composition unfit for injection if attempts are made to introduce the composition into a liquid solution. In addition, or alternatively, the drug composition included in the pharmaceutical compositions described herein may include an antagonist to the drug substance to be delivered by the pharmaceutical composition. In such an embodiment, the drug composition is formulated such that the antagonist is only released when the pharmaceutical composition is subjected to physical and/or chemical tampering.

An exemplary mastication test and an exemplary particle size reduction test are disclosed herein. Such tests may be used to evaluate a given pharmaceutical composition's resistance to physical tampering.

BRIEF DESCRIPTION OF THE DRAWINGS

FIGS. 1A-1C schematically illustrate an exemplary shell according to the present invention.

FIGS. 2A-2C schematically illustrate an exemplary shell according to the present invention.

FIGS. 5A-5C schematically illustrate an exemplary shell according to the present invention.

FIGS. 6A-6C schematically illustrate an exemplary shell according to the present invention.

FIGS. 7A-7C schematically illustrate an exemplary shell according to the present invention.

FIGS. 10A-10D schematically illustrate an exemplary shell according to the present invention.

FIGS. 11-13A-13C illustrate examples of pharmaceutical compositions.

DETAILED DESCRIPTION

Figures 3A, 3B:
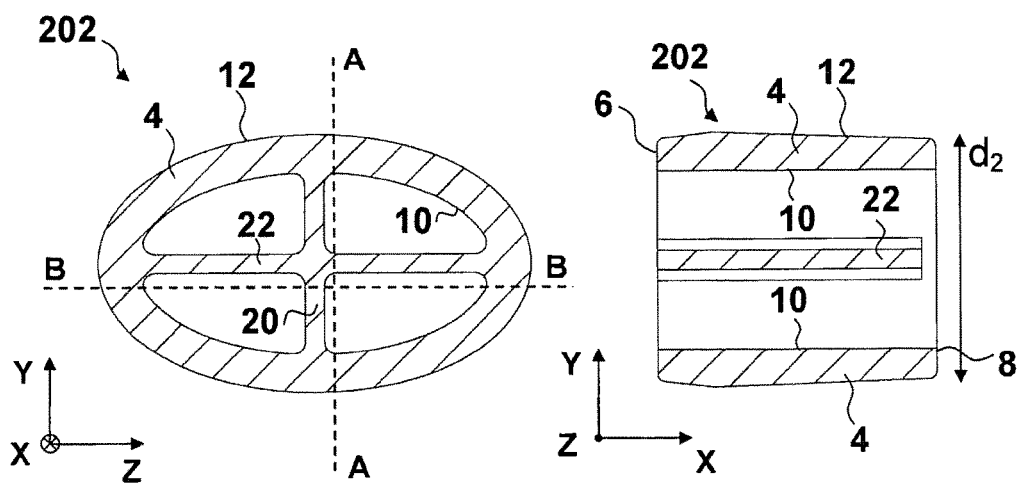
FIGS. 3A-3C schematically illustrate an exemplary shell according to the present invention.

The pharmaceutical compositions described herein include a shell and a drug composition. Exemplary materials, configurations and methods for providing pharmaceutical compositions that are resistant to abuse are provided herein. In the following description the pharmaceutical compostions are described in relation to a conventional three dimensional Cartesian coordinate system with first axis X, second axis Y and third axis Z.

Shell Construction

As it appears from the examples and figures herein, the pharmaceutical compositions described herein include a shell that exhibit a structural strength that results in a composition, such as a unit dosage form suitable for oral administration, that is resistant to physical tampering, such as by chewing, crushing, chipping, grinding, or other applications of mechanical force that may compromise the physical integrity of the of the composition or result in particle size reduction. The shell included in the pharmaceutical compositions described herein forms an outer shell wall (or "shell wall") that includes inner and outer surfaces and defines a cavity generally defined by the inner surface of the shell wall. In particular embodiments, the shell included in the pharmaceutical compositions described herein exhibits a thickness that provides a shell resistant to physical tampering. In certain such embodiments, the shell is configured to include one or more reinforcement elements, such as one or more ribs, enforcement walls, protrusions or the like, extending into or within the cavity defined by the shell wall.

The drug composition included in the pharmaceutical compositions described herein is disposed within the cavity formed by the shell wall and the inner surface of the shell wall is in contact with at least a portion of the drug composition. In specific embodiments, the outer shell wall of the shell extends from a first end to a second end along a first axis. In one such embodiment, one or more openings may be provided in the shell wall at each end or at one end of the shell enabling controlled release of a matrix composition accommodated within in the shell.

Typically, the shell wall will have a thickness in a range of from 1 mm to about 10 mm. In specific embodiments, the shell wall may have a maximum thickness selected from at least 1.0 mm, at least 1.3 mm, and at least 3.0 mm. In other embodiments, the shell wall has a maximum thickness selected from a range of from 1.0 mm to about 10 mm, and a range of from 1.0 mm to about 7 mm. In yet further embodiments, the shell wall has a maximum thickness selected from about 1.3 mm, 2.0 mm, 3.0 mm, 4.0 mm, 5.0 mm, and 6.0 mm, including or any ranges of thickness therebetween.

Whenever an amount is recited herein, it is understood that the amount may also be recited with terms of approximation such as "about" or "approximately." For example, a disclosure regarding a definite numerical amount such as "an amount of 1 unit" can also be substituted by an approximate amount such as "about 1 unit." As another example, a disclosure regarding a numerical range that is recited with definite endpoints such as "an amount ranging from 1 unit to 2 units" can also be substituted by a range with approximate endpoints such as "an amount ranging from about 1 unit to about 2 units." It is also understood that the use of the term "about" may be used to account for variations due to experimental errors.

In still another embodiment, the outer shell wall may have a maximum thickness of at least 1.7 mm, such as at least 2 mm. In certain such embodiments, the outer shell wall has a maximum thickness in the range from 2.0 mm to about 4 mm, such as thickness of about 2.4 mm.

The thickness of the outer shell wall may be substantially uniform across the length of the wall, or, alternatively, in specific embodiments, the thickness of the shell wall may vary. In particular, where outer shell wall of the shell is configured to extend from a first end to a second end along a first axis, the thickness of the outer shell wall may vary along the first axis. Moreover, in particular embodiments, the outer surface of the shell may curve along the first axis, providing an outer surface of the shell wall that is a double curved surface.

In specific embodiments where outer shell wall of the shell is configured to extend from a first end to a second end along a first axis, the height of the shell varies along the first axis. The height of the shell may vary between a minimum height and a maximum height. The minimum height of the shell may range from, for example, about 2.0 mm to about 20 mm, and in one particular embodiment, the minimum height may be about 4 mm. The maximum height of the shell may range from about 3 mm to about 30 mm, such as in the range from about 4 mm to about 20 mm, such as about 6 mm, about 8 mm, about 10 mm, about 12 mm, about 14 mm or about 16 mm.

In specific embodiments where outer shell wall of the shell is configured to extend from a first end to a second end along a first axis, the width of the shell varies along the first axis. The width of the shell may vary between a minimum width and a maximum width. The minimum width of the shell may range, for example, from about 2.0 mm to about 20 mm, and in one particular embodiment, the minimum height may be about 4 mm. The maximum width of the shell may range from about 3 mm to about 30 mm, such as in the range from about 4 mm to about 20 mm, such as about 6 mm, about 8 mm, about 10 mm, about 12 mm, about 14 mm or about 16 mm.

In specific embodiments where the shell wall is configured to extend from a first end to a second end along a first axis, the thickness of the outer shell wall varies along the first axis, e.g. from about 1.1 mm to about 2.4 mm. In one or more embodiments, e.g. shells having a circular cylindrical cavity and an elliptical outer surface cross section perpendicular to the first axis, the thickness of the outer shell wall varies about the first axis.

The thickness of the outer shell wall may vary along the first axis, e.g. from 0.7 mm to 1.9 mm. The outer shell wall may have a minimum thickness of at least 0.3 mm, such as at least 0.5 mm. The outer shell wall may have a minimum thickness of at least 0.7 mm, such as in the range from 1.0 mm to 3.0 mm.

In specific embodiments where the shell wall is configured to extend from a first end to a second end along a first axis, the outer surface of the outer shell wall may define a double curved surface, resulting in a curve in a plane perpendicular to the first axis and curve in a plane parallel to the first axis.

In specific embodiments where the shell wall is configured to extend from a first end to a second end along a first axis, the outer surface of the outer shell wall may be configured to have a cross-section perpendicular to the first axis that is selected from one of various different suitable forms. For example, the cross-section of the shell wall may be configured to exhibit a cross-section perpendicular to the first axis, wherein the cross section is selected from a circular, elliptic, oval, or polygonal shape. Moreover, such a cross sectional shape may be configured to optionally include rounded corners or sections or to exhibit a super-elliptic configuration. In particular embodiments, the shell wall may be configured such that cross-sections of the shell wall taken perpendicular to the first axis vary in size and/or shape along the first axis, as such a configuration can to facilitate oral administration as well as production by an injection molding.

In one or more embodiments where the shell wall is configured to extend from a first end to a second end along a first axis, a cross-section of the outer shell surface parallel to the first axis is a curve. In such embodiments, the outer surface of the shell forms may form an arc, such as a circular arc, an elliptical arc, a super-elliptical arc, etc.

In one or more embodiments where the shell wall is configured to extend from a first end to a second end along a first axis X, a cross-section of the outer surface of the shell taken perpendicular to the second axis Y may be a curve. In such embodiments, the outer surface of the shell forms may form an arc, such as a circular arc, an elliptical arc, a super-elliptical arc, etc.

In one or more embodiments where the shell wall is configured to extend from a first end to a second end along a first axis, a cross-section of the outer shell surface perpendicular to the third axis may be a curve. In such embodiments, the outer surface of the shell forms, may form an arc, such as a circular arc, an elliptical arc, a super-elliptical arc, etc.

A circular arc is defined as a part of the circumference of a circle having radius r. The radius r may be given as $r=\alpha$ times $d_1$, where $d_1$ is the length of the shell and $\alpha$ is in the range from 0.5 to about 6, such as in the range from about 0.7 to about 3, such as in the range from about 0.8 to about 2. In one or more embodiments, the shell is configured to exhibit an $\alpha=1$.

As described herein, the inner surface of the shell wall defines a cavity. In specific embodiments, the cavity defined by the shell wall is a cylindrical cavity, extending from a first end of the shell to a second end of the shell. In some embodiments, the shell may define a plurality of cavities extending from a first end to a second end of the shell. In one or more embodiments where outer shell wall is configured to extend from a first end to a second end along a first axis, the cylindrical cavity or cavities described herein may be configured to have a cross-section perpendicular to the first axis selected from, for example, circular, oval, elliptic, super-elliptic, or polygonal cross-sections. Accordingly, a pharmaceutical composition according to the present description may include a shell that defines one or more cylindrical cavities configured as an elliptic cylinder, a parabolic cylinder, a hyperbolic cylinder or a prism. A prism within the present context refers to a cylinder having a polygonal cross-section.

In one or more embodiments where the shell wall is configured to extend from a first end to a second end along a first axis, the inner surface of the shell may define a cylindrical cavity having an elliptical cross-section perpendicular to the first axis. In such embodiments, the ellipse formed by the inner shell surface may have semimajor axis $a_{in}$ parallel to the third axis and semiminor axis $b_{in}$ parallel to the second axis. The semimajor axis $a_{in}$ of an elliptical cross-section of a cylindrical cavity of a shell (to be filled with matrix composition) may range from about 0.5 mm to about 10 mm, such as in the range from 0.7 mm to about 9 mm, such as in the range from about 2.0 mm to about 8 mm. The semiminor axis $b_{in}$ of an elliptical cross-section of a cylindrical cavity of a shell (to be filled with matrix composition) may range from about 0.5 mm to about 10 mm, such as in the range from 0.7 mm to about 9 mm, or in the range from about 1.0 mm to about 8 mm. In certain embodiments, a semiminor axis $b_{in}$ in the range from about 1.0 mm to about 2.5 mm is provided.

In one or more embodiments, where the shell wall is configured to extend from a first end to a second end along a first axis, the inner surface of the outer shell wall may define a cylindrical cavity having a circular cross-section perpendicular to the first axis. In such an embodiment, the diameter of a circular cross-section of a cylindrical cavity of a shell (to be filled with matrix composition) may range from about 0.5 mm to about 20 mm, such as in the range from 1 mm to about 16 mm.

The shell has an outer surface that may be formed to facilitate oral administration, such as by swallowing of a pharmaceutical composition. The shell provided in the pharmaceutical compositions described herein, therefore, can be configured to have outer dimensions suitable for oral administration. The shell may have a length (maximum extension along the first axis) in the range from about 2 mm to about 30 mm, such as in the range from about 4 mm to about 20 mm, such as about 6 mm, about 7.5 mm, and about 9 mm, about 12 mm. The shell may have a height (maximum extension along the second axis) in the range from about 3 mm to about 30 mm, such as in the range from about 4 mm to about 20 mm, such as about 6 mm, about 8 mm, about 10 mm, about 12 mm, about 14 mm or about 16 mm. The shell may have a width (maximum extension along the third axis) in the range from about 3 mm to about 30 mm, such as in the range from about 4 mm to about 20 mm, such as about 6 mm, about 8 mm, about 10 mm, about 12 mm, about 14 mm or about 16 mm. The outer surface of the shell may have a double curved surface to facilitate oral administration of a pharmaceutical composition.

The shell included in the pharmaceutical compositions according to the present description may include one or more reinforcement elements extending from the inner surface of the outer shell wall. A reinforcement element may extend fully or partly from a first end to a second end or between a first end and a second end. The use of one or more reinforcement elements enables a production of a pharmaceutical composition having a relatively thinner outer shell wall, while still maintaining desired hardness or structural integrity performance such that abuse by physical tampering may be deterred. Where the pharmaceutical composition described herein includes one or more reinforcement elements, the one or more reinforcement elements may comprise one or more protrusions extending from the inner surface of the outer shell wall into the cavity formed by the inner surface. Beyond enhancing the structural integrity of the pharmaceutical composition described herein, reinforcement elements that extend from the inner surface of the outer shell wall into the cavity from by the inner surface may provide surfaces that facilitate mechanical fastening of the drug composition, such as a matrix composition, within the shell. Thus, wherein the pharmaceutical compositions described herein include one or more reinforcement elements, such reinforcement elements may also serve as anchoring elements for the drug composition. In certain embodiments, the one or more reinforcement elements included in a pharmaceutical composition according to the present description may comprise one or more rods, with each rod extending between two points on the inner surface of the shell. In another embodiment, the one or more reinforcement elements may comprise one or more reinforcement walls extending from the inner surface of the outer shell wall into the cavity formed by the inner surface of the shell wall. Where the reinforcement elements are provided as one or more reinforcement walls, the pharmaceutical composition may include a first reinforcement wall and/or a second reinforcement wall. Depending on the orientation and shape of a reinforcement wall, a reinforcement wall may assist or provide mechanical fastening of a matrix composition in the shell. Thus, a reinforcement wall may serve as anchoring element for the drug composition reinforcement. Where a reinforcement element is configured as a reinforcement wall, such a reinforcement wall may exhibit a substantially planar configuration. In an embodiment where the shell wall is configured to extend from a first end to a second end along a first axis, a first reinforcement wall and/or, if present, a second reinforcement wall may be configured to be positioned perpendicular to the first axis and partly or fully covering the cross sectional area of the cavity. In such an embodiment, the first reinforcement wall and/or, if present, the second reinforcement wall may be centered between the first end and the second end or displaced along the first axis.

In other embodiments where the shell wall is configured to extend from a first end to a second end along a first axis, a first reinforcement and/or, if present, a second reinforcement wall may be configured to be positioned parallel to the first axis. In such embodiments, the first reinforcement wall may be parallel to the second reinforcement wall, and the first reinforcement wall and the second reinforcement wall may extend in the same plane. Additionally, the first reinforcement wall and/or the second reinforcement wall may extend in a plane comprising a center axis parallel to the first axis or displaced along the second axis and/or the third axis.

In some embodiments, the pharmaceutical compostions described herein may include a first reinforcement wall intersects the second reinforcement wall forming an angle between the first reinforcement wall and the second reinforcement wall. The angle between the first reinforcement wall and the second reinforcement wall may be a right angle; however an angle in the range from 0° to 90°, e.g. 15°, 30°, 45°, 60° or 75° may be applied. An angle between walls is the smallest angle formed between the walls.

An reinforcement wall, e.g. the first reinforcement wall and/or the second reinforcement wall, may have a suitable thickness, such as in the range from about 0.2 mm to about 2 mm, such as in the range from about 0.4 mm to about 1.5 mm, such as 0.5 mm, 0.8 mm, 1.0 mm or 1.3 mm.

A reinforcement wall, e.g. the first reinforcement wall and/or the second reinforcement wall, may have one or more openings, e.g. for facilitating fixation of a matrix composition in the shell. One or more openings in a reinforcement wall may also facilitate filling of the shell with matrix composition. Reinforcement wall(s) may divide the cavity defined by the inner surface of the outer shell wall in a number of cavity parts. Cavity parts may be connected via opening(s) in reinforcement wall(s) or via passage(s) between reinforcement wall(s) and the inner surface of the outer shell wall. An opening included in a reinforcement wall may have any suitable shape, such as circular, oval, rectangular, triangular, angular, polygonal or star shaped. An opening may have any suitable size, such as an area in the range from about 1 $mm^2$ to about 100 $mm^2$, such as, in the range from about 3 $mm^2$ to about 20 $mm^2$, such as 5 $mm^2$, 10 $mm^2$, or 15 $mm^2$.

In an embodiment of the present invention, reinforcement element(s) are omitted, and the outer shell wall has suitable dimensions and material properties to provide a pharmaceutical composition exhibiting a structural integrity that reduce the susceptibility of the pharmaceutical composition to physical tampering.

In specific embodiments, the shell included in the pharmaceutical composition may constitute at least 40% w/w of the pharmaceutical composition. In certain such embodiments, the shell constitutes at least 45% w/w of the pharmaceutical composition, such as at least 50% w/w of the pharmaceutical composition. In one particular embodiment, the shell may constitute 68% w/w of the pharmaceutical composition.

In one or more embodiments, a pharmaceutical composition as described herein is resistant to abuse by chewing or other physical tampering (e.g. as can be measured by the particle size reduction test described herein), by including a shell which is extremely hard and unbreakable but otherwise inert. In one or more embodiments, a pharmaceutical composition as described herein is resistant to abuse by freezing, microwaving, burning, melting, mastication (i.e. chewing), reduction of the particle size, extraction, injection, snorting, by including a shell which is extremely hard and unbreakable but otherwise inert and/or including a gelling agent or an opioid antagonist in the matrix composition.

Beyond abuse resistance, pharmaceutical compositions as described herein, which are resistant to physical tampering, may also decrease incidents of legitimate, but non-compliant, use of pharmaceutical products, where the patient accidentally chews or crushes the pharmaceutical composition prior to or during administration, which might result in a partial or complete instant release of the active drug substance. Such incidents are potentially hazardous to the patient, particularly where the pharmaceutical composition is formulated for delivery of highly potent drug substances.

Shell Composition

The material used to form the shell included in the pharmaceutical compositions described herein is selected to provide a shell and pharmaceutical composition that is resistant to physical tampering. For example, one or more polymers and, optionally, one or more plasticizers may be selected to provide a shell having the desired physical properties. For purposes of the pharmaceutical compositions described herein, the materials used to form the shell are selected to be insoluble in and impermeable to water in order to ensure that the release of the active drug substance from the matrix composition is governed by the surface area of the drug composition that is left exposed by the shell In some embodiments, the shell is formed from a material that biodegrades, disintegrates, crumbles or dissolves after erosion of the matrix composition and/or during the release of the active drug substance in the matrix composition.

In specific embodiments, polymers are used to form the shell, and the polymers are thermoplastic polymers. As used herein, "thermoplastic polymers" refers to polymers that are an elastic and flexible liquid when heated, but freeze to a solid state when cooled. In certain such embodiments, the thermoplastic polymers used to form the shell are selected to exhibit a solid state at 20° C. or to ambient temperature.

The shell included in the pharmaceutical compositions described herein may be made of a material comprising one or more of the polymers described herein. For example, the shell may be formed of a material comprising one or more starch based polymers, one or more cellulose based polymers, one or more synthetic polymers, one or more biodegradable polymers, or a combination thereof, such as mixtures of starch and synthetic polymers or mixtures of starch and biodegradable polymers.

In one or more embodiments, the shell may be made of a material comprising one or more polymers selected from Ethyl cellulose grade 20 and 100, Polylactic acid (PLA), Cornpack 200, polycaprolactone, PEO 7000000, and polyhydroxybuturate.

When the shell comprises biodegradable polymers (such as polylactic acid), the shell may comprise at least 50% w/w biodegradable polymers, such as at least 60% w/w, at least 70% w/w, at least 80% w/w, such as at least 85% w/w, for example 86% w/w biodegradable polymers (such as polylactic acid).

In one or more embodiments, the shell material comprises one or more plasticizers. For example, in certain embodiments, the shell includes at the most 20% w/w plasticizer, such as at the most 17% w/w, such as at the most 15% w/w, for example 14% w/w, plasticizer. The plasticizer may be polyethylene oxides having a molecular weight of at least 200,000 daltons.

The shell may be made of a material comprising polylactic acid (PLA). Where the shell includes PLA, the shell may comprise at least 50% w/w PLA, such as at least 60% w/w, at least 70% w/w, at least 80% w/w, such as at least 85% w/w, for example 86% w/w, PLA.

Starch Based Polymers

The shell material may comprise one or more starch based polymers. The starch based polymer may be starch, as such, or a polymer having a starch content of more than 70% w/w, such as more than 80% w/w, for example, more than 90% w/w. Starch is a linear polysaccaride made up of repeating glucose groups with glycosidic linkages in the 1-4 carbon positions with chain lengths of 500 to 2,000 glucose units. Starch comprises two major polymer molecules—amylose and amylopectin.

The starch based polymers to be employed for a shell and pharmaceutical composition according to the present invention may be thermoplastic starch biodegradable plastics (TPS). TPS have starch (amylose) content larger than 70% w/w and are based on gelatinised vegetable starch. The vegetable starch may, for example, be selected from potato starch, rice starch, maize starch, tapioca starch, wheat starch, dextrin, carrageenan, chitosan. The vegetable starch may provide suitable polymers used in the shell composition. The group of starch based polymers, in general, does not have a specified melting point, but typically changes phase within a temperature range of 90° C. to 260° C., depending upon the chain length of the starch based polymer, water content, branching and added side-groups included in the polymer, and the degree of crystallinity of the starch. Long chained-starches are usually completely amorphous, while shorter length starches may be semi-crystalline (20-80% crystalline). In particular embodiments, materials exhibiting long polymer chains are used in the formation of the shell included in the pharmaceutical compositions described herein. Long polymer chains typically contribute to a material's hardness, while not being too brittle.

Starch-based polymers are in general fully biodegradable as they are products of plant materials. The degradation rate varies and can be further induced by addition of other biodegradable polymers, as listed herein.

An example of a suitable starch based polymer, which may be utilized in forming the shell material according to the present description is maize starch. Cornpack is the maize starch used in the examples described herein.

Starch is widely used in food and pharmaceutical industry as binder and diluent. It is edible and essentially nontoxic. Starch is, in general, inexpensive and attains a good hardness when molded and thermoformed. Starch materials may also be reheated several times without losing their thermodynamic properties. Accordingly, in some embodiments, the shell included in the pharmaceutical compositions described herein comprises at least one starch based polymer. In certain such embodiments, the shell included in the pharmaceutical compositions described herein comprises at least one starch. Starch materials can be selected to facilitate manufacture of the shell material such as by injection molding or co-extrusion production processes.

Starch based polymers are decomposable, and usually have a fast disintegration rate, especially in mixture with biodegradable polymers. These polymers are in generally recognized as stabile and inert in solid pharmaceutical composition.

Cellulose Based Polymers

The shell material may comprise one or more cellulose based polymers. In specific embodiments of the invention, the shell may even consist of one or more cellulose based polymers (such as ethyl cellulose) and platizicers (such as any of the plastizicers described herein) and UV stabilisers (such as any of the UV stabilisers described herein).

Cellulose based polymers are suited for use in formation of the shell composition because cellulose based polymers, such as, for example, ethylcellulose (particularly grade 100-300), often have increased hardness and high ductility.

Therefore, in particular embodiments, the shell may include a cellulose based polymer. Where a cellulose based polymer is used in the shell, the cellulose polymer may be selected to be substantially insoluble or insoluble in an aqueous medium, Suitable cellulose based polymers include, for example, cellulose polymers, wherein one or more of the free —OH groups have been substituted with an R-group to form a —O—R group. In this context, R may be, for example, a linear or branched lower alkyl, linear or branched lower alkyl-OH, linear or branched lower alkyl-COOH, —CO-(linear or branched lower alkyl), nitrate, aromatic rings or combinations of the aforementioned. Lower alkyl is preferably a $C_{1-10}$ alkyl, more preferably $C_{1-6}$ alkyl.

Accordingly, where a cellulose based polymer is used to formulate a shell as described herein, the cellulose based polymer may, for example, be one or more selected from ethylcellulose, cellulose acetate, cellulose propionate, cellulose nitrate, methylcellulose, carboxymethylcellulose and salts thereof, cellulose acetate phthalate, ethylhydroxyethylcellulose, ethylmethylcellulose, hydroxymethylcellulose, hydroxyethylmethylcellulose, hydroxypropylcellulose, hydroxypropylmethylcellulose, hydroxymethylcellulose and hydroxymethylpropylcellulose and cellulose acetate.

The shell may also comprise one or more cellulose based polymers selected from cellulose acetate, cellulose propionate, silicified microcrystalline cellulose, cellulose nitrate, methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose phthalate, hydroxymethylcellulose and hydroxymethylpropylcellulose, cellulose acetate, ceratonia (high molecular-weight 310 000), Cellulose based polymers are, in general, fully biodegradable, as they are typically products of plant materials. The degradation rate of cellulose based polymers is generally slower than that of starch based polymers. The degradation rate of cellulose based polymers, however, can be increased by addition of other biodegradable polymers as listed herein. Such additional polymers may be polymers susceptible to degradation by one or more microorganisms, which can result in quicker degradation of the shell composition into smaller pieces, giving rise to an increased surface area subject to degradation and, thereby, resulting in faster degradation.

In one or more preferred embodiments, the shell comprises ethyl cellulose $C_{12}H_{23}O_6(C_{12}H_{22}O_5)_nC_{12}H_{23}O_5$ wherein n can vary to provide a wide variety of molecular weights. Ethylcellulose, an ethyl ether of cellulose, is a long-chain polymer of β-anhydroglucose units joined together by acetal linkages Ethyl cellulose comes in different grades which varies in molecular weight and number of ethoxy groups. Grades from 20-300 are suitable for use in the present context and are also readily commercially available. Grades with high molecular weights tend to be preferred because they are optimal to give a hard shell. The shell may comprise one or more ethyl celluloses with different grades, for example one ethyl cellulose with a grade of in the range of 20 to 300, such as in the range of 50 to 200, in the range of 80 to 120, such as 100. Ethyl cellulose generally has a glass transition temperature within 129-133° C. These polymers are widely used in food and pharmaceutical industry as coater, stabilizer, matrix former and taste masking and are regarded as non toxic substances.

Cellulose based polymers are in general derived from plant material and may subsequently be modified. Many cellulose based polymers are inexpensive and provide a suitable hardness when moulded and thermoformed. As derivatives of plants, cellulose based polymers are, in general, easily decomposable when disposed. These polymers are stabile and inert in solid state.

Synthetic Polymers

The shell according to the invention may also comprise one or more synthetic polymers. Suitable synthetic polymers for use in the shell composition include, for example, one or more polymer selected from polyamide, polyethylene, polyethylene terephthalate, polypropylene, polyurethane, polyvinyl acetate, polyvinyl alcohol, polyvinyl butyral, polyvinyl chloride, silicone rubber, latex, teflon, copolymers such as ethylene vinyl acetate (EVA), styrene-butadienestyrene (SBS) and styrene-isoprene-styrene (SIS), Polyethylene glycols, polyvinylpyrrolidone, polyethylene oxide (ranging in molecular weights 100,000 to 8,000,000), Eudragit L methyl ester, Eudragit RL, and Eudragit E, carboxymethylene (Carbomer) and sugars thereof (e.g. allyl sucrose), and co-block polymers of ethylene and propylene oxide (Poloxamer).

Biodegradable Polymers

Biodegradation is the process by which microorganisms (microbes such as bacteria, fungi or algae) convert materials into biomass, carbon dioxide and water. Biomass is a general term used to refer to the cells of the microorganisms that are using the material as a carbon source to grow on.

The shell included in the pharmaceutical compositions described herein may alternatively or additionally comprise one or more biodegradable polymers. The biodegradable polymer(s) may be one or more selected from the starch based polymers, as described herein, and the cellulose based polymers, as described herein. However, the biodegradable polymer(s) may also be one or more selected from Polyhydroxybutyrate (PHB), polyhydroxyvalerate (PHV), polyhydroxyvalerate-co-hydroxyvalerate (PHVNH), Polyhydroxyalkanoates (PHA), poly-3-hydroxy-5-phenylvalerate (PHPV), Aliphatic polyesters, Polycaprolactone (PCL), polylactic acid (PLA), polyglycolic acid (PGA), co-polymers or co-block polymers of Polycaprolactone (PCL), Poly-propylene carbonate (PPC), polyester amide (PEA), polybutylene succinate adipate (PBSA), polybutylene adipate co-terephthalate (PBAT) and polybutylene succinate-adipate (PESA).

The shell may be formed using copolymers or co-block copolymers of polycaprolactone (PCL), polylactic acid (PLA) and/or polyglycolic acid (PGA). For example, a copolymer or co-block copolymer may be selected from poly(lactic-co-glycolic acid)(PLGA), polylactic acid and epsilon-caprolactone copolymer (PLA/CL) and polylactic acid/glycolic acid polymers)(PLA/GA), which are all commercially available.

In some embodiments, the shell comprises one or more biodegradable polymers selected from polylactic acid (PLA), polycaprolactone (PCL) and polyhydroxybutyrate (PHB). In one such embodiment, the shell comprises both polylactic acid (PLA), polycaprolactone (PCL) and polyhydroxybutyrate (PHB).

The use of polycaprolactone and other polymers in this group has been increased over the last decade, while the demand for environmental friendly plastics has grown. These polymers are regarded as nontoxic and are already used in parenteral pharmaceutical compositions. The advantages of these polymers are their ability to make a more flexible shell when moulded in mixture with starch derived polymers. Such polymers can be used to improve the somewhat rigid structure of pure thermoplastic starch. Furthermore, these polymers are decomposable and biodegradable.

Polylactic Acid

Polylactic acid or polylactide (PLA) is a biodegradable, thermoplastic, aliphatic polyester derived from renewable resources, such as corn starch. PLA belongs to the chemical family of polyesters, such as, for example, ε-caprolactone, PLA-caprolactone in different ratios 15% PLA to 100% (25, 35, 50, 75, 85%), polyglycolides, polyglycolic acids (PGA), poly (lactide-co-glycolide) in different ratios 15 to 100% PLA (25, 35, 50, 75, 85%), and poly (lactide-co-glycolide)-OH in different ratios 15% PLA to 100% (25, 35, 50, 75, 85%). Each of these polymers exists in L or D-form (making them optically active). When such polymers are provided in equal amounts (1:1) of L- and D-forms, the polymer material is an amorphous mixture, while the L- or D-forms, when provided alone possess a certain degree of crystallinity. The degree of crystallinity is highly related to the mechanical properties, such as processability and physico-chemical properties, particularly stability, of the polymer. A high degree of crystallinity provides hardness, and possibly, more brittleness. This may affect processability. Additionally, highly crystalline materials have a high melting temperature, hence process temperature, while amorphous esters have a lower melting temperature and thus a lower process temperature. Moreover, an increased degree of crystallinity implies that the material is more thermodynamically stable, which can lead to a longer shelf-life. A lower degree of crystallinity or completely amorphous materials are usually softer with a lower process temperature. A potential draw back of amorphous materials or materials with a lower degree of crystallinity is that their physical-chemical stability is lower due to their relatively thermodynamically unstable state.

Where PLA is used in forming the shell of the pharmaceutical compositions described herein, it is desirable to find the optimal degree of crystallinity. Each degree of crystallinity has different mechanical properties, thus adhesion between PLA and the matrix composition will vary depending on the degree of crystallinity of the given material (PLA).

The skeletal structure of PLA is shown below.

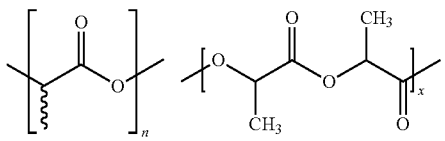

Due to the chiral nature of lactic acid, several distinct forms of polylactide exist. Poly-L-lactide (PLA in its L-form), which is referred to as PLLA, results from polymerization of L,L-lactide (also known as L-lactide), and poly-D-lactide (PLA in its D-form), which is referred to as PDLA, results from polymerization of L,L-lactide (also known as L-lactide). Furthermore, PLLA and PDLA may be mixed with various ratios of the two stereo forms. As the L-form has stronger mechanical properties than the D-form and the L-form has been used in pharmaceutical compositions, it is attempted to optimize the blend by adding the D-form to the L-form, such as, for example in amounts of 5, 10, 20, 30, 40% w/w up to a ratio of 1:1, consequently making the material completely amorphous. However, it may also form a highly regular stereo complex with increased crystallinity. Addition of PDLA increases the molecular energy of the mixture by forming a concentration gradient, and depending on the extent/magnitude of the temperature gradient, addition of PDLA may induce slow nucleation and, hence, crystallization. However, addition of PDLA may also induce a nucleation at an uncontrollable nucleation rate, which leads to an amorphous state.

PLA in its L-form has a crystallinity of around 35-45%, a glass transition temperature between 35-80° C., and a melting temperature between 173-178° C.

Due to the structure of PLA, PLA may be exposed to hydrolysis during its path through the gastro-intestinal tract, but PLA is impermeable and insoluble in aqueous media. In applying PLA as shell material, it has been demonstrated that the shell remains intact at least macroscopically, within the first 48 hours of exposure. Furthermore, the possible degradation product of PLA is merely lactic acid.

Polyglycols

The shell may comprise any of the below-mentioned polyglycols in a form that erodes at a substantially slower rate than the matrix composition. The shell may, therefore, be one which is eroded in an aqueous medium at a substantially slower rate than the matrix composition comprising the active drug substance, whereby, the area of the matrix composition comprising the active drug substance that is exposed during erosion and/or release of the matrix composition is substantially controlled and, whereby, the shell is substantially eroded upon erosion and/or release of the matrix composition comprising the active drug substance. Such a shell can be designed so that its longitudinal erosion rate is substantially the same as the longitudinal erosion and/or release rate of the matrix, whereby the matrix and the shell will erode longitudinally towards the centre of the pharmaceutical composition at substantially the same rate. Thus, when the matrix composition has been completely eroded and/or released by the aqueous medium, the shell will also be substantially completely eroded. A matrix composition having such a shell has the obvious advantage of being completely biodegraded upon release of the active drug substance.

A polyglycol suitable for use within the shell is high molecular weight PEO, such as, for example, PEO with an average molecular weight which is significantly higher that the average molecular weight of any of the PEOs contained in the matrix composition. Thus, where the shell composition includes a PEO, the PEO contained in the shell can be selected to have a significantly higher average molecular weight than any PEO contained in the drug composition. Examples of PEO materials suited to use in the shell include, for example, one or more PEO with an average molecular weight selected from at least 900,000, at least 2,000,000, at least 4,000,000, at least 6,000,000, and at least 7,000,000.

Mixtures of Polymers

As noted herein, the shell may comprise one or more different polymers and, in particular, one or more different polymers selected from starch based polymers, cellulose based polymers, synthetic polymers and biodegradable polymers, in particular from any of the starch based polymers, cellulose based polymers, synthetic polymers and biodegradable polymers described herein.

In one or more embodiments of the invention, the shell comprises polymers selected from starch based polymers and biodegradable polymers, such as from any of the starch based polymers and biodegradable polymers described herein. In particular, biodegradable polymers such as polycaprolactone, polyhydroxybuturate, polyhydroxyvalerate, polylactic acid, polyhydroxyalkanoates and polypropylene carbonate can be blended with various starches (such as any of the starches described herein) in different ratios. Suitable mixtures for use in the shell composition are, for example, polycaprolactone and sago and cassava starch, polycaprolactone or polyhydroxybuturate and pre-dried, thermoplastic starch, polycaprolactone and gelatinized starch or thermoplastic starch. Other suitable mixtures are starch-based blends with biodegradable thermoplastic components, like polyester amide, polyhydroxybuturate-co-valerate or polybutylene succinate-adipate. Polymers starches can be cross-linked with Maleic anhydride (MA) and dicumyl peroxide (DCP) to provide harder materials when molded and thermoformed.

In one or more embodiments, the shell comprises polymers selected from starch based polymers and synthetic polymers as described herein. In particular, suitable mixtures for use in the shell composition include, for example, native granular starch, modified starch, plasticized starch blended or grafted with one or more synthetic polymers such as polyethylene, polystyrene, Purified Terephthalic acid (PTA), optionally in mixture with aliphatic polyesters or polyvinyl alcohols in different ratios. Polybutylene succinate (PBS), polybutylene succinate adipate in blend with various starches in different ratios are also suitable for use in formulating the shell. For example, Polybutylene succinate in mixture with thermoplastic starch, or alkylene oxide modified starches in combination with hydrolyzed polyvinyl alcohol may be used to formulate the shell.

In one or more embodiments, the shell comprises polymers selected from the cellulose based polymers and biodegradable polymers described herein. Thus, the shell may, for example, comprise a mixture of PLA and ethylcellulose. In one or more embodiments, the shell consists of PLA, ethyl cellulose, one or more plasticizers (such as any of the plasticizers described herein below), and one or more UV stabilisers (such as any of the UV stabilisers described herein).

The shell may be made of a material comprising a single polymer, wherein the concentration of the polymer included in the shell is from 5 to 100% w/w.

The shell may be made of a material comprising a mixture of polymers, wherein the total concentration of polymers included in the shell is from 70 to 100% w/w.

UV Stabiliser

Radiation from sunlight can accelerate the degradation of plastics, such as the shell according to the invention, and packaging material that protects the pharmaceutical compositions from direct sunlight may provide sufficient protection against UV degradation. In particular, where the shell included in the pharmaceutical compositions described herein includes a high concentration of biodegradable polymers, incorporating one or more UV-stabilizers in the shell composition can work to stabilize the polymers (particularly the unsaturated functional groups that may be included in such polymers). UV-stabilizers suitable for use in the shell of the pharmaceutical composition include, for example, titanium dioxide, metal complexes with sulfur containing groups, hindered amine light stabilisers (HALS), benzophenones, and benzotriazoles. Titanium dioxide is already widely used in pharmaceutical preparations as pigment and is considered non toxic.

Plasticizer

In addition to above mentioned polymers, the shell may comprise one or more additional components. Thus, the shell may comprise at least one selected from
 i) polymers which are soluble or dispersible in water,
 ii) plasticizers, and
 iii) fillers/UV stabiliser.

By way of example, the shell material may include one or more plasticizer selected from Cetostearyl alcohol, castor oil, dibutyl sebacate, polyethylene oxides, and/or Poloxamer. However other plasticizers may also be used to provide desired material properties.

Other suitable plasticizers may be selected from, for example, mono- and di-acetylated monoglycerides, diacetylated monoglycerides, acetylated hydrogenated cottonseed glyceride, glyceryl cocoate, Polyethylene glycols or polyethylene oxides (e.g. with a molecular weight of 1,000-500,000 daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, β-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Flexol B-400, monomeric polyethylene ester, Piccolastic A-5, Piccalastic A-25, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols and mixtures thereof.

In certain embodiments, the shell includes plasticizer at a concentration of from 0 to 30% w/w.

The shell materials may further incorporate reinforcing fibers made of a material selected from, for example naturally derived fibers, such as plant derived fibers, synthetic materials, metal wires or steel bars, which increase the rigidity and/or integrity of the shell, thereby providing additional protection against physical tampering.

Shell Construction and Shell Composition

The physical characteristics of the shell included in the pharmaceutical compositions disclosed herein can be adjusted by selection of shell geometry and shell material properties. As will be appreciated upon review of the configurations and materials described herein, various combinations of shell geometry and composition can be utilized to provide a pharmaceutical composition having abuse resistant properties. In certain embodiments, the shell material substantially free of plasticizer is formed using a polycaprolactone polymer.

Shape of Matrix Compositions

The geometric form of the matrix composition can be adjusted to achieve a desired release rate of drug substance included within the matrix composition. For example, the matrix composition may be shaped to provide zero order release of a drug substance from the pharmaceutical compositions described herein. In particular, the shell of the pharmaceutical composition is configured in a manner that leaves a portion of the matrix composition exposed such that, upon administration, drug substance can be released from the exposed portion of the matrix composition.

In certain embodiments, the pharmaceutical composition described herein is configured such that the exposed releasing area of the matrix composition is constant and, thereby, provides for a zero order release of the drug substance included within the matrix composition. The area of the matrix composition exposed for deliver of drug substance can be adjusted simply by adjusting the configuration of the shell within which the matrix composition is disposed. In particular embodiments, the pharmaceutical composition includes shell including two ends and a cylindrical matrix composition disposed within the shell. One or both of the ends of the shell can include openings configured in manner that maintains surface area of the matrix composition exposed substantially constant. In such an embodiment, because the releasing area remains constant over the course of delivering the drug substance, the release profile of the drug substance will be zero order (or substantially zero order), provided that the release takes place via erosion of an exposed surface.

In one or more embodiments, the inner surface of the shell may define a cavity having a non-cylindrical shape. Such a configuration may be used to achieve a non-zero-order release profile of the drug substance contained within the matrix composition. For example, where the shell wall is configured to extend from a first end to a second end along a first axis, the cross sectional area perpendicular to the first axis may vary along the first axis. In such an embodiment, the cross sectional area may increase from the first end to the second end. Alternatively, the cross sectional area may increase from the first end to the center and decrease from the center to the second end. In yet another alternative embodiment, the cross sectional area may decrease from the first end to the center and increase from the center to the second end (hourglass figure). The change in cross sectional area along the first axis may be stepwise. As will be appreciated, upon administration of such a dosage form, as the matrix composition erodes, the surface area of the matrix composition available for delivery of the drug substanced included within the matrix composition changes and, thereby, alters the release rate of drug substance.

The term "cylindrical shape" as used herein refers to any geometrical shape having the same cross section area throughout the length of the geometrical shape (along an axis, e.g. the first axis). The cylindrical shape may be combined with reinforcement element(s) such as a wall and/or mesh or other reinforcement element. The cross section of a cylindrical cavity may have any two dimensional shape. For example, the cross section may be circular, oval, rectangular, triangular, angular, polygonal, or star shaped. The pharmaceutical compositions according to the invention may have a generally cylindrical shape, wherein the outer shell wall may be rounded at the first end and the second end. Additionally, where the shell wall is configured to extend from a first end to a second end along a first axis, the outer shell wall may taper along the first axis, i.e. the area of the outer shell surface cross section perpendicular to the first axis may vary, for example, decrease and/or increase along the first axis. Accordingly, in certain embodiments, the outer shell surface may be a double curved surface.

Optionally, the pharmaceutical compositions of the invention may be cylindrical pharmaceutical compositions having rounded and/or tapered end(s). The matrix composition may be of a cylindrical shape (optionally with tapered end(s)), which preferably is surrounded by a shell having at least one opening, with each opening exposing a surface of a matrix composition contained within the shell.

A cylindrical shape may be any geometrical shape having the same cross section area throughout the length of the geometrical shape. Within the present context, unless otherwise stated, cross sections are perpendicular to the longitudinal axis of the cylinder (first axis). By way of example, if the cylindrical shape is elongated then the cross sections are perpendicular to the first axis. Preferably, the cylindrical shape is elongated. The cross section of a cylinder within the meaning of the present invention may have any two dimensional shape, for example the cross section may be circular, oval, parabola, hyperbola, rectangular, triangular, polygonal, star shaped or an irregular shape. The pharmaceutical compositions according to the invention may have a generally cylindrical outer surface, wherein the end(s) may be tapered.

Accordingly, the cylindrical shape may, for example, be an elliptic cylinder, a parabolic cylinder, a hyperbolic cylinder, or a prism. A prism within the present context is a cylinder having a polygonal cross-section.

The pharmaceutical composition, as well as the matrix composition, as described herein may be a cylindrical shape with one tapered end or two tapered ends.

In an embodiment, the matrix composition is substantially surrounded by a shell having at least one opening. In one such embodiment, the shell includes a single opening exposing a surface of the matrix composition. In another such embodiment, the shell includes two opening exposing a surface of the matrix composition. The one or more openings included the shell of such embodiments may be positioned at one or both ends formed by the cylindrical shape of the matrix composition.

As described herein, the pharmaceutical compositions employed are provided with a shell. The shell is in general applied with a matrix composition in such a way that a surface or part of a surface of the matrix composition is exposed through one or more openings in the shell. Accordingly, during release of the active drug substance or erosion of the matrix composition, the release surface has a controlled surface area. In some embodiments, the surface area may be controlled such that it remains substantially constant, which would lead to a zero order release profile for the drug substance. In other embodiments, the surface area may be controlled such that it varies as the matrix composition erodes, which would lead to a non-zero order release profile and the matrix composition erodes. In the present context, controlled surface area relates to a predetermined surface area typically predicted from the shape of the shell of the pharmaceutical compositions described herein. It may have a simple uniform cylindrical shape or, in some embodiments, the cylindrical form can have one or more tapered ends in order to decrease (or increase) the initial release period.

FIGS. 1 (A, B and C) shows different views of an embodiment of the shell according to the present invention. In FIG. 1, an end view of the shell 2 having an outer shell wall 4 with a first end 6 and a second end 8 is shown. The outer shell wall 4 has an inner surface 10 defining a cylindrical cavity having an elliptical cross-section perpendicular to the first axis X. A first opening and a second opening is formed in the shell at the first end 6 and second end 8, respectively. FIG. 1B shows a cross section taken along line AA in FIG. 1A. FIG. 1C shows a cross section taken along line BB in FIG. 1A. The outer surface 12 of the outer shell wall 4 tapers slightly in order to facilitate injection moulding. Thus, the thickness of the outer shell wall 4 varies along the first axis X from 1.4 mm at the second end to 1.8 mm towards the first end, thus the maximum outer shell wall thickness is 1.8 mm. The length $d_1$ of the shell (extension along the first axis) is 7.5 mm. The height $d_2$ of the shell (extension along the second axis Y) is 9 mm. The width $d_3$ of the shell (extension along the third axis Z) is 13.5 mm. The inner surface of the outer shell wall defines a cylindrical cavity having an elliptic cross section ($a_{in}$, =5 mm, $b_{in}$=2.6 mm) perpendicular to the first axis X. A matrix composition may be filled into the cavity, thus providing a pharmaceutical composition as described herein in the form of a unit dosage form.

FIGS. 2 (A, B and C) shows different views of an embodiment of the shell according to the present invention. In FIG. 2A, an end view of the shell 102 is shown. The outer shell wall 4 has an inner surface 10 defining a cylindrical cavity having a circular cross-section perpendicular to the first axis X. FIG. 2B shows a cross section taken along line AA in FIG. 2A. FIG. 2C shows a cross section taken along line BB in FIG. 2A. The outer surface 12 of the outer shell wall 4 is rounded in order to facilitate injection moulding and oral administration. Thus, the thickness of the outer shell wall 4 varies along the first axis X. The maximum outer shell wall thickness is 4.5 mm. The length $d_1$ of the shell (extension along the first axis) is 7.5 mm. The height $d_2$ of the shell (extension along the second axis Y) is 12 mm. The width $d_3$ of the shell (extension along the third axis Z) is 16 mm. The inner surface of the outer shell wall defines a cylindrical cavity having a circular cross section perpendicular to the first axis X. The circular cross section has a diameter of 7 mm. A matrix composition may be filled into the cavity, thus providing a pharmaceutical composition as described herein in the form of a unit dosage form.

Figure 3C:
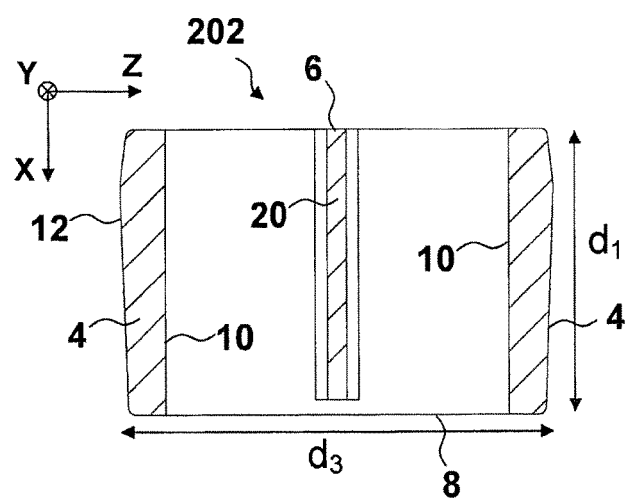

FIGS. 3 (A, B and C) shows different views of an embodiment of the shell according to the present invention. In FIG. 3A, an end view of the shell 202 is shown. The outer shell wall 4 has an inner surface 10 defining a cylindrical cavity having an elliptical cross-section perpendicular to the first axis X. FIG. 3B shows a cross section taken along line AA in FIG. 3A. FIG. 3C shows a cross section taken along line BB in FIG. 3A. The shell 202 comprises a first reinforcement wall 20 and a second reinforcement wall 22. The first reinforcement wall 20 and the second reinforcement wall 22 are plane and extend parallel to the first axis X. The first reinforcement wall 20 intersects the second reinforcement wall 22 forming a right angle between the first reinforcement wall 20 and the second reinforcement wall 22. The first reinforcement wall 20 and the second reinforcement wall 22 divide the cavity defined by the inner surface 10 of the outer shell wall 4 in four cavity parts. The first reinforcement wall 20 and the second reinforcement wall 22 extend from the first end 6 towards the second end 8, leaving a passage open at the second end 8 as seen in FIGS. 3B and 3C allowing matrix composition to be injected into all four cavity parts. The first reinforcement wall 20 and the second reinforcement wall 22 have a thickness of 0.5 mm. The use of reinforcement elements allows a thinner outer shell wall 4. The thickness of the outer shell wall 4 varies along the first axis X from 1.0 mm at the second end to 1.2 mm towards the first end. The maximum outer shell wall thickness is 1.2 mm. The length $d_1$ of the shell (extension along the first axis) is 7.5 mm. The height $d_2$ of the shell (extension along the second axis Y) is 7.5 mm. The width $d_3$ of the shell (extension along the third axis Z) is 11.5 mm. A matrix composition may be filled into the cavity, thus providing a pharmaceutical composition as described herein in the form of a unit dosage form.

FIGS. 4 (A, B and C) shows different views of an embodiment of the shell according to the present invention. The shell 302 is similar to the shell 202 of FIG. 3 but does not include the second reinforcement wall.

FIGS. 5 (A, B and C) shows different views of an embodiment of the shell according to the present invention. In FIG. 5A, an end view of the shell 402 is shown. The outer shell wall 4 has an inner surface 10 defining a cylindrical cavity having an elliptical cross-section perpendicular to the first axis X. FIG. 5B shows a cross section taken along line AA in FIG. 5A. FIG. 5C shows a cross section taken along line BB in FIG. 5A. The shell 402 comprises a plane first reinforcement wall 20 extending perpendicular to the first axis X and centered between the first end 6 and the second end 8. The first reinforcement wall 20 comprises a circular opening 24 with diameter 2.5 mm forming a connection between the two cavity parts. The first reinforcement wall 20 has a thickness of 0.5 mm. The thickness of the outer shell wall 4 varies along the first axis X from 1.0 mm at the second end to 1.2 mm towards the first end. The maximum outer shell wall thickness is 1.2 mm. The length $d_1$ of the shell (extension along the first axis) is 7.5 mm. The height $d_2$ of the shell (extension along the second axis Y) is 7.5 mm. The width $d_3$ of the shell (extension along the third axis Z) is 11.5 mm. A matrix composition may be filled into the cavity, thus providing a pharmaceutical composition as described herein in the form of a unit dosage form.

FIGS. 6 (A, B and C) show different views of an embodiment of the shell according to the present invention. In FIG. 6A, an end view of the shell 502 is shown. The outer shell wall 4 has an inner surface 10 defining a cylindrical cavity having an elliptical cross-section perpendicular to the first axis X. FIG. 6B shows a cross section taken along line AA in FIG. 6A. FIG. 6C shows a cross section taken along line BB in FIG. 6A. The shell 502 comprises a plane first reinforcement wall 20 and a plane second reinforcement wall 22 extending perpendicular to the first axis X in the same plane and centered between the first end 6 and the second end 8. The first reinforcement wall 20 and the second reinforcement wall 22 have a thickness of 0.5 mm. The thickness of the outer shell wall 4 varies along the first axis X from 1.0 mm at the second end to 1.2 mm towards the first end. The maximum outer shell wall thickness is 1.2 mm. The length $d_1$ of the shell (extension along the first axis) is 7.5 mm. The height $d_2$ of the shell (extension along the second axis Y) is 7.5 mm. The width $d_3$ of the shell (extension along the third axis Z) is 11.5 mm. The first reinforcement wall 20 and the second reinforcement wall 22 form an opening 24 forming a connection between the two cavity parts. A matrix composition may be filled into the cavity, thus providing a pharmaceutical composition as described herein in the form of a unit dosage form.

FIGS. 7 (A, B and C) show different views of an embodiment of the shell according to the present invention. The shell 602 corresponds to the shell 102 illustrated in FIGS. 2 (A, B and C) and additionally comprises a plane first reinforcement wall 20 extending perpendicular to the first axis X and centered between the first end 6 and the second end 8 of the shell 602. The first reinforcement wall 20 comprises a circular opening 24 with diameter 2 mm forming a connection between the two cavity parts. The first reinforcement wall 20 has a thickness of 1 mm.

Figure 8:
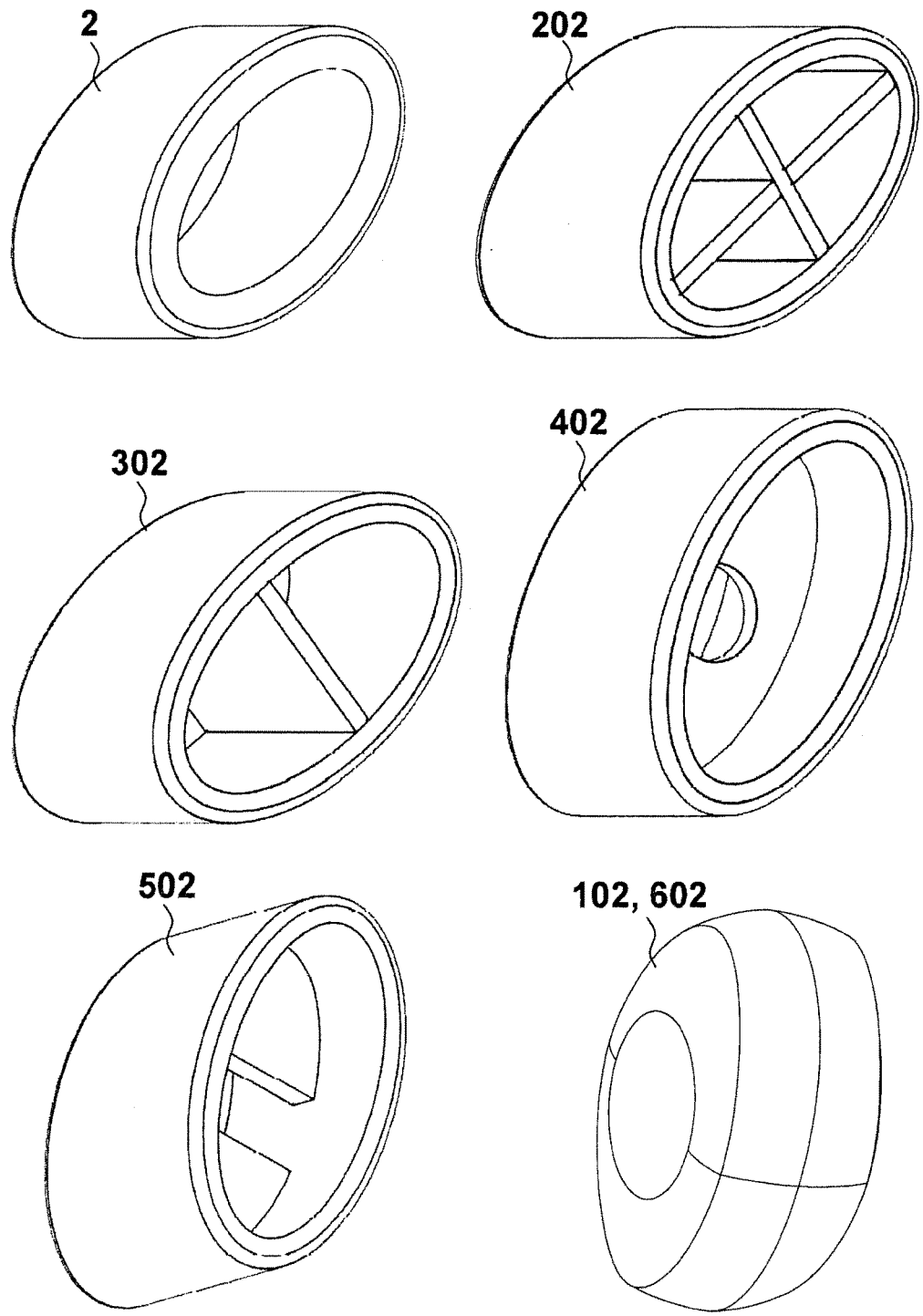
FIG. 8 illustrates perspective views of the shells of FIGS. 1, and 3-6.

FIG. 8 shows perspective views of shells illustrated in FIG. 1, and FIGS. 3-6.

Figures 9A, 9B, 9C, 9D:
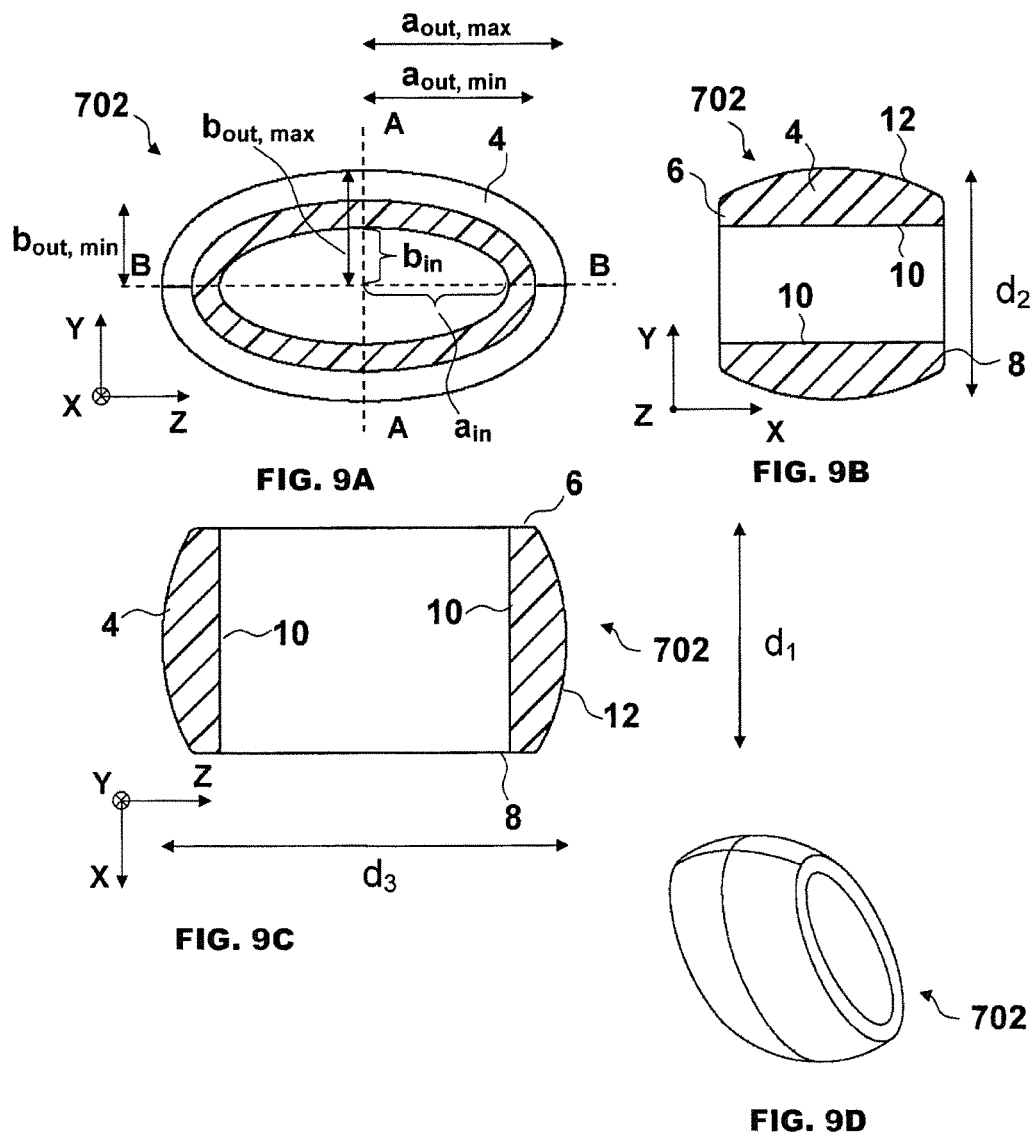
FIGS. 9A-9D schematically illustrate an exemplary shell according to the present invention.

FIGS. 9 (A, B, C and D) shows different views of an exemplary shell according to the present invention. FIG. 9A-B shows an end view of the shell 702 having an outer shell wall 4 with a first end 6 and a second end 8. The outer shell wall 4 has an inner surface 10 defining a cylindrical cavity having an elliptical cross-section perpendicular to the first axis X. The ellipse formed by the inner shell surface 10 has semimajor axis $a_{in}$ =4.8 mm parallel to the third axis and semiminor axis $b_{in}$=1.9 mm parallel to the second axis. A first opening and a second opening is formed in the shell at the first end 6 and second end 8, respectively. FIG. 9B shows a cross section taken along line AA in FIG. 9A. FIG. 9C shows a cross section taken along line BB in FIG. 9A. FIG. 9D shows a perspective view of the shell 702. The cylindrical cavity may take any suitable shape as described above. The outer surface 12 of the outer shell wall 4 has elliptical cross sections along the first axis X. The elliptical cross sections vary in size and area along the first axis, i.e. the outer surface 12 is a double-curved surface. The outer surface cross sections along the first axis have semimajor axes $a_{out}$ in the range from about 5.5 mm to about 6.7 mm and semiminor axes $b_{out}$ in the range from about 2.2 mm to about 4.5 mm. The thickness of the outer shell wall 4 varies along the first axis X from about 0.7 mm at the first and second ends increasing to about 1.9 mm in the center between the two ends. Accordingly, the maximum outer shell wall thickness is about 1.9 mm. The length $d_1$ of the shell 702 (extension along the first axis) is about 7.5 mm. The height $d_2$ of the shell 702 (extension along the second axis Y) is about 7.6 mm. The width $d_3$ of the shell 702 (extension along the third axis Z) is about 13.4 mm. A matrix composition may be filled into the cavity, thus providing a pharmaceutical composition as described herein in the form of a unit dosage form.

Examples of shell dimensions are disclosed in the table below, where $a_{out}$ is the range for the outer surface semimajor axis of cross-sections along the first axis, $b_{out}$ is the range for the outer surface semiminor axis of cross sections along the first axis, $a_{in}$ is the inner surface semimajor axis, and $b_{in}$ is the inner surface semimajor axis.

| Shell | $a_{out}$ ($a_{out,min}$-$a_{out,max}$)/ mm | $b_{out}$ ($b_{out,min}$-$b_{out,max}$)/ mm | $a_{in}$/mm | $b_{in}$/mm | $d_1$/mm |
|---|---|---|---|---|---|
| Example 1 | 3.4-4.8 | 2.2-3.6 | 2.4 | 1.2 | 7.5 |
| Example 2 | 4.1-5.7 | 2.7-4.2 | 3.3 | 1.7 | 7.5 |
| Example 3 | 5.9-7.5 | 3.0-4.3 | 4.8 | 1.9 | 7.5 |
| Example 4 | 10.1-11.4 | 2.7-4.5 | 9.0 | 2.0 | 7.5 |
| Example 5 | 2.5-4.0 | 2.1-3.5 | 0.9 | 0.9 | 7.5 |
| Example 6 | 2.3-4.0 | 2.1-3.5 | 1.6 | 1.0 | 7.5 |
| Example 7 | 4.0-5.4 | 2.4-3.6 | 2.9 | 1.2 | 7.5 |
| Example 8 | 5.1-6.4 | 2.8-4.1 | 4.0 | 1.7 | 7.5 |
| Example 9 | 9.0-10.3 | 2.8-4.1 | 7.8 | 1.7 | 7.5 |
| Example 10 | 2.0-4.0 | 1.8-3.5 | 0.9 | 0.9 | 7.5 |
| Example 11 | 2.6-4.0 | 2.0-3.5 | 1.6 | 1.1 | 7.5 |
| Example 12 | 4.0-5.4 | 2.4-3.6 | 2.9 | 1.2 | 7.5 |
| Example 13 | 5.1-6.4 | 2.8-4.1 | 4.0 | 1.7 | 7.5 |
| Example 14 | 9.0-10.3 | 2.8-4.1 | 7.8 | 1.7 | 7.5 |
| Example 15 | 4.0-5.2 | 2.5-4.8 | 2.8 | 1.4 | 7.5 |
| Example 16 | 4.5-5.7 | 2.6-4.0 | 3.3 | 1.6 | 7.5 |
| Example 17 | 5.6-7.0 | 2.8-4.2 | 4.5 | 1.8 | 7.5 |
| Example 18 | 6.7-7.9 | 2.9-4.3 | 5.5 | 1.9 | 7.5 |

The minimum semimajor axis of the elliptic outer shell surface cross sections may be given by: $a_{out,min}=a_{in}+\beta_1$, where $\beta_1$ is at least 0.5 mm, such as at least 0.7 mm, e.g. in the range from about 1.0 mm to about 2.5 mm. In one or more embodiments of the shell, $\beta_1$=1.1 mm in order to provide desired strength and at the same time enable a pharmaceutical composition that is easy to swallow.

The minimum semiminor axis of the elliptic outer shell surface cross sections may be given by: $b_{out,min}=b_{in}+\beta_2$, where $\beta_2$ is at least 0.5 mm, such as at least 0.7 mm, e.g. in the range from about 1.0 mm to about 2.5 mm. In one or more embodiments of the shell, $\beta_1$=1.1 mm in order to provide desired strength and at the same time enable a pharmaceutical composition that is easy to swallow.

The outer shell surface 12 of the shell 702 in a cross section perpendicular to the second axis (see FIG. 9C) forms a circular arc with r=$d_1$, i.e. $\alpha$=1. Further, the outer shell surface 12 of the shell 702 in a cross section perpendicular to the third axis (see FIG. 9B) forms a circular arc with r=$d_1$, i.e. $\alpha$=1.

FIGS. 10 (A, B, C and D) illustrates an exemplary shell for a pharmaceutical composition. FIG. 10A is an end view of the shell 802. FIG. 10B shows a cross section taken along line AA in FIG. 10A. FIG. 10C shows a cross section taken along line BB in FIG. 10A. FIG. 10D shows a perspective view of the shell 802. The shell 802 extends from a first end 6 to a second end 8 along a first axis. The shell 802 defines a number of cavities 804 extending from the first end 6 to the second end 8. The shell 802 defines ten cavities 804; however any suitable number of cavities, such as two, three, four, five, six, seven, eight, nine, ten, or more may be employed. The cavities 804 are circular cylindrical cavities with a suitable radius, e.g. in the range from about 0.5 mm to about 4.0 mm. In the shell 802, the cavity radii are about 0.96 mm. Different radii for different cavities may be employed. The ten cavities 804 are arranged in a 2×5 matrix configuration. It is to be noted that any suitable configuration of cavities may be employed. For example, the number and cross sectional size and shape of the cavities may be adjusted as desired. Optionally, each cavity 804 comprises a reinforcement element 806 extending from the inner shell surface into the cavity. The reinforcement elements 806 extend from the inner surface as annular protrusions perpendicular to the first axis X. The reinforcement elements 806 may also be referred to as reinforcement walls comprising a circular opening 808. In addition to improving the strength of the shell 802, the reinforcement elements 806 also function as anchoring elements for matrix compositions accommodated in the cavities 804. Thereby, the reinforcement elements 806 ensure that matrix composition cannot be removed from the cavities 804 without breaking or crushing the matrix composition, increasing the resistance to abuse achieved by the pharmaceutical composition. The length $d_1$ of the shell 802 (maximum extension along the first axis) is about 7.5 mm. The height $d_2$ of the shell 802 (maximum extension along the second axis Y) is about 7.0 mm. The width $d_3$ of the shell 802 (maximum extension along the third axis Z) is about 16.5 mm. A matrix composition may be filled into the cavities 804, thus forming a pharmaceutical composition.

The outer shell surface 12 of the shell 802 forms a double curved surface. The height $d_2$ of the shell varies along the first axis from about 4.8 mm at the first and second ends to about 7 mm at the centre between the two ends. The width $d_3$ varies along the first axis from about 13.5 mm at the first and second ends to about 16 mm at the centre between the two ends.

Drug Composition

The pharmaceutical compositions described herein comprise a drug composition, also referred to herein as a "matrix composition." The matrix composition may comprise one or more polymers. A general description of materials and methods that may be utilized in the formulation of the matrix compositions in the pharmaceutical compositions described herein may be found in WO 89/09066, WO 91/004015, WO 95/22962, WO 99/51208, WO 03/024429, WO 03/024426, WO 03/024430, WO 2004/041252, WO 2004/084869, WO 2004/084868, WO 2006/128471, WO 2008/086804, and WO 2008/148798, each of which is herein incorporated by reference.

Suitable polymers for the matrix composition typically comprise a polyglycol. Polyglycols suitable for use in the matrix composition may be provided in the form of a homopolymer and/or a copolymer. In certain embodiments, the polymer is substantially water soluble, thermoplastic, crystalline, semi-crystalline or amorphous or a mixture of substantially water soluble, crystalline, semi-crystalline or amorphous polymers. Suitable polymers for use in a matrix composition are polyethylene glycols, including derivatives such as mono and dimethoxypolyethylene glycols (mPEGs), polyethylene oxides and/or block copolymers of ethylene oxide and propylene oxide.

Polyethylene glycols (PEGs) are linear polydisperse polymers composed of repeating units of ethylene glycol. Their chemical formula is $HOCH_2[CH_2OCH_2]_mCH_2OH$, where m represents the average number of repeating units. Alternatively, the general formula $H[OCH_2CH_2]_nOH$ may be used to represent polyethylene glycol, where n is the number m+1 in the previous chemical formula. See the structural presentations of polyethylene glycol below. n is the average number of oxyethylene groups. n equals m+1.

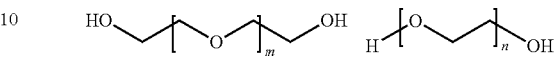

Polyethylene oxides (PEOs) are linear polydisperse non-ionic polymers composed of repeating units of ethylene oxide. Their chemical formula is $HO[CH_2CH_2O]_nH$, where n represents the average number of oxyethylene groups. See the structural presentation of polyethylene oxide below. n is the average number of oxyethylene groups. Depending on the applied preparation method high molecular weight of PEO may have one terminal methyl group.

Polyethylene glycols are mixtures of addition of ethylene glycol. In general PEG refers to polymers chains with molecular weights below 20,000, while PEO refers to higher molecular weights polymers. However, because of the similarities between PEO and PEG, the terms are often used interchangeably for the same compound.

Polyethylene glycols and/or polyethylene oxides suitable for use in the matrix composition include those having a molecular weights of at least about 20,000 daltons, such as, for example, from 20,000 to 700,000 daltons, from 20,000 to 600,000 daltons, from 35,000 to 700,000 daltons, from 35,000 to 500,000 daltons, from 35,000 to 400,000 daltons, from 35,000 to 300,000 daltons, from 50,000 to 300,000 daltons, such as, for example at least 35,000 daltons, at least 50,000 daltons, at least 75,000 daltons, at least 100,000 daltons, at least 150,000 daltons, at least 200,000 daltons, at least 250,000 daltons, at least 300,000 daltons or at least 400,000 daltons.

In particular embodiments, the polymer is a polyethylene oxide or a polyethylene glycol that has a molecular weight selected from at least 20,000 daltons, at least 35,000 daltons, at least 50,000 daltons, at least 100,000 daltons, at least 200,000 daltons, at least 300,000 daltons and at least 400,000 daltons. PEG is commercially available with average molecular weights up to 35 000. PEO is commercially available with average molecular weights up to 8,000,000. In specific embodiments, the polymer is a PEO having a molecular weight of at least 100,000 such as, for example, from 100,000 to 8,000,000, from 100,000 to 7,000,000, from 100,000 to 5,000,000, from 100,000 to 4,000,000, from 100,000 to 2,000,000, from 100,000 to 1,000,000, form 100,000 to 900,000. When PEO is employed with a molecular weight in the lower end, the PEO typically has a molecular weight as mentioned in the preceding paragraph. Commercially available PEOs with a molecular weight in the higher end have typically the following molecular weights: 900,000, 1,000,000, 2,000,000, 4,000,000, 5,000,000, 7,000,000, 8,000,000.

Poloxamers are copolymers or block copolymers and are a range of non-ionic surfactants of polyethylene glycol (PEG) and polypropylene glycol (PPG).

In chemical abstracts, Diol EO/PO block copolymers are described under the scientific name -hydroxy-hydroxypoly(oxyethylene)poly(oxypropylene)-poly(oxyethylene)-block copolymer in combination with the CAS register number.

In specific embodiments, a suitable poloxamer for use in a matrix composition has a HLB value of at least 18 such as, for example, at least 20. The mean molecular weight of a suitable poloxamer is typically at least 2,000.

Typical block copolymers of ethylene oxide and propylene oxide have a molecular weight of from 2,000 daltons, typically 3,000 to 30,000 daltons such as, for example from 4,000 to 15,000 daltons. Poloxamer may be the sole thermoplastic polymer in the matrix composition.

Mixtures of PEO with different average molecular weights can be used in order to obtain a PEO with a desirable average molecular weight. The same applies to PEG.

The polymer has a melting point higher than the body temperature of the human in which the pharmaceutical composition is to be used. Thus, the polymer(s) employed in the matrix composition can be selected from polymers have a melting point of 20-120° C. such as, for example from 30 to 100° C. or from 40 to 80° C.

In one or more preferred embodiments of the invention, the matrix composition comprises at least one polyethylene oxide and at least one copolymer.

In addition, or as an alternative, to a polymer of a polyglycol type, the matrix composition may comprise polymer(s) selected from: modified or unmodified water soluble natural polymers, such as glucomannan, galactan, glucan, polygalacturonic acid, polyxylane, polygalactomannans, rhanogalacturonan, polyxyloglycan, arabinogalactan, and starch, cellulose and derivatives thereof, chitosan, alginate, fibrin, collagen, gelatin, hyaluronic acid, amylopectin, pectin including low methylated or methoxylated pectins, dextran and fatty acids and alcohols; synthetic polymers such as polyvinylpyrrolidone (PVP), polyvinyl acetate (PVA), polyvinylbutyral (PVB), Eudragit L methyl ester, Eudragit L, Eudragit RL, Eudragit E, Eudragit S, PHPV, PHA, Polycaprolactone (PCL), poly(lactic-co-glycolic acid) (PLGA) and polylactic acid (PLA); and hydrogels made from the polymers or combined polymers mentioned above and or from polymers originated from, for example, 2-Hydroxyethyl Methacrylate (HEMA), Ethyleneglycol dimethacrylate (EDGMA), N-Vinyl-2-Pyrrolidone (NVP), acrylamide, hydroxypropyl methacrylate (HPMA), polyethylene glycol acrylate (PEGA), Polyethylene glycol methacrylate (PEGMA), Poly(ethylene glycol) dimethacrylates (PEGDMA), Polyethylene glycol diacrylate (PEGDA), and Poly(ethylene glycol) dimethacrylates (PEGDMA).

One or more polymers are typically present in a matrix composition in a concentration amount of from 5 to 99.9% w/w, such as from 10 to 95% w/w such as from 15 to 90% w/w, such as from 20 to 85% w/w, such as from 30 to 85% w/w calculated as w/w % of the matrix composition.

In one or more embodiments of the invention, the total concentration of polymers in the matrix composition is in the range of from 5 to 95% w/w, such as from 5 to 80% w/w, such as from 10 to 80% w/w, such as from 20 to 80% w/w, such as from 30 to 80% w/w, such as from 40 to 80% w/w, for example, from 45 to 80% w/w.

In one or more embodiments, then the concentration of the homopolymers in the matrix composition is in the range of 5 to 90% w/w, such as in the range of 20 to 85% w/w, for example, in the range of 20 to 75% w/w, such as in the range of 20 to 70% w/w, In some embodiments, the concentration of the polyglycol copolymer in the matrix composition, if present in combination with a polyglycol homopolymer, is in the range of 0 to 60% w/w, such as for example 0 to 30% w/w. If the copolymer is the sole thermoplastic polymer in the matrix composition the concentration may be from about 5 to about 99.5% w/w such as those ranges described above and described for the homopolymer.

In those cases, where mixture of polymers are present in the matrix composition, the concentration of an individual polymer in the matrix composition may typically be from 0 to 95% w/w such as, for example, from 5 to 90% w/w, from 10 to 90% w/w, from 10 to 80% w/w, from 10 to 70% w/w, from 10 to 60% w/w, from 10 to 50% w/w, from 15 to 50% w/w, from 15 to 45% w/w, from 15 to 40% w/w, from 20 to 40% w/w, from 20 to 35% w/w or from 20 to 30% w/w. The concentration is from 0 to 75% w/w, from 10 to 75% w/w, from 20 to 50% w/w, from 20 to 55% w/w. Polymers may also be present in low concentrations such as, for example, from 0 to 20% w/w.

The total concentration of the polymers (notably the sum of homo- and copolymers of the polyglycol type) in the matrix composition can be from 5 to 99.9% w/w, such as from 10 to 95% w/w, from 15 to 90% w/w, such as from 20 to 85%, such as from 30 to 85%, from 30 to 99% w/w, such as, for example, from 35 to 95% w/w, from 35 to 90% w/w, from 35 to 85% w/w, from 35 to 80% w/w, from 40 to 75% w/w, from 45 to 70% w/w, from 45 to 65% w/w, from 55 to 85% w/w, or from 60 to 85% w/w. More specifically, the concentration can be selected from 5 to 85% w/w, from 20 to 85% w/w, from 30 to 85% w/w, and from 40 to 85% w/w.

The concentration of the polyglycol homopolymer can be from 5 to 99.9% w/w, such as from 20 to 90% w/w or from 30 to 90% w/w, and, in those cases where the homopolymer is the only thermoplastic polymer present in the matrix composition, then the concentration can be from 50 to 95% w/w, such as, for example, from 55 to 90% w/w, from 60 to 90% w/w, from 65 to 90% w/w, from 70 to 90% w/w or from 70 to 85% w/w. The concentration can be selected from 10 to 75% w/w, from 20 to 75% w/w, from 25 to 75% w/w, and from 30 to 75% w/w.

The concentration of the polyglycol copolymer, if present in combination with a polyglycol homopolymer, can be from 1 to 60% w/w, such as, for example, from 2.5 to 50% w/w, or from 5 to 45% w/w. If the copolymer is the sole thermoplastic polymer in the matrix composition, the concentration may be from 5 to 99.5% w/w, such as those ranges described above and described for the homopolymer. Alternatively, the concentration of polyglycol copolymer with a polyglycol homopolymer may be from 0 to 25% w/w.

Active Drug Substances

A matrix composition comprises one or more active drug substances. The amount of substance is determined by the therapeutic index of the indication for which the active drug substance is intended. Typically, the amount of the active drug substance corresponds to a daily or part of a daily therapeutic dose.

Active drug substances that are water soluble, as well those that are slightly soluble or insoluble in water, may be suitable active drug substances for inclusion in the drug composition included in the pharmaceutical compositions described herein.

Thus, a matrix composition may comprise one or more active drug substances substances that are therapeutically, prophylactically, diagnostically and/or biologically active drug substances. The term "active drug substance" as used herein broadly includes any compound, or mixture thereof, that can be delivered from the matrix composition to produce a beneficial result.

Examples of specific active drug substances suitable for use in a matrix composition of the invention are:

Antiinflammatory and antirheumatic active drug substances: Butylpyrazolidines, Phenylbutazone, Mofebutazone, Oxyphenbutazone, Clofezone, Kebuzone, Acetic acid derivatives and related substances, Indometacin, Sulindac, Tolmetin, Zomepirac, Diclofenac, Alclofenac, Bumadizone, Etodolac, Lonazolac, Fentiazac, Acemetacin, Difenpiramide, Oxametacin, Proglumetacin, Ketorolac, Aceclofenac, Bufexamac, Oxicams, Piroxicam, Tenoxicam, Droxicam, Lornoxicam, Meloxicam, Propionic acid derivatives, Ibuprofen, Naproxen, Ketoprofen, Fenoprofen, Fenbufen, Benoxaprofen, Suprofen, Pirprofen, Flurbiprofen, Indoprofen, Tiaprofenic acid, Oxaprozin, Ibuproxam, Dexibuprofen, Flunoxaprofen, Alminoprofen, Dexketoprofen, Fenamates, Mefenamic acid, Tolfenamic acid, Flufenamic acid, Meclofenamic acid, Coxibs, Celecoxib, Rofecoxib, Valdecoxib, Parecoxib, Etoricoxib, Lumiracoxib, Nabumetone, Niflumic acid, Azapropazone, Glucosamine, Benzydamine, Glucosaminoglycan polysulfate, Proquazone, Orgotein, Nimesulide, Feprazone, Diacerein, Morniflumate, Tenidap, Oxaceprol, Chondroitin sulfate, Feprazone, Dipyrocetyl, Acetylsalicylic acid, Quinolines, Oxycinchophen, Gold preparations, Sodium aurothiomalate, Sodium aurotiosulfate, Auranofin, Aurothioglucose, Aurotioprol, Penicillamine and similar agents, Bucillamine;

Analgesics: Opioids, Natural opium alkaloids, semi-synthetic opium alkaloids, Morphine, Opium, Hydromorphone, Nicomorphine, Oxycodone, Dihydrocodeine, Diamorphine, Papaveretum, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Other analgesics and antipyretics, Rimazolium, Glafenine, Floctafenine, Viminol, Nefopam, Flupirtine, Ziconotide.

Anaesthetics: Ethers, Diethyl ether, Vinyl ether, Halogenated hydrocarbons, Halothane, Chloroform, Methoxyflurane, Enflurane, Trichloroethylene, Isoflurane, Desflurane, Sevoflurane, Barbiturates, Methohexital, Hexobarbital, Thiopental, Narcobarbital, Opioid anaesthetics, Fentanyl, Alfentanil, Sufentanil, Phenoperidine, Anileridine, Remifentanil, Other general anaesthetics, Droperidol, Ketamine, Propanidid, Alfaxalone, Etomidate, Propofol, Hydroxybutyric acid, Nitrous oxide, Esketamine, Xenon, Esters of aminobenzoic acid, Metabutethamine, Procaine, Tetracaine, Chloroprocaine, Benzocaine, Amides, Bupivacaine, Lidocaine, Mepivacaine, Prilocaine, Butanilicaine, Cinchocaine, Etidocaine, Articaine, Ropivacaine, Levobupivacaine, Esters of benzoic acid, Cocaine, Other local anaesthetics, Ethyl chloride, Dyclonine, Phenol, Capsaicin;

Antimigraine active drug substances: Ergot alkaloids, Dihydroergotamine, Ergotamine, Methysergide, Lisuride, Corticosteroid derivatives, Flumedroxone, Selective serotonin (5HT1) agonists, Sumatriptan, Naratriptan, Zolmitriptan, Rizatriptan, Almotriptan, Eletriptan, Frovatriptan, Other antimigraine preparations, Pizotifen, Clonidine, Iprazochrome, Dimetotiazine, Oxetorone;

Antiepileptic active drug substances: Barbiturates and derivatives, Methylphenobarbital, Phenobarbital, Primidone, Barbexaclone, Metharbital, Hydantoin derivatives, Ethotoin, Phenytoin, Amino(diphenylhydantoin) valeric acid, Mephenytoin, Fosphenytoin, Oxazolidine derivatives, Paramethadione, Trimethadione, Ethadione, Succinimide derivatives, Ethosuximide, Phensuximide, Mesuximide, Benzodiazepine derivatives, Clonazepam, Carboxamide derivatives, Carbamazepine, Oxcarbazepine, Rufinamide, Fatty acid derivatives, Valproic acid, Valpromide, Aminobutyric acid, Vigabatrin, Progabide, Tiagabine, Other antiepileptics, Sultiame, Phenacemide, Lamotrigine, Felbamate, Topiramate, Gabapentin, Pheneturide, Levetiracetam, Zonisamide, Pregabalin, Stiripentol, Lacosamide, Beclamide;

Anticholinergic active drug substances: Tertiary amines, Trihexyphenidyl, Biperiden, Metixene, Procyclidine, Profenamine, Dexetimide, Phenglutarimide, Mazaticol, Bornaprine, Tropatepine, Ethers chemically close to antihistamines, Etanautine, Orphenadrine (chloride), Ethers of tropine or tropine derivatives, Benzatropine, Etybenzatropine;

Dopaminergic active drug substances: Dopa and dopa derivatives, Levodopa, Melevodopa, Etilevodopa, Adamantane derivatives, Amantadine, Dopamine agonists, Bromocriptine, Pergolide, Dihydroergocryptine mesylate, Ropinirole, Pramipexole, Cabergoline, Apomorphine, Piribedil, Rotigotine, Monoamine, oxidase B inhibitors, Selegiline, Rasagiline, Other dopaminergic agents, Tolcapone, Entacapone, Budipine;

Antipsychotic active drug substances: Phenothiazines with aliphatic side-chain, Chlorpromazine, Levomepromazine, Promazine, Acepromazine, Triflupromazine, Cyamemazine, Chlorproethazine, Phenothiazines with piperazine structure, Dixyrazine, Fluphenazine, Perphenazine, Prochlorperazine, Thiopropazate, Trifluoperazine, Acetophenazine, Thioproperazine, Butaperazine, Perazine, Phenothiazines with piperidine structure, Periciazine, Thioridazine, Mesoridazine, Pipotiazine, Butyrophenone derivatives, Haloperidol, Trifluperidol, Melperone, Moperone, Pipamperone, Bromperidol, Benperidol, Droperidol, Fluanisone, Indole derivatives, Oxypertine, Molindone, Sertindole, Ziprasidone, Thioxanthene derivatives, Flupentixol, Clopenthixol, Chlorprothixene, Tiotixene, Zuclopenthixol, Diphenylbutylpiperidine derivatives, Fluspirilene, Pimozide, Penfluridol, Diazepines, oxazepines and thiazepines, Loxapine, Clozapine, Olanzapine, Quetiapine, Neuroleptics, in tardive dyskinesia, Tetrabenazine, Benzamides, Sulpiride, Sultopride, Tiapride, Remoxipride, Amisulpride, Veralipride, Levosulpiride, Lithium, Other antipsychotics, Prothipendyl, Risperidone, Clotiapine, Mosapramine, Zotepine, Aripiprazole, Paliperidone;

Anxiolytic active drug substances: Benzodiazepine derivatives, Diazepam, Chlordiazepoxide, Medazepam, Oxazepam, Potassium clorazepate, Lorazepam, Adinazolam, Bromazepam, Clobazam, Ketazolam, Prazepam, Alprazolam, Halazepam, Pinazepam, Camazepam, Nordazepam, Fludiazepam, Ethyl Ioflazepate, Etizolam, Clotiazepam, Cloxazolam, Tofisopam, Diphenylmethane derivatives, Hydroxyzine, Captodiame, Carbamates, Meprobamate, Emylcamate, Mebutamate, Dibenzo-bicyclo-octadiene derivatives, Benzoctamine, Azaspirodecanedione derivatives, Buspirone, Other anxiolytics, Mephenoxalone, Gedocarnil, Etifoxine;

Hypnotic and sedative active drug substances: Barbiturates, Pentobarbital, Amobarbital, Butobarbital, Barbital, Aprobarbital, Secobarbital, Talbutal, Vinylbital, Vinbarbital, Cyclobarbital, Heptabarbital, Reposal, Methohexital, Hexobarbital, Thiopental, Etallobarbital, Allobarbital, Proxibarbal, Aldehydes and derivatives, Chloral hydrate, Chloralodol, Acetylglycinamide chloral hydrate, Dichloralphenazone, Paraldehyde, Benzodiazepineemepronium derivatives, Flurazepam, Nitrazepam, Flunitrazepam, Estazolam, Triazolam, Lormetazepam, Temazepam, Midazolam, Brotizolam, Quazepam, Loprazolam, Doxefazepam, Cinolazepam, Piperidinedione derivatives, Glutethimide, Methyprylon, Pyrithyldione, Benzodiazepine related active drug substances, Zopiclone, Zolpidem, Zaleplon, Ramelteon, Other hypnotics and sedatives, Methaqualone, Clomethiazole, Bromisoval, Carbromal, Scopolamine, Propiomazine, Triclofos, Ethchlorvynol, Valerian, Hexapropymate, Bromides, Apronal, Valnoctamide, Methylpentynol, Niaprazine, Melatonin, Dexmedetomidine, Dipiperonylaminoethanol;

Antidepressant active drug substances: Non-selective monoamine reuptake inhibitors, Desipramine, Imipramine, Imipramine oxide, Clomipramine, Opipramol, Trimipramine, Lofepramine, Dibenzepin, Amitriptyline, Nortriptyline, Protriptyline, Doxepin, Iprindole, Melitracen, Butriptyline, Dosulepin, Amoxapine, Dimetacrine, Amineptine, Maprotiline, Quinupramine, Selective serotonin reuptake inhibitors, Zimeldine, Fluoxetine, Citalopram, Paroxetine, Sertraline, Alaproclate, Fluvoxamine, Etoperidone, Escitalopram, Monoamine oxidase inhibitors, non-selective, Isocarboxazid, Nialamide, Phenelzine, Tranylcypromine, Iproniazide, Iproclozide, Monoamine oxidase A inhibitors, Moclobemide, Toloxatone, Other antidepressants, Oxitriptan, Tryptophan, Mianserin, Nomifensine, Trazodone, Nefazodone, Minaprine, Bifemelane, Viloxazine, Oxaflozane, Mirtazapine, Medifoxamine, Tianeptine, Pivagabine, Venlafaxine, Milnacipran, Reboxetine, Gepirone, Duloxetine, Agomelatine, Desvenlafaxine, Centrally acting sympathomimetics, Amfetamine, Dexamfetamine, Metamfetamine, Methylphenidate, Pemoline, Fencamfamin, Modafinil, Fenozolone, Atomoxetine, Fenetylline, Xanthine derivatives, Caffeine, Propentofylline, Other psychostimulants and nootropics, Meclofenoxate, Pyritinol, Piracetam, Deanol, Fipexide, Citicoline, Oxiracetam, Pirisudanol, Linopirdine, Nizofenone, Aniracetam, Acetylcarnitine, Idebenone, Prolintane, Pipradrol, Pramiracetam, Adrafinil, Vinpocetine;

Anti-dementia active substances: Anticholinesterases, Tacrine, Donepezil, Rivastigmine, Galantamine, Other anti-dementia active drug substances, Memantine, *Ginkgo biloba;*

Other nervous system active drug substances: Parasympathomimetics, Anticholinesterases, Neostigmine, Pyridostigmine, Distigmine, Ambenonium, Choline esters, Carbachol, Bethanechol, Other parasympathomimetics, Pilocarpine, Choline alfoscerate;

Active drug substances used in addictive disorders: Nicotine, Bupropion, Varenicline, Disulfiram, Calcium carbimide, Acamprosate, Naltrexone, Buprenorphine, Methadone, Levacetylmethadol, Lofexidine. Antivertigo active drug substances; Betahistine, Cinnarizine, Flunarizine, Acetylleucine, Gangliosides and ganglioside derivatives, Tirilazad, Riluzole, Xaliproden, Hydroxybutyric acid, Amifampridine;

Opium alkaloids and derivatives: Ethylmorphine, Hydrocodone, Codeine, Opium alkaloids with morphine, Normethadone, Noscapine, Pholcodine, Dextromethorphan, Thebacon, Dimemorfan, Acetyldihydrocodeine, Benzonatate, Benproperine, Clobutinol, Isoaminile, Pentoxyverine, Oxolamine, Oxeladin, Clofedanol, Pipazetate, Bibenzonium bromide, Butamirate, Fedrilate, Zipeprol, Dibunate, Droxypropine, Prenoxdiazine, Dropropizine, Cloperastine, Meprotixol, Piperidione, Tipepidine, Morclofone, Nepinalone, Levodropropizine, Dimethoxanate and Naltrexone;

The active drug substance may, for example, be an active drug substance with abuse potential or safety risk suitable. Such active drug substance may, for example, be selected from:

1-(1-Phenylcyclohexyl)pyrrolidine, 1-(2-Phenylethyl)-4-phenyl-4-acetoxypiperidine, 1-[1-(2-Thienyl)-cyclohexyl]piperidine, 1-[1-(2-Thienyl)cyclohexyl]pyrrolidine, 1-Methyl-4-phenyl-4-propionoxy-piperidine, 1-Phenylcyclohexylamine, 1-Piperidinocyclohexane-carbonitrile, 2,5-Dimethoxy-4-ethylamphetamine, 2,5-Dimethoxyamphetamine, 2C-B (i.e. 4-bromo-2,5-dimethoxypenethylamine), 2C-D (i.e. 2,5-dimethoxy-4-methyl-phenethylamine), 2C-I (i.e. 4-iodo-2,5-dimethoxy-phenethylamine), 2C-T-2 (i.e. 2,5-dimethoxy-4-ethylthiophenethylamine), 2C-T-4 (i.e. 2,5-dimethoxy-4-isopropyl thiophenethylamine), 2C-T-7 (i.e. 2,5-dimethoxy-4-(n)-propylthiopenethylamine), 3,4-Methylene-dioxymethamphetamine, 3,4,5-Trimethoxyamphetamine, 3,4-Methylenedioxyamphetamine, 3,4-Methylenedioxy-N-ethylamphetamine, 3-Methylfentanyl, 3-Methylthiofentanyl, 4-Bromo-2,5-dimethoxyamphetamine, 4-Bromo-2,5-dimethoxy-phenethylamine, 4-Methoxyamphetamine, 4-Methyl-2,5-dimethoxyamphetamine, 4-Methylaminorex (cis isomer), 5-MeO-DIPT (i.e. 5-Methoxy-N,N-diisopropyltryptamine), 5-MeO-DMT (i.e. 5-Methoxy-N,N-dimethyltryptamine), 5-Methoxy-3,4-methylenedioxyamphetamine, Acetorphin, Acetorphine, Acetyl-alpha-methylfentanyl, Acetyldihydrocodeine, Acetylmethadol, Alfentanil, Allobarbital, Allylprodin, Allylprodine, Alphacetylmethadol, levo-alphacetylmethadol, Alpha-ethyltryptamine, Alphameprodine, Alphamethadol, Alpha-Methylfentanyl, Alpha-Methylthiofentanyl, Alphaprodine, Alprazolam, Amfepramon, Amfetaminil, Amineptin, Aminorex, Amobarbital, Amphetamine, Dexamphetamine, Lisdexamphetamine, Amylnitrit (all isomers of the amyl group), Anabolic steroids, Anileridine, Aprobarbital, Barbital, Barbituric acid derivative, BDB (i.e. 3,4-methylenedioxyphenyl)-2-butanamine), Benzethidin, Benzethidine, Benzoylecgonine, Benzphetamine, Benzphetamine, Benzylmethylketon, Benzylmorphine, Betacetylmethadol, Beta-Hydroxy-3-methylfentanyl, Beta-Hydroxyfentanyl, Betameprodine, Betameprodine, Betamethadol, Betaprodine, Bezitramide, Bezitramide, Boldenone, Brolamfetamin, Bromazepam, Brotizolam, Bufotenine, Buprenorphine, Butabarbital, Butalbital, Butobarbital, Butorphanol, BZP (A 2)(i.e. 1-benzylpiperazin), Camazepam, *Cannabis*, Carfentanil, Catha *edulis*, Cathine, Cathinone, Chloral betaine, Chloral hydrate, Chlordiazepoxide, Chlorhexadol, Chlorotestosterone (same as clostebol), Chlorphentermine, Clobazam, Clonazepam, Clonitazene, Clonitazene, Clorazepate, Clortermine, Clostebol, Clotiazepam, Cloxazolam, Coca Leaves, Cocaine, Codeine, Codeine & isoquinoline alkaloid, Codeine methylbromide, Codeine-N-oxide, Codoxim, Cyclobarbital (Hexemal NFN), Cyprenorphine, Dehydrochlormethyltestosterone, Delorazepam, Desomorphine, Dexamphetamine, Dexfenfluramine, Dextromoramide, Dextropropoxyphene, Diacetylmorphine, Diampromide, Diazepam, Dichloralphenazone, Diethylpropion, Diethylthiambutene, Diethyltryptamine, Difenoxin, Dihydrocodeine, Dihydroetorphine, Dihydromorphine, Dihydrotestosterone, Dimenoxadol, Dimepheptanol, Dimethylthiambutene, Dimethyltryptamine, Dioxaphetyl butyrate, Diphenoxylate, Dipipanone, Diprenorphine, Dronabinol, Drostanolone, Drotebanol, Ecgonine, Estazolam, Ethchlorvynol, Ethinamate, Ethyl Ioflazepate, Ethylestrenol, Ethylmethylthiambutene, Ethylmorphine, Ethylmorphine, Eticyclidin, Etilamphetamine, Etonitazene, Etorphine, Etoxeridine, Etryptamine, Fencamfamin, Fenethylline, Fenetylline, Fenfluramine, Fenproporex, Fentanyl, Fludiazepam, Flunitrazepam, Fluoxymesterone, Flurazepam, Formebolone, Fungi and Spores of the species Psilocybe Semilanceata, Furethidine, Gammahydroxybutanic acid, Glutethimide, Halazepam, Haloxazolam, Heroine, Hydrocodone, Hydrocodone & isoquinoline alkaloid, Hydromorphinol, Hydromorphone, Hydroxypethidine, Ibogaine, Isobutylnitrit, Isomethadone, Ketamine, Ketazolam, Ketobemidone, Levamphetamine, Levo-alphacetylmethadol, Levo-methamphetamine, Levomethorphan, Levomoramide, Levophenacylmorphan, Levorphanol, Loprazolam, Lorazepam, Lormetazepam, Lysergic acid, Lysergic acid amide, Lysergic acid diethylamide, Marijuana, Mazindol, MBDN (i.e. N-methyl-1-(3,4-methylenedioxyphenyl)-2-butanamine), mCPP (i.e. 1-(3-chlorophenyl)piperazine), Mebutamate, Mecloqualone, Medazepam, Mefenorex, MeOPP (i.e. 1-(4-methoxyphenyl)piperazine), Meperidine, Meperidine intermediate, Meprobamate, Mescaline, Mesocarb, Mesterolone, Metamphetamine, Metazocine, Methadone, Methadone intermediate, Methamphetamine, Methandienone, Methandranone, Methandriol, Methandrostenolone, Methaqualone, Methcathinone, Methenolone, Methohexital, Methyldesorphine, Methyldihydromorphine, Methylphenidate, Dexmethylphenidate, Methylphenobarbital (mephobarbital), Methyltestosterone, Methyprylone, Metopone, Mibolerone, Midazolam, Modafinil, Moramide-intermediate, Morpheridine, Morphine, Morphine methylbromide, Morphine methylsulfonate, Morphine-N-oxide, Myrophine, N,N-Dimethylamphetamine, Nabilone, Nalorphine, Nandrolone, N-Ethyl-1-phenylcyclohexylamine, N-Ethyl-3-piperidyl benzilate, N-Ethylamphetamine, N-Hydroxy-3,4-methylenedioxyamphetamine, Nicocodeine, Nicocodine, Nicodicodine, Nicomorphine, Nimetazepam, Nitrazepam, N-Methyl-3-piperidyl benzilate, Noracymethadol, Norcodeine, Nordiazepam, Norethandrolone, Norlevorphanol, Normethadone, Normorphine, Norpipanone, Norpipanone, Opium, Oxandrolone, Oxazepam, Oxazolam, Oxycodone, Oxymesterone, Oxymetholone, Oxymorphone, Para-Fluorofentanyl, Parahexyl, Paraldehyde, Pemoline, Pentazocine, Pentobarbital, Petrichloral, Peyote, Phenadoxone, Phenampromide, Phenazocine, Phencyclidine, Phendimetrazine, Phenmetrazine, Phenobarbital, Phenomorphan, Phenoperidine, Phentermine, Phenylacetone, Pholcodine, Piminodine, Pinazepam, Pipradrole, Piritramide, PMMA (paramethyxymethyl amphetamine), Prazepam, Proheptazine, Properidine, Propiram, Psilocybine, Psilocyn, Pyrovalerone, Quazepam, Racemethorphane, Racemoramide, Racemorphane, Remifentanil, *Salvia* divinorum, Salvinorin A, Secobarbital, Secobarbital, Sibutramine, SPA, Stanolone, Stanozolol, Sufentanil, Sulfondiethylmethane, Sulfonethylmethane, Sulfonmethane, Talbutal, Temazepam, Tenamfetamin, Testolactone, Testosterone, Tetrahydrocannabinols, Tetrazepam, TFMPP (i.e. 1-(3-trifluormethylphenyl)piperazine), Thebacon, Thebaine, Thiamylal, Thiofentanyl, Thiopental, Tiletamine & Zolazepam in Combination, Tilidine, Trenbolone, Triazolam, Trimeperidine, Vinbarbital, Zaleplon, Zipeprol, Zolpidem, and Zopiclon.

Other suitable examples of useful active drug substances for the matrix composition include alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethyithiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate, and pethidine.

Other suitable examples also include Anabolic steroids, *cannabis*, cocaine and diazepam.

In preferred embodiments, the active drug substance is selected from the therapeutic classes including non-steroids anti-inflammatory and antirheumatic active drug substances.

In certain embodiments, the active drug substance is selected from the therapeutic classes including analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-andrenergic, serotonin, $H_3$ antagonist used for ADHD, and nootropic agents used in addictive disorders.

In certain embodiments, the active drug substance is selected from the therapeutic classes including anaesthetics, centrally-acting analgesics, sedative-hypnotics, anxiolytics, appetite suppressants, decongestants, antitussives, antihistamines, antiemetics, antidiarrheals, and active drug substances used to treat narcolepsy and attention deficit hyperactivity disorder.

In some embodiments, the active drug substance is associated with abuse syndromes and the active drug substance may thus for example be selected from opioids, CNS depressants, CNS stimulants, cannabinoids, nicotine-like compounds, glutamate antagonists and N-methyl-D-aspartate (NMDA) antagonists.

In some embodiments, the active drug substance is selected from buprenorphine, codeine, dextromoramide, dihydrocodeine, fentanyl, hydrocodone, hydromorphone, morphine, pentazocine, oxycodeine, oxycodone, oxymorphone and tramadol.

In some embodiments, the active drug substance is selected from amphetamine, dexamphetamine, lisdexamphetamine, methamphetamine, methylphenidate and dexmethylphenidate.

In some embodiments, the active drug substances have abuse potential or safety risk. In principle, the use of a pharmaceutical composition to avoid alcohol dose dumping can be of relevance for any active drug substance. However, the main interest is with respect to active drug substances with abuse potential or safety risk.

The above mentioned active drug substances may also be in the form of pharmaceutically acceptable salts, uncharged or charged molecules, molecular complexes, solvates or anhydrates thereof, and, if relevant, isomers, enantiomers, racemic mixtures, and mixtures thereof.

Furthermore, the active drug substance may be in any of its crystalline, polymorphous, semi-crystalline, amorphous or polyamorphous forms.

The active drug substance may by modified to change physical-chemical properties of the drug substance, which may be by increasing or decreasing lipophilicity to modify the release characteristics of the active drug substance.

The term "pharmaceutically acceptable salts" of an active drug substance includes alkali metal salts, such as, for example, sodium or potassium salts, alkaline earth metal salts, such as, for example, calcium and magnesium salts, and salts with organic or inorganic acid, such as, for example, hydrochloric acid, hydrobromic acid, nitric acid, sulfuric acid, phosphoric acid, citric acid, formic acid, maleic acid, succinic acid, tartaric acid, methansulphonic acid, and toluenesulphonic acid, etc.

The term "solvates" includes hydrates or solvates wherein solvents other than water are involved such as, for example, organic solvents like chloroform and the like.

The concentration of the active drug substance in a matrix composition depends on the specific active drug substance, the disease to be treated, the condition of the patient, the age and gender of the patient, etc. The above-mentioned active drug substances are well-known active drug substances, and a person skilled in the art will be able to find information as to the dosage of each active drug substance and, accordingly, he will know how to determine the amount of each active drug substance in a matrix composition.

The active drug substance may be a new chemical entity for which the amount of information is limited. In such cases, the dosage regimen has to be evaluated based on available preclinical and/or clinical data.

The active drug substance may be included in the matrix composition at a concentration amount of from 0.01-99% w/w such as, for example, from 0.01 to 90% w/w, from 0.01 to 80% w/w, from 0.01 to 70% w/w, from 0.01 to 50% w/w, or from 0.01 to 40% w/w. The specific embodiments the drug substance is included in the matrix composition at a concentration of from 10 to 55% w/w.

In one or more embodiments, the active drug substance is a pharmaceutically active powder. Where the drug substance is provided as powder composition, the powder typically have a particle size of from 0.1 µm to 500 µm, typically from 0.5 µm to 300 µm, more typically from 1 µm to 200 µm, especially from 5 µm to 100 µm.

In one or more embodiments, the active drug substance is crystalline. Where included as a crystalline material, the drug substance can exhibit a particle size of from 0.1 µm to 1000 µm such as, for example, 0.1 µm to 750 µm, 0.1 µm to 500 µm, typically from 0.5 µm to 500 µm, more typically from 1 µm to 500 µm, especially from 5 µm to 500 µm.

In one or more embodiments, a matrix composition comprises active drug substance that at least partially present in amorphous form with a mean particle size of at least 0.01 µm such as, for example, from 0.01 µm to 500 µm, from 0.05 µm to 500 µm, from 0.1 µm to 500 µm, from 0.5 µm to 500 µm, 1 µm to 500 µm, typically from 0.5 µm to 300 µm, from 1 µm to 200 µm, or from 1 µm to 100 µm.

A pharmaceutical composition with a matrix composition containing an active drug substance is typically for oral administration. Due to the possibility of controlling the release rate of the active drug substance, the pharmaceutical composition may be adapted for oral administration 1-6 times a day, such as 1-4 times daily, including 1-3 times, 1-2 times or 1 times daily. The technology may also provide pharmaceutical compositions for administration only once or twice daily.

Pharmaceutically Acceptable Excipients

The pharmaceutical composition may also contain other excipients as well, for example in order to improve the technical properties of the pharmaceutical composition so that it may be easier to produce or in order to improve the properties of the pharmaceutical composition such as release rate of the active drug substance, stability of the active drug substance or of the pharmaceutical composition itself.

A suitable pharmaceutically acceptable excipient for use in a pharmaceutical compositions described herein may be selected from fillers, diluents, disintegrants, glidants, pH-adjusting agents, viscosity adjusting agents, solubility increasing or decreasing agents, osmotically active agents and solvents.

Suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), molasses, panwar gum, ghat gum, mucilage of isapol husk, carboxymethylcellulose, methylcellulose, veegum, larch arabolactan, polyethylene glycols, ethylcellulose, water, alcohols, waxes, polyvinylpyrrolidone such as, for example, PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulfate, Sodium laurilsulfate, Stearyl alcohol, Polysorbate 20, Polysorbate 60, Polysorbate 80, Macrogol stearate, Macrogol lauryl ether, Stearoyl macrogolglycerides, Sorbitan stearate, Sorbitan laurate, Macrogol glycerol hydroxystearat, colloidal silicon dioxide and mixtures thereof, disintegrants such as starches, clays, cellulose derivatives including microcrystalline cellulose, methylcellulose, carboxymethylcellulose calcium, carboxymethylcellulose sodium, cellulose, crosscarmellose sodium, gums, aligns, various combinations of hydrogencarbonates with weak acids (e.g. sodium hydrogencarbonate/tartaric acid or citric acid) crosprovidone, sodium starch glycolate, agar, alginic acid, calcium alginate, sodium alginate, chitosan, colloidal silicon dioxide, docusate sodium, guar gum, low-substituted hydroxypropyl cellulose, hydroxypropyl starch, magnesium aluminium silicate, polacrilin potassium, povidone, sodium starch glycolate, pregelatinized starch, cation exchange resins, citrus pulp, veegum, glycollate, natural sponge, bentonite, sucralfate, calcium hydroxyl-apatite or mixtures thereof, effervescent agents (carbonate release) such as citric acid, anhydrous, citric acid, monohydrate, dextrates, fumaric acid, potassium bicarbonate, sodium bicarbonate, sodium citrate, dehydrate, tartaric acid or mixtures thereof.

The matrix composition may comprise one or more gelling agents. The term "gelling agent" as used herein refers to any substance, which is capable of providing the texture of a gel, when added to a liquid solution. Suitable gelling agents may be selected from, for example: polymers selected from modified or unmodified water soluble natural polymer, such as glucomannan, galactan, glucan, polygalacturonic acid, polyxylane, polygalactomannans, polyxyloglycan, arabinogalactan, starch, cellulose, chitosan, alginate, fibrin, collagen, gelatin, amylopectin, pectin including low methylated or methoxylated pectins, dextran; synthetic polymers such as PVA and PVB; and hydrogels made from the polymers or combined polymers mentioned above and or from polymers originated from HEMA, HEEMA, MEMA, MEEMA, EDGMA, NVP, VAc, AA, acrylamide, MAA, HPMA, PEGA, PEGMA, PEGDMA, PEGDA, and/or PEGDMA, hydroxypropyl methylcellulose, hydroxypropyl cellulose, methylcellulose, hydroxyethyl cellulose, ethylcellulose, hydroxypropyl methylcellulose phthalate, hydroxypropyl methylcellulose Acetate Succinate or other cellulose derivates, carboxymethylcellulose sodium, carboxymethylcellulose calcium, carrageenans, guar gum, gellan gum, xanthan gum, tragacanth and Arabic gum.

Furthermore, the pharmaceutical composition may comprise one or more agents selected from sweetening agents, flavouring agents and colouring agents, in order to provide an elegant and palatable preparation. Examples of such agents include, for example, maltol, citric acid, water soluble FD&C dyes and mixtures thereof with corresponding lakes and direct compression sugars such as Di-Pac from Amstar. In addition, coloured dye migration inhibitors such as tragacanth, acacia or attapulgite talc may be added. Specific examples include Calcium carbonate, 1,3,5-trihydroxybenzene, Chromium-cobalt-aluminium oxide, ferric ferrocyanide, Ferric oxide, Iron ammonium citrate, Iron (III) oxide hydrated, Iron oxides, Carmine red, Magnesium carbonate and Titanium dioxide.

Plasticizer may be incorporated in the matrix composition and/or in the shell. Suitable plasticizer may be selected from, for example: mono- and di-acetylated monoglycerides, diacetylated monoglycerides, acetylated hydrogenated cottonseed glyceride, glyceryl cocoate, Polyethylene glycols or polyethylene oxides (such as, for example, with a molecular weight of 1,000-500,000 daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, dibutyl sebacate, Castor oil, acetyl tributyl citrate, acetyl triethyl citrate, methyl abietate, nitrobenzene, carbon disulfide, β-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols, nitrobenzene, carbon disulfide, β-naphtyl salicylate, phthalyl glycolate, dioctyl phthalate and mixtures thereof.

Chemical stabilizers that may be included in the matrix composition include TPG, for example, in the form of TPGS, BHA, BHT, t-butyl hydroquinone, calcium ascorbate, gallic acid, hydroquinone, maltol, octyl gallate, sodium bisulfite, sodium metabisulfite, tocopherol and derivates thereof, citric acid, tartaric acid, and ascorbic acid. Other stabilisers include trivalent phosphorous, such as, for example, phosphite, phenolic antioxidants, hydroxylamines, lactones such as substituted benzofuranones. Hindered phenols, thiosynergists and/or hindered amines, acids (ascorbic acid, erythorbic acid, etidronic acid, hypophosphorous acid, nordihydroguaiaretic acid, propionic acid etc.), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate. However, other anti-oxidative agents known in the art may be used according in the matrix compositions. Other suitable stabilizers may be selected from, for example, sorbitol glyceryl tricitrate and sucrose octaacetate.

A release modifier may be incorporated in the matrix composition. A suitable release modifier may be selected from, for example, fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glyceryl cocoate, oleyl alcohol, myristyl alcohol, sucrose octaacetate, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose, cellulose acetate, polylactic acid or polyglycolic acid and copolymers thereof, methacrylates, a co-polymer of methacrylate-galactomannan, Polyvinyl alcohols, glycerinated gelatin and cocoa butter.

Other suitable release modifiers may be selected from inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

Alternatively or additionally, mono-, di-, oligo, polycarboxylic acid or amino acids may be included as a pharmaceutically acceptable excipient in the matrix compositions described herein. Examples of such excipients include, for example, acetic acid, succinic acid, citric acid, tartaric acid, acrylic acid, benzoic acid, malic acid, maleic acid, sorbic acid, aspartic acid and glutamic acid.

Examples of suitable organic acids that may be used in the matrix compositions described herein include acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, and pyruvic acid. Examples of suitable inorganic acids that may be used in the matrix compositions described herein include pyrophosphoric, glycerophosphoric, phosphoric such as ortho and meta phosphoric, boric acid, hydrochloric acid, and sulfuric acid.

Inorganic compounds may be included in the matrix compositions described herein. An example of a suitable inorganic compound is aluminium.

Organic bases may be included in the matrix compositions described herein. Examples of organic bases are p-nitrophenol, succinimide, benzenesulfonamide, 2-hydroxy-2cyclohexenone, imidazole, pyrrole, diethanolamine, ethyleneamine, tris (hydroxymethyl) aminomethane, hydroxylamine, sodium citrate, aniline or hydrazine.

Inorganic bases may be included in the matrix compositions described herein. Examples of inorganic bases include aluminium oxide, such as, for example, aluminium oxide trihydrate, alumina, sodium hydroxide, potassium hydroxide, calcium carbonate, ammonium carbonate or ammonium hydroxide.

Salts of an organic acid may be included in the matrix compositions described herein. Suitable pharmaceutically acceptable salts of an organic acid include, for example, an alkali metal salt or an alkaline earth metal salt such as, for example sodium phosphate, sodium dihydrogenphosphate, disodium hydrogenphosphate, potassium phosphate, potassium dihydrogenphosphate, potassium hydrogenphosphate, calcium phosphate, dicalcium phosphate, sodium sulfate, potassium sulfate, calcium sulfate, sodium carbonate, sodium hydrogencarbonate, potassium carbonate, potassium hydrogencarbonate, calcium carbonate, magnesium carbonate, sodium acetate, potassium acetate, calcium acetate, sodium succinate, potassium succinate, calcium succinate, sodium citrate, potassium citrate, calcium citrate, sodium tartrate, potassium tartrate or calcium tartrate.

Inorganic salts may be included in the matrix compositions described herein. A suitable inorganic salt for use in a matrix composition may be sodium chloride, potassium chloride, calcium chloride or magnesium chloride.

Saccharides may be included in the matrix compositions described herein. Suitable saccharides may be selected from, for example, glucose, ribose, arabinose, xylose, lyxose, xylol, allose, altrose, inosito, glucose, sorbitol, mannose, gulose, Glycerol, idose, galactose, talose, mannitol, erythritol, ribitol, xylitol, maltitol, isomalt, lactitol, sucrose, fructose, lactose, dextrin, dextran, amylose, xylan.

Polyethylene glycol derivatives may be included in the matrix compositions described herein. Suitable polyethylene glycol derivatives may be selected from, for example, polyethylene glycol di(2-ethyl hexoate), polyethylene glycols (200-600 daltons) or polyethylene oxides, for example with a molecular weight of 900-300,000 daltons.

Cellulose and cellulose derivatives may be included in the matrix compositions described herein. Cellulose and cellulose derivatives suitable for use in the matrix composition may be selected from methylcellulose, carboxymethylcellulose and salts thereof, microcrystalline cellulose, ethylhydroxyethylcellulose, ethylcellulose, cellulose acetate, cellulose proprionate, cellulose nitrate, cellulose acetate phthalate, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose.

Preparation of a Pharmaceutical Composition

In some embodiments, the reinforcement elements mentioned above may be molded or extruded together with the shell wall in one process. In such an embodiment, the injection mold, or extrusion die is built in the proper shape to assure the desired dimensions of shell wall and reinforcement elements. If the reinforcement element is not the same material as the outer shell wall, the pharmaceutical composition may be manufactured using a multi-part process. For example, such a process may include a 3 component extrusion/injection moulding ($1^{st}$ outer shell wall; $2^{nd}$ reinforcement element(s); $3^{rd}$, matrix composition). Where a multi-extrusion process is employed, the order in which the different components are extruded may be arranged as desired to provide a finished dosage form.

In specific embodiments, where the shell wall is configured to extend from a first end to a second end along a first axis, reinforcement walls perpendicular to the first axis can be injection molded. For such embodiments, the injection mold is built in the proper shape, to assure the dimensions of the outer shell wall and reinforcement wall. If the reinforcement wall is not the same material as the outer shell wall, the pharmaceutical composition may be manufactured using a multi-step process. For example, such a process may include a 3 component injection molding ($1^{st}$ outer shell wall; $2^{nd}$ reinforcement element(s); $3^{rd}$, matrix composition). Where a multi-part injection molding process is employed, the order in which the different components are extruded may be arranged as desired to provide a finished dosage form.

The matrix composition may also be extruded or molded and subsequently put into a weave for wrapping a mesh of fiber thread around the matrix core. The fiber thread is warmed into the matrix composition by means of a heating gun, or moulded directly into the matrix, and finally wound-up for cooling. When the fiber thread has been wrapped around the matrix composition, depending on shape, the shell composition may be co-extruded or molded over the matrix composition.

The pharmaceutical composition, as well as the matrix composition and shell composition described herein, may also be produced by various other methods which are either known in the pharmaceutical industry or which, for example, are used in the production of polymer-based materials. The process used to manufacture a pharmaceutical composition as described herein will depend upon the desired embodiment and the materials employed in the pharmaceutical composition in question. An advantage pharmaceutical compositions described herein is that they may be produced by methods, which are relatively simple and inexpensive.

Suitable preparation methods for pharmaceutical compositions described herein include extrusion, injection moulding, tabletting, capsule filling, thermoforming, melt-processing, spray coating, micro encapsulation and other methods of preparing controlled release pharmaceutical compositions. Also, a combination of one or more of the aforementioned may be employed.

The controlled release pharmaceutical composition may be prepared by several different methods. Many systems for controlled release are marketed and it is currently an aim for the industry to reduce the risk of dose dumping, drug abuse or alcohol induced dose dumping in each of the systems.

Pharmaceutical compositions for controlled release according to the invention may be prepared in numerous ways giving rise to different release mechanisms. Particularly, the pharmaceutical compositions described herein may be prepared by 1, 2 or multiple component injection mouldings, by conventional tablet compression, by micro encapsulation, by 1, 2 or multiple component extrusions, by capsule filling, by thermoforming or by melt-processing. In cases where a preparation is needed in order to make the controlled release properties before/after the above mentions preparation steps, the preparation may also comprise separate steps, such as, for example, wet granulation, dry granulation, melt granulation, pelletizing, spray coating, electrostatic coating or other methods for preparing controlled release dosage forms.

In a particular example, the pharmaceutical composition is prepared by two component injection moulding of a matrix composition and a shell surrounding the matrix and exposing at least one surface of the matrix, preferably the two ends of the matrix composition for erosion governed release.

A pharmaceutical composition may also be produced by, for example, injection moulding, co-extrusion of the shell with the matrix composition and the active drug substance, extrusion and dip coating, injection moulding and dip coating, or by extrusion or injection moulding and solvent coating by spraying or dipping, multiple component injection moulding, or a combination of these methods.

Pharmaceutical Compositions

In specific embodiments, the pharmaceutical composition according to the present invention comprises: an active drug substance selected from morphine, oxycodone, hydrocodone, hydromorphone, norhydrocordone, oxymorphone, noroxycodone, morphine-6-glucuronide and pharmaceutically acceptable salts thereof, such as morphine sulphate, morphine sulphate pentahydrate, oxycodone hydrochloride, hydromorphone hydrochloride and hydrocodone bitartrate; a matrix comprising at least one of polyglycol selected from polyethyleneglycol and polyethylene oxide and any mixtures thereof, at least one block copolymer which is poloxamer, at least one pharmaceutical excipients selected from mannitol, butylated hydroxytoluene and Vitamin E Polyethylene Glycol Succinate, Eudragit L, Eudragit RL, Eudragit RS, Eudragit E, Eudragit S, and at least one gelling agent selected from carrageenan and hydroxypropylmethylcellulose; and a shell selected from ethyl cellulose, cetostearyl alcohol and titanium dioxide or polylactic acid and polyethylene oxide.

In specific embodiments, the pharmaceutical composition according to the present invention comprises: an active drug substance selected from morphine, oxycodone, hydrocodone, hydromorphone, norhydrocordone, oxymorphone, noroxycodone, morphine-6-glucuronide and pharmaceutically acceptable salts thereof, such as morphine sulphate, morphine sulphate pentahydrate, oxycodone hydrochloride, hydromorphone hydrochloride and hydrocodone bitartrate; at least one opioid antagonist which is Naltrexone; at least one polyglycol selected from polyethyleneglycol and polyethylene oxide and any mixtures thereof; at least one block copolymer which is poloxamer; at least one pharmaceutical excipient selected from mannitol, butylated hydroxytoluene and Vitamin E Polyethylene Glycol Succinate, Eudragit L, Eudragit RL, Eudragit RS, Eudragit E, Eudragit S; and at least one gelling agent selected from carrageenan and hydroxypropylmethylcellulose; and a shell selected from ethyl cellulose, cetostearyl alcohol and titanium dioxide or polylactic acid and polyethylene oxide.

Other Aspects

Dose Dumping

Pharmaceutical compositions described herein are particularly suited for providing controlled release pharmaceutical compositions containing a matrix composition comprising a) polymer or a mixture of polymers, b) an active drug substance and optionally c) one or more pharmaceutically acceptable excipients; the matrix composition being provided with a shell (coating). In specific embodiments, the matrix compositions and shell included in the pharmaceutical compositions described herein may be formulated and configured such that the pharmaceutical composition does not exhibit alcohol-induced dose dumping. In such embodiments, the matrix composition exhibits a solubility and/or drug substance release rate in alcohol containing media (e.g., ethanol containing media) that is lower than or equal to the solubility and/or release rate in aqueous media that does not include alcohol (e.g., water, phosphate buffer medium pH 6.8 or hydrochloride solution pH 1.2). In some such embodiments, the polymers and excipients chosen for use in the matrix composition are selected and provided in relative amounts that result in an unchanged or lower dissolution rate and/or release rate of the drug substance in alcohol containing media (e.g., ethanol containing media) as compared to the solubility and/or release rate exhibited in aqueous media that does not include alcohol (e.g., water, phosphate buffer medium pH 6.8 or hydrochloride solution pH 1.2). In certain such embodiments, the dissolution and/or release rate of the drug substance from the matrix composition in alcohol containing media (e.g., ethanol containing media) is at least 1.25 times lower, such as at least 1.5 times lower, at least 2 times lower, such as 5 times, 10 times, 25 times, 50 times, or 100 times lower than the dissolution and/or release rate of the drug substance in aqueous media that does not include alcohol (e.g., water, phosphate buffer medium pH 6.8 or hydrochloride solution pH 1.2).

More specifically, the invention may provide a matrix composition of i) a polymer and ii) an active drug substance, which pharmaceutical composition mitigates or eliminates alcohol-induced dose dumping. Typically, the solubility or release rate of the matrix composition is lower or substantially the same in alcohol than that in water. More specifically, the solubility or release is equal or at least 1.25 times lower such as at least 1.5 times lower, at least 2 times lower in alcohol than in water, notably 5 times, 10 times, 25 times, 50 times or 100 times lower.

Encapsulation of the Active Drug Substance to Prevent Abuse of a Pharmaceutical Composition According to the Invention Another approach to making pharmaceutical compositions resistant to abuse is to modify the physical-chemical properties of the active drug substance in such a way that the bioavailability of the active drug substance in the GI tract is determined not only by the controlled release mechanism of the pharmaceutical compositions, but also by the solubility and/or absorption characteristics. This is, in effect, to include a second controlled release mechanism in conjunction with the pharmaceutical compositions in such a way that the overall release pattern in vitro is conserved even after physical tampering.

An abuse resistant pharmaceutical composition has been developed with the objective of reducing the likelihood of tampering and/or improper administration of pharmaceutical composition, such as, for example, a pharmaceutical composition for the delivery of opioids. A controlled release pharmaceutical composition may be provided in the form of microcapsules, wherein release of the active drug substance is controlled by the solubility of the active drug substance and/or release controlled by matrix microstructure.

In particular embodiments, the release profile of the drug substance may be modified by means of encapsulation or microencapsulation of the active drug substance in a lipophilic environment. In such embodiments, the encapsulated active drug substance is dispersed in a hydrophilic matrix consisting of polymeric systems, such as, for example, PEG/PEO and poloxamers.

The encapsulated active drug substance may be coated with one or more layers of coating which is degradable in the GI tract. The abuse-deterrent features of such a pharmaceutical composition will ensure that the physical release characteristics of the active drug substance are not compromised even if the matrix is compromised by, for example, crushing, chewing or grinding. If the pharmaceutical composition is taken as prescribed, the active drug substance will release as intended by means of erosion, surfactant action and degradation in the GI tract.

Encapsulation is a well-known technology, and has been commercially applied in the taste masking of products in, for example, the food industry. There are a number of techniques such as fluid bed coating, pan coating, chemical encapsulation and other techniques, which could be used in the encapsulation of a specific active drug substance.

In some embodiments, a pharmaceutical composition as described herein may include a hydrophilic matrix, which is advantageous in preventing alcohol induced dose dumping, combined with a hydrophobic microenvironment around the active drug substance, which is advantageous in preventing abuse of active drug substance by means of manipulating the matrix.

Once the active drug substance has been modified by means of encapsulation, the resulting matrix composition is blended and used in the conventional manufacturing process for example injection moulding.

Naltrexone and/or Other Opioid Antagonists and/or any Type of Aversive Agents

Naltrexone (see chemical formula below), marketed as naltrexone hydrochloride, is an opioid receptor antagonist (antidote). Naltrexone is used primarily in the management of alcohol dependence and opioid dependence.

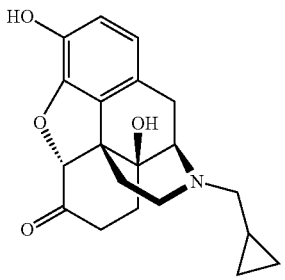

Naltrexone does not possess a biological response itself upon binding to a receptor, but blocks or dampens agonist-mediated responses. It works by binding to the active site or to allosteric sites on receptors, or they may interact at unique binding sites not normally involved in the biological regulation of the receptor's activity. Thereby, Naltrexone will occupy the active site, which otherwise would have been a vacant receptor site for the opiod.

Partial agonists may also be applicable for incorporation in the pharmaceutical compositions described herein. Partial agonists (such as buspirone, aripiprazole, buprenorphine, or norclozapine) bind and activate a given receptor, but have only partial efficacy at the receptor relative to a full agonist. They may also be considered ligands which display both agonistic and antagonistic effects—when both a full agonist and partial agonist are present.

Naltrexone and/or other similar antagonists of the opioid receptor can be used to prevent abuse of opioids. More specifically, when a pharmaceutical composition that includes Naltrexone and/or one or more other, similar antagonists is subjected to physical tampering, the Naltrexone and/or similar antagonists will be released along with the opioid, thereby hindering the opioid effect. In such formulations, the Naltrexone and/or other similar antagonists are incorporated in the pharmaceutical composition in a way that prevents release of the antagonist as long as the pharmaceutical composition remains intact and it is administered as intended. Thus, it will not interfere with the opioid/pain relieving effect expected by the patients when used according to the recommendation.

As an alternative or in addition to one or more antagonists, such an opioid antagonist, an aversive agent can be added to the pharmaceutical composition. These agents are added to provide, for example, an irritant and/or painful stimulus and/or bad taste and/or any other form of discomfort if the dosage form is subjected to physical tampering or other conditions associated with abuse. As is true of antagonists, the aversive agents should only be released if attempts are made to use the pharmaceutical composition in a manner different than intended.

The Naltrexone and/or other similar antagonists and/or any type of aversive agents in the pharmaceutical composition may be:

Embedded in a matrix composition as coated particles or other physical forms with a water-resistant surface coating.

Embedded in a shell composition either internally of externally; and/or

Provided around the shell and/or matrix or otherwise added to the pharmaceutical composition to prevent effect of tampering and abuse.

Such a pharmaceutical composition may have an inner core containing antagonist/aversive agent(s), wherein the antagonist/aversive agent(s) is embedded between a first reinforcement wall and a second reinforcement wall with no openings. In such an embodiment the first and second reinforcement walls are impermeable under normal use conditions, ensuring no release of the antagonist/aversive agent from an intact pharmaceutical composition. In such an embodiment the first and second reinforcement wall can take on any configuration, and the matrix formulation and shell may be configured as desired.

Figure 11:
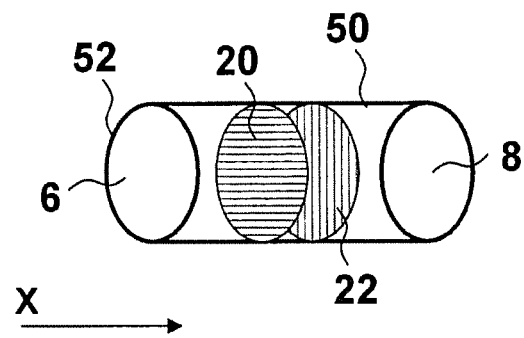

In FIG. 11, a pharmaceutical composition 50 comprises a shell 52 forming a number of cavities for accommodating a matrix composition. Antagonist/aversive agent(s) is embedded between a first reinforcement wall 20 and a second reinforcement wall 22, which has no openings (impermeable) and, thereby, ensures no release of the antagonist/aversive agent release from an intact pharmaceutical composition. The outer shell wall 52, the first reinforcement wall 20, and the second reinforcement wall 22 form a closed cavity enclosing the antagonist/aversive agent. The first reinforcement wall 20 and the second reinforcement wall 22 are perpendicular to the first axis X.

Figure 12:
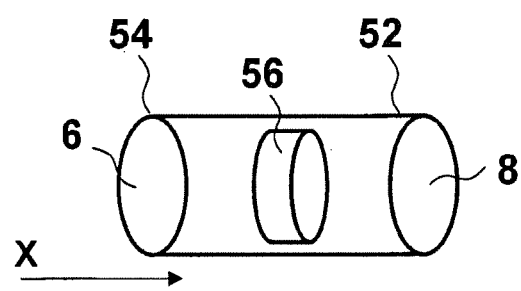

FIG. 12 schematically illustrates a pharmaceutical composition 54 comprising a shell 52 with an opening at the first end and the second end, respectively, where the pharmaceutical composition comprises an inner core 56 enclosing an antagonist/aversive agent. The inner core is positioned in the cavity formed by the shell 52 and can take any shape or form, such as, for example, round, cylindrical, oval and triangular. The inner core may be either randomly placed in the cavity or fixed at a certain position. The inner core 56 may have a shell/coating preventing release of the antagonist/aversive agent. If the pharmaceutical composition 54 is subject to physical tampering, for example by crushing, heating, or other means, the shell/coating of the inner core 56 breaks and the antagonist/aversive agent is released and mixed with the active drug substance, thereby mitigating or preventing abuse.

In particular embodiments, the pharmaceutical composition may comprise a matrix composition comprising coated particles containing antagonist/aversive agent(s). As illustrated in FIG. 13A, the pharmaceutical composition 54' comprises a number of coated particles 58 embedded in the matrix composition accommodated in the shell 52. For example, a number of coated particles, such as coated particles 58, may be embedded in a matrix composition such as those as shown in FIG. 8, shell 2, 102, 202, 302, 402, 502, 602; FIG. 9, shell 702; and FIG. 10, shell 802; where the coating on the coated particle 58 ensures that no antagonist/aversive agent is released from an intact pharmaceutical composition. The particles 58 can take any shape or form i.e. round, cylindrical, oval and/or triangular.

In particular embodiments, the pharmaceutical composition may comprise a matrix composition comprising one or more tubes optionally with closed ends, with the one or more tubes enclosing an antagonist/aversive agent(s). As illustrated in FIG. 13B, the pharmaceutical composition 54" comprises a tube 60 embedded in the matrix composition accommodated in the shell 52, for example shell, 2, 102, 202, 302, 402, 502, 602, 702, 802, where the tube 60 ensures that no or limited amount of antagonist/aversive agent is released from an intact pharmaceutical composition.

The pharmaceutical compositions as described herein may comprise antagonist/aversive agent(s) in shell composition or in chambers in the shell construction which ensures that no antagonist/adversive agent is released from an intact pharmaceutical composition. These chambers can either partly or entirely surround the matrix composition.

The pharmaceutical composition may have antagonist/aversive agent(s) surrounding the matrix composition internally. In such an embodiment, the shell ensures that no antagonist/aversive agent is released from an intact pharmaceutical composition. This antagonist/aversive agent chambers can be either partly or entirely surrounded by the matrix composition and can take any form as part of the interior of the pharmaceutical composition.

The pharmaceutical composition may comprise a grid comprising antagonist/aversive agent(s) as illustrated in FIG. 13C. In such case the active drug substance may be released through the grid having a hollow grid structure containing antagonist/aversive agent(s), which can only be released upon tampering with the pharmaceutical composition. Alternatively, the antagonist/aversive agent(s) containing grid can either fully or partly surround the pharmaceutical composition.

The antagonist/aversive agent(s) may be coated and or imbedded in the pharmaceutical composition in such a way that the antagonist/aversive agent is not released when the pharmaceutical composition is administered as intended. The antagonist/aversive agent included in such a composition should be released when the pharmaceutical composition is tampered and is physically changed from its intended form. The amount of antagonist/aversive agent(s) in the pharmaceutical composition is sufficiently high to prevent an abuser in getting a "high" when the pharmaceutical composition is tampered with and the intended release mechanism is compromised. The antagonist/aversive agent(s) of an intact pharmaceutical composition will pass through the gastrointestinal tract to be excreted in faeces. Alternatively, where the pharmaceutical composition is administered as intended, antagonist/aversive agent(s) contained therein can be otherwise hindered in exerting an effect, such as by enzymatic interaction.

In the case of opioids, an antagonist may prevent an abuser from achieving a "high". The antagonist or aversive agent can be any agent that negates the effect of the therapeutic agent or produces unpleasant or punishing stimulus or effect, which will deter or cause avoidance of tampering with the pharmaceutical compositions comprising the same. Desirably, the antagonist/aversive agent does not harm the abuser by its administration or consumption but has properties that deter its administration or consumption if the controlled release mechanism as intended is altered, such as by chewing and swallowing or by crushing and snorting. The antagonist/aversive agent can, for example, have a strong or foul taste or smell, provide a burning or tingling sensation, cause a lachrymation response, nausea, vomiting or any other unpleasant or repugnant sensation or color. The antagonist/aversion agent is selected from antagonists of a therapeutic agent, a bittering agent, a dye, a gelling agent and an irritant.

Examples of suitable irritants may be of natural or synthetic origin and include, for example, mustard, allyl isothiocyanate and p-hydroxybenzyl isothiocyanate; capsaicinoids, such as, for example, capsaicin, dihydrocapsaicin, nordihydrocapsaiscin, homocapsaicin, and homodihydrocapsaicin; mint; aspirin; and acids such as, for example, acids with one or more carboxyl moieties, such as, for example, formic acid, acetic acid, propionic acid, butyric acid, valeric acid, caproic acid, caprillic acid, capric acid, oxalic acid, malonic acid, succicnic acid, glutaric acid, adipic acid, maleic acid, fumaric acid, and citric acid. In one or more embodiments, local irritants for use as aversive agents are capsaicinoids, such as, for example, capsaicin.

In one or more embodiments, the pharmaceutical composition may include one or more mucous membrane irritants as aversive agents that cause irritation of mucous membranes located anywhere on or in the body, including membranes of the mouth, eyes, nose and intestinal tract. Such pharmaceutical compositions can deter abuse via oral, intra-ocular, rectal, or vaginal routes. The above-described irritants can be further optimized as necessary or desired in terms of for example concentration and irritation severity. In particular embodiments, the surfactant can be an anionic surfactant. In one such embodiment, an anionic surfactant (for example, docusate) can also function as a potential laxative and/or stool softener at excess doses.

Examples of other aversive agents include derivatives or complexes, pharmaceutically acceptable salts, and combinations of benzoic benzylamine amide, denatonium benzoat alkaloids, amino acids, trichloro anisole, methyl anthranilate, quinine, denatonium saccharide, denatonium chloride, sucrose octaacetate, quassinoids, such asquassin or brucine, flavenoids, such as quercetin or naringen, resinferatoxin, piperine, allyl isothiocyanate and/or niacine.

In the instance when the therapeutic agents is an opioid agonist, suitable antagonists include: derivatives or complexes, pharmaceutically acceptable salts and/or combinations of naltrexone, methoxy-naltrexone, naloxone, naloxone methiodide, phenylhydrazone derivatives, nalmefene, cyclazine, nalorphine, levallorphan; peptides derived from lactoferrin; selective sub-type opioid receptor antagonists, such as cyprodime, naltrindole, norbinaltorphamine, D-Pen$^2$, D-Pen$^5$]enkephalin and derivatives thereof; and/or peptides derived from lactoferrin and or partial agonist also having opioid antagonist properties exemplified by buprenorphine. In specific embodiments, the opioid antagonist is naloxone or naltrexone. "Opioid antagonist" refers to one or more opioid antagonists, either alone or in combination, and further includes partial antagonist, pharmaceutically acceptable salts thereof, stereoisomers thereof, ethers thereof, esters thereof and combinations thereof. The antagonist or aversive agent may comprise of a single type of antagonist and/or aversive agent, or a combination of different types of antagonists and aversion agents.

Protocol on Tampering Methods

Figure 14:
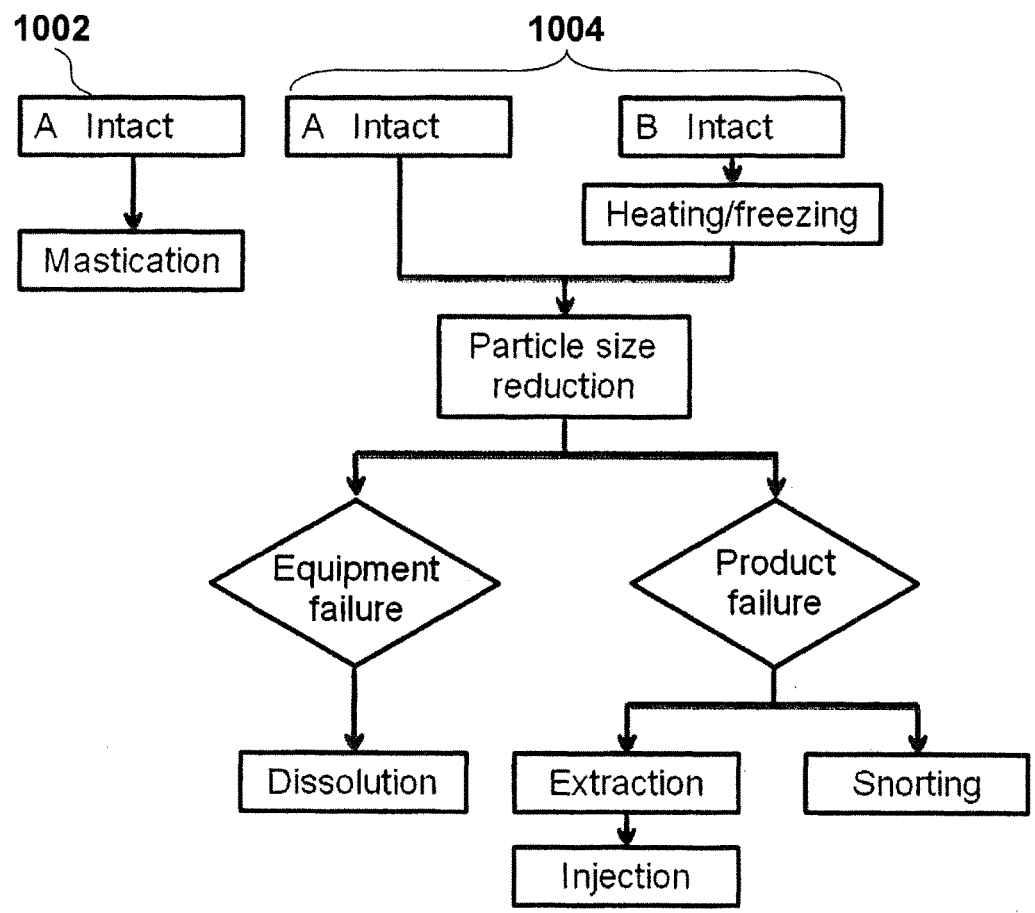
FIG. 14 illustrates a flow chart of tampering methods.

A series of methods have been developed to illustrate the pharmaceutical composition extent of being abuse resistant. The methods are based on the in vitro test shown in the flow chart of FIG. 14.

Two separate paths are shown in the flow chart. The first path 1002 entails a buccal & mastication method/test to evaluate abuse potential when intact pharmaceutical compositions are subjected to chewing. The second path 1004 entails a particle size reduction test method to evaluate abuse potential when the pharmaceutical composition is subjected to physical and/or chemical tampering. Both intact pharmaceutical compositions (compositions that have not been subjected to tampering) and pharmaceutical compositions subjected to tampering, such as by, for example, freezing, microwaving, burning and melting are subjected to particle size reduction. Provided that the pharmaceutical compositions do not change release profile of the active drug substance subsequent to this test, the test program is successfully completed, indicating a dosage form that is resistant to abuse. Tests on pharmaceutical compositions subjected to tampering or may also result in equipment failure, and in such an instance, the test program is considered successfully completed, indicating a dosage form that is resistant to abuse.

If a given pharmaceutical composition is crushed or broken into small pieces or small particles, an increased exposed surface area is created, which increases release rate of the active drug substance. Such an increase in release rate may lead to an increased potential for abuse. If a change in the release profile of the active drug substance is noticed, the pharmaceutical composition is considered to have failed. At such a point, it is the potential for abusing the compromised pharmaceutical composition, such as by snorting or chemical extraction, is evaluated. If the active drug substance can be extracted from the compromised pharmaceutical composition, the ease with which such extracted drug substance can be injected is evaluated.

Tampered by Freezing

The purpose of the freezing test is to evaluate if freezing is a suitable technique for defeating the controlled release mechanism of the pharmaceutical compositions. Furthermore, the purpose is to evaluate whether freezing results in a brittle pharmaceutical composition and/or shell.

Figure 15:
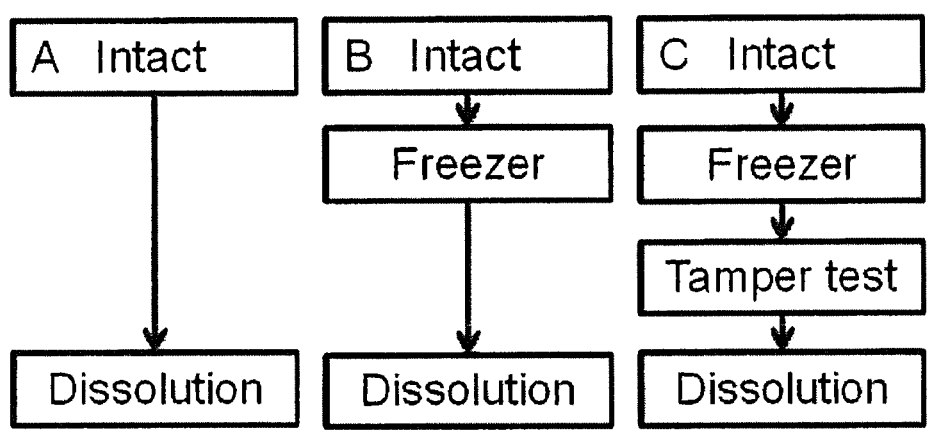
FIG. 15 illustrates a freezing test program for a pharmaceutical composition.

The freezing test program is shown in FIG. 15. The dissolution tests can be used to evaluate if the controlled released mechanism in the frozen pharmaceutical compositions (i.e., freeze tampered) has been defeated. The freezing test can be conducted by test A, B and C. The dissolution tests can be performed as described in the section describing dissolution testing.

Test A: Perform a dissolution test on intact pharmaceutical compositions such as tablets (e.g., n=3). The results from test A are defined as control data. Test B: Place, for example, 3 pharmaceutical compositions/tablets in a freezer (−18° C.) for a predetermined period of time, such as approximately 24 hours. Perform a dissolution test on the freeze tampered tablets. Test C: Place, for example, 3 tablets in a freezer (−18° C.) for approximately 24 hours. Place the tablet in a plastic bag and fold the bag around the tablet a least three times to avoid escape of the tablet. Strike the tablet with a hammer until the tablet is broken, if possible. Perform a dissolution test on the freeze tampered tablets.

Microwave Tampering

The purpose of the heating test is to evaluate if thermal manipulation by heating in a microwave oven is a suitable technique for defeating the controlled release mechanism in the pharmaceutical compositions.

Figure 16:
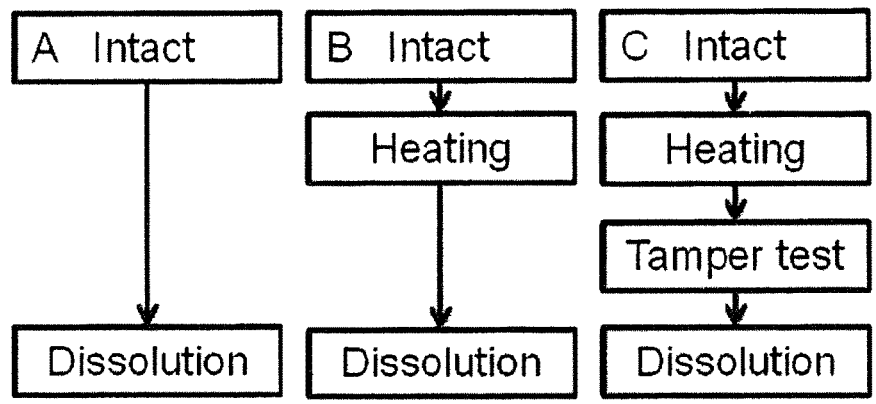
FIG. 16 illustrates a heating test program (e.g. microwave, burning and melting) for a pharmaceutical composition.

The heating test program is shown in FIG. 16. The microwave effect can be based on several tests conducted in a microwave oven in order to establish knowledge on thermal treatment of the pharmaceutical composition for example tablets. It has been shown that heating the tablets two times, each without water for one minute at 800 W is sufficient to heat the entire tablet. Prolonging the time to 2 minutes did not result in increased tablet temperature. After 3 minutes, the over-temperature safeguard in the microwave was activated.

Several tests adding 10 ml up to 100 ml water to pharmaceutical composition (for example, tablets) in different beakers have also been conducted. Relatively large cone-shape flasks (250 ml) were selected, as it then was possible to boil the tablets without bumping. It was found that a 250 ml flask with 30 ml water was most suitable. Small volumes of water resulted in the tablets not being entirely covered by the water, and larger volumes resulted in boiling over in the microwave around 1 minute after start.

The microwave test can be conducted by test A, B and C illustrated in FIG. 16. The Dissolution tests can be performed as described in the section describing dissolution testing to evaluate whether the controlled release mechanism in the heated pharmaceutical composition has been defeated. Test A: Perform dissolution test on intact tablets (e.g. n=3). The results from test A are defined as control data. Test B: Place one tablet in a 250 mL flask. Heat the tablet in a microwave oven for 1 minute and inspect the tablet visually. Perform this heating procedure 3 times, followed by a dissolution test (e.g., n=3). Test C: Place one tablet in a 250 mL flask and add 30 mL water. Heat the tablet in a microwave oven for 1 minute. Survey the flask and stop the microwave if the water is boiling over. Pick up the tablet with a forceps and try to remove matrix from the shell with a spatula. Perform the heating and matrix removal procedure for example 3 tablets. Perform a dissolution test on the tablets (e.g. n=3).

Tampered by Heating/Melting with for Example Gas Burner

The purpose of the heating test is to evaluate if thermal manipulation by heating or melting of the pharmaceutical composition with a gas burner is a suitable technique for defeating the controlled release mechanism in the pharmaceutical composition.

The heating test program is shown in FIG. 16. The burning time chosen is based on preliminary tests with a gas burner, which were conduced in order to establish suitable conditions for the thermal treatment of the pharmaceutical compositions. The gas burner is adjusted to burn at low temperature with blue flame. It was found to be very difficult to heat/melt the tablets without charring the tablets completely. However, it was possible to avoid charring by moving the gas burner slightly back and forth for approximately 5 minutes.

The heating test can be conducted by test A and B, and the Dissolution tests can be performed as described in the section describing dissolution testing to evaluate whether the controlled release mechanism in the heated pharmaceutical composition for example tablets has been defeated. Test A: Perform a dissolution test on intact tablets (e.g. n=3). The results from test A are defined as control data. Test B: Place for example 3 tablets on a large plate. Heat the tablets for approximately 5 minutes while avoiding charring. If possible, turn the tablets approximately each minute. Visually inspect the tablets during heating. Perform a dissolution test on the burned/melted tablets (e.g. n=3)

Tampered by Heating/Melting with for Example Heating Plate

The purpose of this heating test is to evaluate whether thermal manipulation by melting on for example a heating plate is a suitable technique for defeating the controlled release mechanism in the pharmaceutical compositions.

The heating test program is shown in FIG. 16. The temperature and time parameter chosen are based on preliminary tests conducted on a heating plate in order to establish conditions suitable for the thermal treatment of the pharmaceutical compositions. It was found that the temperature should be at least 150° C. before the tablet starts to melt properly. It was decided to heat the intact tablet for around 8 minutes turning the tablet each minute to avoid browning the tablet. Further heating resulted in browning of the surfaces.

The heating test can be conducted by test A and B, and the dissolution tests can be performed as described in the section describing dissolution testing to evaluate whether the controlled release mechanism in the heated pharmaceutical composition has been defeated. Test A: Perform a dissolution test on intact tablets (e.g. n=3). The results from test A are defined as control data. Test B: Place for example 3 tablets on a large petri dish. Heat the tablets for 8 minutes at approximately 180° C. Turn the tablets approximately each minute. Visually inspect the tablets during heating. Perform a dissolution test on the heated tablets (e.g. n=3).

Buccal & Mastication

The method aims to evaluate the abuse potential of active drug substance from pharmaceutical compositions by chewing.

Figure 17:
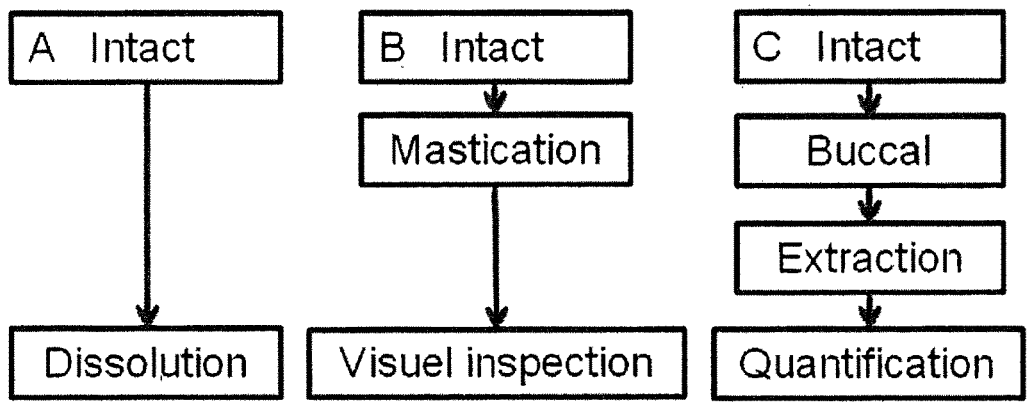
FIG. 17 illustrates a mastication and buccal test program for a pharmaceutical composition.

The mastication and buccal test program is shown in FIG. 17. The chewing test can be carried out using a chewing apparatus which has been developed to determine the release rate of the active drug substance from medicated chewing gum formulations.

A chewing apparatus to perform tests on medicated chewing gum formulation is described in *Chewing apparatus, Ph. Eur* 2.9.25. The basic principle behind the apparatus is a masticatory movement employed to simulate the chewing action on a material, such as gum, placed in a small chewing chamber, where the material is chewed by two horizontal pistons representative of teeth. The teeth are working alternately with a third vertical piston (tongue) at a constant speed. The results have shown that the apparatus can provide strong mechanical forces that influence the release of active drug substance from chewing gum. The apparatus is found interesting as it has the ability to simulate the "grinding" movement of the bite on the tablet when continuously chewed. The apparatus used was from Weissen Born maskinfabrik, Vejle, Denmark.

In principle, the apparatus gives a simple masticatory movement to simulate the chewing action on a piece of material placed in a small chewing chamber containing a known volume of, for example, a buffer solution at 37° C.

In this test, the chewing apparatus is a model system for human chewing of pharmaceutical compositions. The time point chosen in test B is based on experience with hard model chewing gums.

The mastication and buccal test can be conducted as described in test A, B and C. Test A: Perform a dissolution test as described in the section describing dissolution testing on pharmaceutical compositions (e.g. n=3). The results from test A are defined as control data. Test B, Mastication: Place one tablet in the chewing chamber. Start the chewing action and visually inspect the tablet after 1 minute (44 chews), 3 minutes (132 chews) and 5 minutes (220 chews). Note the appearance of the tablet, especially the integrity of the shell. Assessment criteria of the chewing test is operated as described or until equipment failure. Test C, Buccal: Place one tablet in a beaker and add 5 ml artificial saliva. Withdraw 300 µl samples after 10, 30 and 60 minutes.

Transfer the sample to a HPLC vial and add 1 ml phosphate buffer pH 6.8. Analyze the samples as content uniformity (CU). For CU dilute single tablets in 100 ml phosphate buffer 6.8. Dissolve over night. Morphine sulphate as API is determined by reverse phase chromatography, using a LiChroCART 250-4 packed with LiChrospher 100 RP-18, 5 µm column and a LiChroCART 250-4 packed with LiChroCART 4-4 RP-18, 5 µm as pre-column. The mobile phase consists of Acetonitrile:Ammonium acetate buffer (10:90 v/v). The HPLC settings are as follows: Isocratic, column temperature 30° C. flow 1.0 ml/min, detection HPLC-UV at 285 nm, injection volume 20 µl with a run time if 10 minutes. Compare the extracted amount to the data obtained in test A. The extracted amount (in mg) must be evaluated both absolutely and in comparison to the label claim. Furthermore, the amount of active drug substance must be evaluated to determine whether enough was extracted to meet the ultimate goal for the abusers to feel a "high".

Particle Size Reduction

The method aims at evaluating the efforts required to reduce the particle size of the pharmaceutical compositions via physical methods, such as, for example, crushing, grinding, cutting and other means of particle size reduction.

Figure 18:
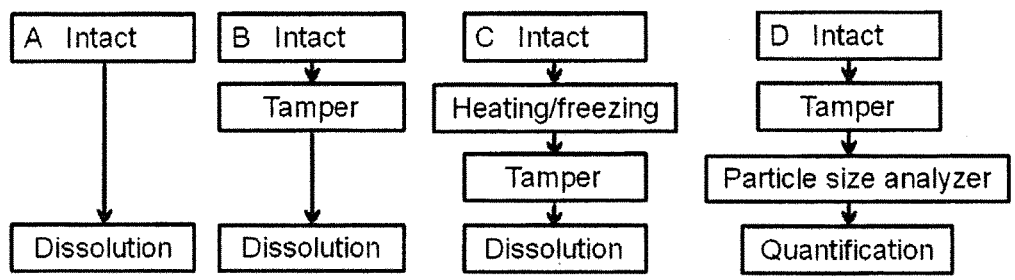
FIG. 18 illustrates a particle size reduction test program for a pharmaceutical composition.

The particle size reduction test program is shown in FIG. 18. The test can be carried out using a number of mechanical and electrical tools found in common households or commonly available in retail. The types of tools included in this test are given in Table 1.

TABLE 1

Overview of tool types

| Test no. | Tool name and type |
|---|---|
| 1 | Mortar and pestle - pestle 5 times |
| 2 | Hammer (hammer head 470 g, impact area 5.7 cm$^2$) - strike 5 times |
| 3 | Grater (at least 4 openings pr. cm$^2$) - grate 5 times |
| 4 | Food Chopper, Mini Quick 6720 OBH (150 W, 4500-5000 rpm) - 30 second (pulsating) |
| 5 | Coffee Grinder, Krups GVX242 (200 W) - 30 second (pulsating) |

If the pharmaceutical composition is physically disrupted (Test B and C), the resulting tampered tablet can be analyzed and compared to the intact tablets (test A).

Compositions, such as tablets, subjected to tampering can furthermore be run through a particle size analyzer and the different fractions collected. Each fraction is weighed and dissolved to assess the contents of active drug substance in the different fractions (test D). The applicability of each tool is tested and recorded and the procedure is to operate each tool to the limit. This means that each tool is operated until pharmaceutical composition (e.g., a tablet) or equipment failure is observed.

The particle size reduction test can be performed as described in test A to D and repeated for all tests given in Table 1. Test A: Perform a dissolution test on intact tablets (e.g., n=3) as described in the section describing dissolution testing. The results from test A are defined as control data. Test B: Subject the tablets to tampering according to Table 1 test no. 1, etc., by placing one tablet in a mortar and attempting to crush it with the pestle. Perform a dissolution test (e.g., n=3) to evaluate if the controlled released mechanism in the tablets has been defeated by comparing the results from test B with results from test A.

Test C1 Freezing: Place for example three tablets in a freezer (−18 for approximately 24 hours. Perform a hammer test on the tablets subjected to freeze tampering by placing the tablets on the floor and striking the tablets with a hammer. Conduct a dissolution test on the freeze/hammered tampered tablets (e.g. n=3). Test C2 Microwave heating: Place, for example, three tablets in a beaker and heat them in a microwave as previously described. Subject the tablets to tampering using the method from test B, where the largest particle size reduction is found. Perform a dissolution test on the heated tampered tablets. Test C3: Heating by gas burner: Place, for example, three tablets on a plate. Heat the tablets as previously described. Subject the tablets to tampering using the method from test B, where the largest particle size reduction is found. Perform a dissolution test on the burned/melted tampered tablets (e.g. n=3). Test C4 Melting: Place, for example, three tablets on a large petri dish. Heat the tablets as previously described. Subject the tablets to tampering using the method from test B, where the largest particle size reduction is found. Perform a dissolution test on the tampered and heated tablets.

Test D: Subject the tablet to tampering according to Table 1 test no. 1, etc., by placing one tablet in a mortar and attempting to crush it with the pestle. Transfer the tablet subjected to tampering to the particle size analyzer and collect the different fractions.

Quantify the amount of active drug substance in each fraction collected as content uniformity as previously described in section mastication and buccal test. Report the results in Table 2.

TABLE 2

Result from test no. 1 etc.
Test no. 1: Mortar and pestle

| Particle size fraction (mm) | Fraction weight (mg) | Active drug substance Content (mg - % of label claim) | Comments |
|---|---|---|---|
| X > 5 | | | |
| 5 > X > 2.5 | | | |
| 2.5 > X > 1.12 | | | |
| 1.12 > X > 0.5 | | | |
| 0.5 > X > 0.3 | | | |
| 0.3 > X > 0.125 | | | |
| 0.125 > X > 0.063 | | | |
| 0.063 > X | | | |

The preferred ways of tampering with pharmaceutical compositions from an abuser's point of view, typically achieve maximal reduction of the pharmaceutical composition in a minimal amount of time, while obtaining a powder or similar product which can be dissolved or administered as easily as possible. Efforts required to reduce the particle size of the pharmaceutical compositions via physical methods such as for example crushing, grinding, cutting and other means of particle size reducing methods, are evaluated above. The tampering method which results in the largest reduction of pharmaceutical compositions, such as, for example tableted compositions, is used as the tampering method in the test described below.

Extraction

The extraction test evaluates the extractability of active drug substance from pharmaceutical compositions in different solvents, under different conditions.

Figure 19:
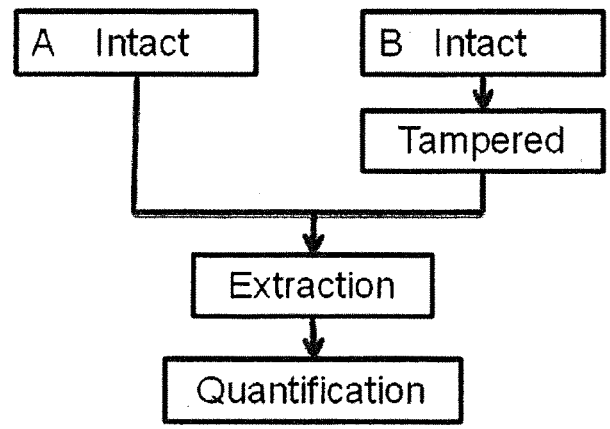
FIG. 19 illustrates an extraction test program for a pharmaceutical composition.

The extraction test program is shown in FIG. 19. Extraction tests can be performed in 5, 10 and 30 ml solvent in order to cover a relevant range. Different sites on the internet describe that 3 ml water often is used when preparing a solution of, for example, MS Contin® for injection. Tests in the laboratory have shown that an extraction volume of 3 ml is insufficient to get reliable and reproducible results when several time points are required. It was found that 5 ml was the smallest practical extraction volume. The second amount of solvent to be tested is 10 ml, as this amount represents a sip. Furthermore, 10 ml can still be used to prepare an injectable solution after evaporation. The third and largest amount of solvent to be tested is 30 ml. This amount is used in order to be sure that as much active drug substance as possible has been extracted. Different ways of handling the solutions have been tested prior to this test. Periodically shaking up to 300 minutes is assessed as the most realistic to be employed by intentional drug abusers. But to be sure that as much as possible of the active drug substance has been extracted, continuous shaking has been selected as method. Several time points have also been tested prior to this test to obtain reliable and reproducible results. The mean $T_{max}$ observed in vivo is 240 minutes for Egalet® morphine, therefore this time point is selected as the latest sampling point. Three time points are taken within the first 60 minutes, as this is most relevant for abusers. Time points tested in this test can be 10, 30, 60, 120, 240 and 1440 minutes.

The solvents have been chosen to cover a broad range of liquids with low and high pH, with some being some polar and some non-polar. The solvents can be grouped into five groups: aqueous buffers; beverages; common household liquids; exotic organic liquids; and simulated liquids. Prior to the extraction test program, the solubility of the active drug substance in the selected solvent is evaluated. If the active drug substance does not dissolve in a given solvent, the solvent can be excluded from the list and the total number of experiments is reduced.

Extraction of active drug substance from pharmaceutical compositions can be performed by dissolving, for example, tablets in different solvents according to, for example, Table 3. The shaking table IKA®-Werke Shaker horizontal HS501 digital, is applied and the shaking speed is 140-160/min.

TABLE 3

List of solvents for extraction of active drug substance from tablets

| Type | Solvent |
|---|---|
| Aqueous solutions | Solution pH 1.2 |
| | Buffer pH 6.8 |
| | Buffer pH 10.0 |
| | Water |
| | Water + EtOH (40% v/v) |

TABLE 3-continued

List of solvents for extraction of active drug substance from tablets

| Type | Solvent |
|---|---|
| Beverages | Coca-Cola ® |
|  | Coca-Cola ® + 40% EtOH |
|  | Vodka |
| Common household liquids | 1% acetic acid |
|  | Ethanol |
|  | Methylethylketone |
|  | Acetone |

Test A: Place one tablet in a brown 30 ml bottle and add 5 ml of the selected solvents according to Table 3 (one solvent per bottle). Place the bottle on the table and (non-stirred) and on a shaking table and shake continuously (speed 140-160/min) throughout the whole experimental period. Withdraw 300 µl sample after 10, 30, 60, 120, 240, and 1440 minutes, respectively. Transfer the sample to a HPLC vial and add 1 ml phosphate buffer pH 6.8. Analyze the samples as content uniformity (CU) as previously described in sections describing mastication and buccal testing. Test B: Subject the tablets to tampering as described above, such as by, for example, freezing, microwave heating, direct heating and melting. Place the tablets subjected to tampering in a brown 30 ml bottle and add 5 ml of the selected solvents according to Table 3 (one solvent per bottle). Place the bottle on a shaking table and shake continuously throughout the whole experimental period. For the rest of the procedure follow the description for test A regarding sampling and analysis. Test A and test B (for example by freezing, microwave, heating and melting, respectively) must be repeated with volumes of 10 ml and 30 ml of the selected solvents, respectively (cf Table 3). All extraction experiments are conducted at room temperature and near-boiling temperature. All experiments are conducted with, for example, n=5.

Injection

The injection test aims to evaluating both quantitatively (i.e. such as for example time, yield, and unit operations required) and qualitatively (i.e. such as for example appearance) the abuse potential of active drug substance from pharmaceutical compositions.

Figure 20:
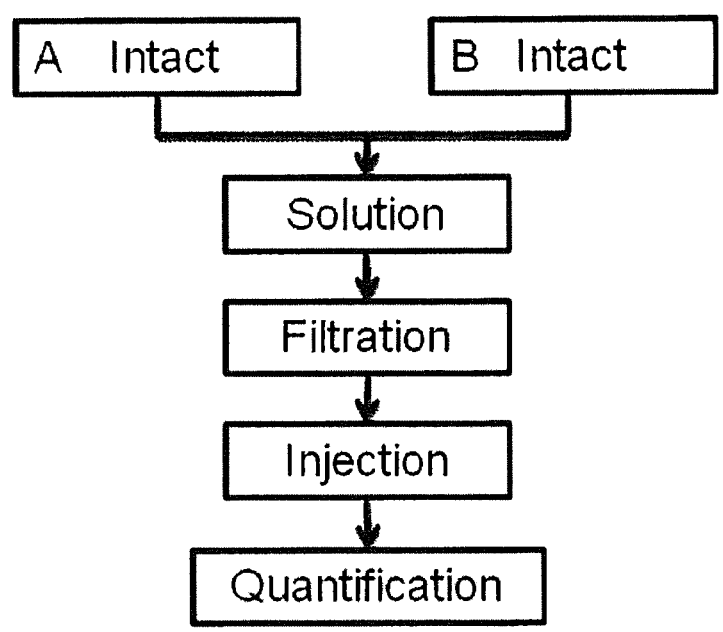
FIG. 20 illustrates an injection test program for a pharmaceutical composition.

The injection test program is shown in FIG. 20. The general strategy behind this test is to mimic the actual procedures applied by drug abusers when preparing a pharmaceutical composition for injection and injecting it. The study design is therefore divided into three parts: A. Preparation, B. Filtration and C. Injection.

Part A, Preparation: The objective of this part is to record the time and effort required to prepare a solution or dispersion that can be used for injection. As pointed out, drug abusers are only prepared to spend limited time for preparing a pharmaceutical composition for abuse. The tests performed as part of this test will thus record the time required to achieve a relevant solution or dispersion that may be utilized for abuse via injection. All tests can be performed in an aqueous media, which is a commonly applied solvent for injection. Three different amounts of solvent (3 ml, 5 ml and 10 ml) are used in order to cover a relevant range. At the internet site Bluelight.com, 3 ml is often mentioned as the approximate volume when preparing a solution of for example MS Contin® for injection. Even though it has been shown that 3 ml solvent may result in problems with reproducibility, using this volume can nevertheless provide useful information. All experiments are conducted at room temperature and near boiling temperature in the dilution step. The effort required to prepare the solution/dispersion is assessed. A measure for this is to assess the number of operations required to achieve the wanted solution/dispersion. Finally, the appearance of the resulting solution/dispersion is assessed in order to evaluate the likelihood that a drug abuser would inject the resulting injectable mass. Part B, Filtration: The objective of this part is to test the types of filter that can be used in filtration of a prepared solution/dispersion. For example, three commonly used filters are tested, and the filtration time, yield and appearance of the resulting solution are recorded. Thereby, an assessment of the time and effort required to perform this operation, which is common practice among drug abusers, can be achieved. Part C, Injection: The objective of this part is to record the time, yield and effort required for injection of a solution/dispersion to take place.

In order to assess the abuse potential of the pharmaceutical compositions, a number of parameters can be recorded. The following criteria can be used to assess the potential for abusing, for example, tableted compositions by injection. A. Time: Drug abusers do not want to spend a significant amount of time trying to prepare a pharmaceutical composition for abuse. Several sources point 0.5-1 hour as the maximum time a drug abuser would want to expend preparing a pharmaceutical composition for abuse. B. Yield: The yield of drug substance that can be obtained from a given pharmaceutical composition is an important factor in determining the desirability of a particular technique for abuse. Yield can be recorded in "% of dose" or mg. C. Appearance: In order to deter intravenous (IV) abuse, many abuse resistant pharmaceutical composition as described herein may include gelling agents. Appearance of the resulting solution or dispersion is considered important as it will deter a number of drug abusers if the injectable mass is not a clear solution, but a viscous and/or unclear, opaque or cloudy dispersion. D. Effort: It seems evident that drug abusers are willing to spend a fair amount of time and effort to prepare a pharmaceutical composition for drug abuse. However, there seems to be a connection between the effort the drug abuser is willing to spend and the "quality of high", i.e., the yield. Therefore, correlating all three parameters above with each other is part of the assessment of abuse potential of the pharmaceutical composition with respect to injection. This will form the overall evaluation on the effort the drug abuser needs to put into preparing the pharmaceutical composition for abuse.

The injection test program is performed on intact compositions and compositions subjected to tampering as shown in Table 4. As is true in each for each of the tests described herein, the pharmaceutical composition evaluated may be a tableted composition. Part A (preparation): Test X (intact tablets) to Y (tablets subjected to tampering according to the particle size reduction part), see Table 4. Place intact tablets and tablets subject to tampering (e.g. n=3) in small bottles and add 3 ml of water to each of the bottles. Place the bottles on a shaking table and shake continuously (speed 140-160/min) throughout the whole experimental period. When everything is dissolved, register the time consumption in Table 4. Transfer the solutions into 5 ml plastic syringes with 19 G (1.1×40 mm) needles.

TABLE 4

Observation on part A preparation
volume 3 ml and room temperature

| Part A | Time to tamper (min) | Effort (operations required) | Appearance T = start | Time to dissolve (min) | Appearance T = dissolved |
|---|---|---|---|---|---|
| X1 | | | | | |
| X2 | | | | | |
| X3 | | | | | |
| Y1* | | | | | |
| Y2* | | | | | |
| Y3* | | | | | |

Part B: (filtration): Test X (intact tablets) to Y (tablets subjected to tampering according to the particle size reduction part) see Table 5 (e.g. n=3). Filter each of the solutions through a separate cigarette filter. After filtration, transfer the filtered solutions into 10 ml plastic syringes with 19 G (1.1×40 mm) needles and note the remaining volume. Report the observations in Table 5.

TABLE 5

Observation on part B filtration (e.g. Cigarette filter)

| Part B | Filtration time (min) | Appearance after filtration | Volume (ml) |
|---|---|---|---|
| X1 | | | |
| X2 | | | |
| X3 | | | |
| Y1* | | | |
| Y2* | | | |
| Y3* | | | |

Part C: (injection): Test X (intact tablets) to Y (tablets subjected to tampering according to the particle size reduction part) see Table 6 (e.g. n=3). Exchange the 19 G needles with a common insulin syringes (27 G×½") needle. Place the syringes with the needle horizontal and press with 3 kg on the piston, measure the time for the mass to pass through the needle. Withdraw 300 µl of each solution, transfer the samples to vials and dilute with phosphate buffer pH 6.8. Analyze the samples as content uniformity (CU) as previously described in sections describing mastication and buccal testing. Report the observations in Table 6.

TABLE 6

Observation on part C injection

| Part C | Time (sec) | Yield (%) | Remarks |
|---|---|---|---|
| X1 | | | |
| X2 | | | |
| X3 | | | |
| Y1* | | | |
| Y2* | | | |
| Y3* | | | |

Repeat the procedure with all filters (for example cigarette filter, cotton pad, tea filter) and volumes stated in Part A (preparation). Furthermore, repeat the procedure performing the dissolution near boiling point.

Snorting

The snorting test aimed to at evaluate the abuse potential of active drug substance from pharmaceutical compositions via snorting. The snorting test program is shown in FIG. 18 (Test D) on pharmaceutical compositions that have been subjected to tampering. In order to assess the potential for abuse of pharmaceutical compositions by snorting, the primary parameter in this test is to assess the physical disruption of the pharmaceutical compositions. The different fractions of tablets subjected to tampering are collected from the particle size analyzer (Test D). The amount of active drug substance in each fraction is determined by content uniformity, as described previously in the sections describing mastication and buccal testing. Report the results in Table 7. Make a qualitative evaluation of the possibility to snorting the different fractions from the particle size analyser.

TABLE 7

Observation from snorting test

| Particle size fraction (mm) | Fraction weight (mg) | Active drug substance Content (mg - % of label claim) | Qualitative evaluation of the possible to snorting (Yes/No) |
|---|---|---|---|
| X > 5 | | | |
| 5 > X > 2.5 | | | |
| 2.5 > X > 1.12 | | | |
| 1.12 > X > 0.5 | | | |
| 0.5 > X > 0.3 | | | |
| 0.3 > X > 0.125 | | | |
| 0.125 > X > 0.063 | | | |
| 0.063 > X | | | |

Abuse-Resistance of a Pharmaceutical Composition

A pharmaceutical composition may be evaluated by three parameters, dissolution rate, particle size distribution, and content uniformity.

If the pharmaceutical composition is classified as an immediated release composition, the pharmaceutical composition is not abuse-resistant, i.e. fail the dissolution test. The term "immediated release composition" denotes a pharmaceutical composition where at least 75% of active drug substance is released from the pharmaceutical composition within 60 minutes when subjected to a dissolution test as described herein.

The pharmaceutical composition fails to be abuse-resistant if the contain of active drug substance is found to be more than 20 mg tested by Content Uniformity in the pharmaceutical composition having a particle size at or less than 0.5 mm upon mechanical treatment by test equipment (physical tampering).

The pharmaceutical composition fails to be abuse-resistant if more than 20 mg of active substance is dissolved in 5 ml solvent after 60 minutes as tested by Content Uniformity.

Definitions

In the present context, the term "resistant to abuse by alcohol" is intended to mean that the in vitro dissolution behaviour of a pharmaceutical composition of the invention is the same or shows a decreased release rate when the pharmaceutical composition is tested in a dissolution medium containing alcohol compared to a medium without alcohol. The ratio ($R_{50}$) between $t_{50\% (v/v)}$ (40% (v/v) ethanol in medium 1) and $t_{50\% (v/v)}$ (medium 1) is 1 or more. $t_{50\% (v/v)}$ (medium 1) denotes the time it takes to release 50% (v/v) of the active drug substance from the pharmaceutical composition in an in vitro dissolution test according to USP 32, NF 27, (711), Apparatus 2, paddle employing buffer or solution at specified pH as dissolution medium (medium 1), and $t_{50\% (v/v)}$ (40% (v/v) ethanol in medium 1) denotes the time it takes to release 50% (v/v) of the active drug substance from the pharmaceutical composition in an in vitro dissolution test according to USP 32, NF 27, (711), Apparatus 2, paddle employing 40% (v/v) ethanol in medium 1 as dissolution medium.

The same may also apply for ratios determined for example for the time when 25%, 30%, 40%, 60%, 70%, 80%, 90% and/or 95% w/w has been released, the conditions being as described above.

In specific embodiments of the pharmaceutical compositions described herein, the ratio $R_{50}$ is at the most 5, such as at the most 4, at the most 3, or at the most 2. In particular such embodiments, the ratio $R_{50}$ is selected from a range of 1 to 1.5, 1 to 1.4, 1 to 1.3, 1 to 1.2, 1 to 1.1, and 1 to 1.05. In another such embodiment the ratio $R_{50}$ is or 1.

In the present context, the term "abuse" is intended to denote the use of a drug in order to induce euphoria or another excitement effect, i.e. the use is not intended to cure a disease or alleviate disease symptoms, but rather for obtaining intoxication.

Solubility definitions; Parts of solvent needed to dissolve 1 part of solute—Very soluble<1; Freely soluble 1-10, Soluble 10-30; Sparingly soluble 30-100; Slightly soluble 100-1000; Very slightly soluble 1000-10,000, Insoluble>10,000 at ambient temperatures.

EXPERIMENTAL

General Aspects of Analytical Methods

Evaluation of candidate, most optimal regarding abuse resistance, relies upon two critical parameters: A shell-construction, which exhibits increased resistance towards physical tampering, in general, and a shell-composition exhibiting an increased hardness or, more specifically, toughness and low ductility, which results in a pharmaceutical composition that is difficult to crush/chew. This means that optimal combination between a shell-composition and a shell-construction provides a virtually non-chewable pharmaceutical composition or a pharmaceutical composition that is extremely difficult to chew. As a perfect shell composition may reduce the importance of the construction (or vice versa) still making the pharmaceutical composition difficult to chew, it is decided not to set an objective of a hardness but do an objective/analytical and subjective comparison between the candidates. All of the candidates (shell-constructions as well as shell composition) may be suitable but it is only the candidates rating the best that go through an extensive evaluation. Different types of analytical/objective methods are used, since they provide limited information regarding chewability when assessed individually. When evaluated/compared to each other they give a good measure of how difficult it is to chew a pharmaceutical composition for example tablet according to the invention.

Micro Hardness

The microhardness of polymeric material is related to mechanical properties such as modulus, strength, elasticity and plasticity. There a tendency for high modulus and strength values to correlate with higher degrees of microhardness. Furthermore, mechanical performance factors such as creep resistance, fatigue life, toughness and the stability of properties with time, stress and temperature have become subjects where microhardness emerges as a property which is sensitive to structural changes.

Chewing on very hard material will introduce pain in the teeth or jaw. As the hardness of the surface of a material increases, the material becomes more resistant to chewing I composition. Additionally, in the context of the pharmaceutical compositions described herein, it is presently thought that if the shell composition is so hard that deformation of the composition by chewing is impossible, then the matrix composition should not separate from the shell as a result of chewing alone. Measurements of the microhardness of different shell and matrix compositions could provide information on the resistance to chewing.

A Vickers hardness tester, which measure the surface material resistance to indentation was used. The Vickers hardness test method consists of indenting the test material with a diamond indenter, in the form of a right pyramid with a square base. The two diagonals of the indentation left in the surface of the material after removal of the load are measured using a microscope and their average calculated. The area of the sloping surface of the indentation is calculated.

One tablet was placed at the test plat and the diameter indenter is placed just at the surface. The full load was set to 5 N and the time for indenting was set to 30 s.

The Vickers hardness in this case is given by dividing the load in Pa by the square mm area of indentation.

Measuring of the microhardness makes it possible to rate different shell compositions in relation to chewability. As described herein, the method is an objective measurement of hardness.

Tablet Breaking Force

The tablet breaking force is described in USP general chapters <1217> and in Ph. Eur 2.9.8 as resistance to crushing of tablets. The test is intended to determine, under well-defined conditions, the resistance to crushing of tablets measured by the force needed to disrupt them by crushing. The results are normally forces expressed in newtons.

The normal breaking force apparatus described in USP chapter <1217> has flat surfaced platens moving toward each other. The flat surface of the platens does not simulate a bite on a tablet. To gain information about chewability it is important to simulate the bite in the mouth. Therefore an apparatus with two molar teeth was constructed. The apparatus is an older model of a normal tablet breaking force apparatus. Two molar teeth were obtained from the School of Dentistry, University of Copenhagen, Denmark. The molar teeth were glued on the flat surfaced platens.

The pressure applied was initially given at kg/molar. An estimate was made of the surface of the molar that touches the tablet. A molar tooth is usually around 1 $cm^2$. The tablet only received a downward pressure from one third of the teeth as only one third of the tooth was in contact with the tablet. Therefore the surface is estimated to 0.3 $cm^2$. One tablet was placed between the teeth and weights of respectively 4.7 and 10 kg were placed on the apparatus. It was noted at which weight the tablet disintegrates or the tablet was visual inspected for marks.

The apparatus was only capable of deliver a pressure of 10 kg pr molar for example 10 kg pr 0.3 $cm^2$ teeth. The tests performed with this apparatus made it possible to illustrate a poor resistance to chewing of conventional tablets, cf. the examples below. However, this method is not capable of providing a pressure that will damage a tablet formulated according to the description provided herein. Tablet breaking strength In general, testing of pharmaceutical compositions with a Texture Analyser can be used to quantify quality parameters such as compression, puncture/penetration, tension, fracture/bending, extrusion, cutting/shearing. The measurements are used to give information of tablet strength, swelling and disintegration of tablets, tablet coating adhesion and breaking strength of hard capsules etc.

In particular with respect to evaluation of the chewability of a pharmaceutical composition, the quality parameters compression and puncture/penetration are of relevance. These measurements are performed using a texture analyser (TA.XTplus, Stable Micro Systems Ltd., Surrey, UK). Both techniques, compression and penetration, are used to evaluate the power of resistance, for example, the breaking strength, of different shell and matrix compositions according to the invention and OxyContin®. The values obtained by compression and penetration cannot be compared directly as the result depends on given test conditions.

Different special attachments to the texture analyzer are available dependent on the specific technique employed. One technique is the uniaxial compression test, where the samples are deformed using a simple cylindrical probe or a flat plate as described under the breaking force. Another technique is a penetration or puncture test, where a probe is made to penetrate into the test sample and the force necessary to achieve a certain penetration depth or the depth of penetration in a specified time, under defined conditions, is measured and used as an index of hardness.

In the examples, the following techniques were applied using the Texture Analyser: compression technique and penetration technique.

Parameters for Compression Technique

One tablet at a time was placed at the test surface, and a plate with a diameter of 45 mm was pressed into the tablet with a test speed of 0.5 mm/s. The load needed to compress the tablet 3 mm was measured.

Parameters for Penetration Technique

One tablet at a time was placed at the test surface, and a needle with a diameter of 2 mm was pressed into tablets with a test speed of 0.5 mm/s. The load needed to penetrate the needle 4 mm down was measured.

The texture tests made it possible to illustrate that the tablets according to the invention have a very high index of hardness compared to that of a conventional tablet. Given that an increased hardness indicates a better resistance against chewability, these methods can be a part of several methods used to evaluate the chewability.

Chewing Apparatus

The chewing apparatus is as described in the section directed to mastication and buccal testing. One tablet from each of examples 1-4 was placed in the chewing chamber without any kind of solution (dry chewing). At each test initial position (matrix side horizontal or vertical) was noted. When each piston touched the tablet it was twisted simulating a chew with a frequency of approx. 55 chews per minute. The temperature of the chewing chamber was set to 37° C. to simulate the temperature of a human mouth. The chew counter was set to 15 chews and, afterwards, the tablets were visually inspected and the condition of each tablet was noted. Hereafter, the chew counter was set to 60 chews, followed by visual inspection and the condition of each tablet was noted. This procedure was followed until the shell was damaged to an extent where the shell and matrix could be separated.

This analytical method can to a certain extent simulate the mastication process in the mouth, but the influence of saliva on the mastication of the pharmaceutical composition is not investigated by this method. The method can be used to evaluate different pharmaceutical compositions according to the invention in relation to chewability. Together with information of the material hardness (measured by the micro-hardness of the material), and hardness of the pharmaceutical composition (measured by the tablet breaking force and tablet breaking strength), the results can be helpful to select the best materials to fulfill the aim of developing a pharmaceutical composition that is extremely difficult to chew/break.

Methods

Moulding of Shells in Laboratory

An accurate amount of polymer and, if present, plasticizer are weighted and blended with simple volumetric mixing. Liquid plasticizers are added drop for drop. The mixture is hereafter placed in the heater cylinder of an injection moulding machine (Haake MiniJet II, Thermo Electron, Karlsruhe, Germany). Temperature in the cylinder was usually set within 120-190° C. Moulding pressure was 500-900 bar (50-90 MPa) and time was set to 15-30 seconds. Approximately 8 minutes were used for the shell compositions to melt, then the shell was moulded and removed from the mould shortly after.

Filling with Placebo Matrix

The below mentioned matrix composition was filled into the heater cylinder of an injection moulding machine (Haake MiniJet II, Thermo Electron, Karlsruhe, Germany) and the temperature in cylinder is set to 90-120° C., 500-800 bar (80 MPa) in 15-30 seconds. The shell was then inserted and filled with matrix.

Matrix Composition (Placebo)

| | |
|---|---|
| PEO 300,000 | 74.3% (w/w) |
| PoloXamer 188 | 19.2% (w/w) |
| Mannitol | 6.4% (w/w) |
| BHT | 0.1% (w/w) |

Preparation of the (Shell) Composition and Preparation of Pharmaceutical Compositions in Large Scale The shell material/composition was prepared by adding the polymer and plasticizer to a MTI-Mixer at a temperature about 19-21° C. After mixing at around 1000 rpm, the mixer was stopped when the temperature reached 40-50° C. and material adhered to the MTI-Mixer, if any, was manually incorporated into the mixture. The mixture was left to cool for about 10 minutes. The mixing was then finalized with a short high-speed mix in order to minimize lump formation. The matrix material/composition was prepared as described above.

The shell and matrix were moulded in one process, where the shell was moulded in a first step and the matrix was moulded directly into the shell in a second step (co-moulding or 2 component moulding). The injection moulding machine used is Arburg Allrounder 420 V 800-60/35.

Dissolution Test

Dissolution tests were performed in accordance with USP 32, NF 27, (711), Apparatus 2 (paddle method). The dissolution medium consisted of phosphate buffer solution pH 6.8 and ethanol in concentrations from 0-40% v/v or HCl solution pH 1.2 and ethanol in concentrations from 0-40% v/v. The volume of the dissolution medium was 900 ml and the rotation speed of the paddles was 50 rpm throughout the dissolution run. The temperature was 37° C. Samples were withdrawn at suitable time intervals and analysed for content of active drug substance (morphine) by HPLC UV-detector at 281 nm and by UV-online at 285 nm.

Analytical and Rating System for Chewability

The rating system was divided into two parts; one that provided an objective/analytical description of chewability and another that provided a subjective description.

The analytical part entailed: measurements of micro hardness, tablet breaking force, texture analysis and chewing test.

Subjective Analysis (i.e. Tested in Man)

The subjective part entailed: hardness of shell, discomfort when chewing, extent of deformation, adherence between shell and matrix; all the previous mentioned parameters reveal how difficult it is to separate shell from matrix (how much time does it take to separate shell from matrix)—hence chewability. In those situations where the matrix is separated from the shell, it is important to ensure that the matrix is unpleasant to chew. If this is the case, it is inconvenient and, accordingly, the person would have less motivation to chew the matrix. Moreover, if the matrix is very hard, it becomes more difficult to deform the tablet and accordingly, and it becomes more difficult to chew the tablet.

Shell Constructions and their Properties

In order to make the shell more abuse resistant some efforts concerning the construction of the shell was made. The main purpose was to gain a hard shell without changing the dissolution rate of the pharmaceutical composition. Constructions that were thought to contribute to physical adhesion within shell and matrix was tried. Different shell constructions are described and discussed below:

Shell construction (Corresponding to shell of FIGS. 1A, 1B and 1C—shell 2), however with a wall thickness of approx. 0.6 mm. Matrix volume 300 mm$^3$. Concerning the controlled release feature in the system of the technology, this construction has no influence on the usual dissolution-profile (it provides the usual zero-order release). Compared with the other constructions (see below), this construction showed next to no resistance to chewing. The shell broke easily and matrix fell out. This construction would score lower in the rating system compared to other candidates, although it is relatively resistant towards chewability.

Shell construction (see FIGS. 1A, 1B and 1C—shell 2)). Wall thickness 1.4-1.8 mm. Matrix volume 300 mm$^3$. This construction is the most simple way of achieving an increased hardness and discomfort when attempted to chew—thus less appealing to chew seen from the point of view of a potential abuser (discomfort is a subjective measure and can only be rated by testing in man). The matrix construction is similar to matrix construction in shell construction (FIGS. 1A, 1B and 1C—shell 2, with a thickness of approximately 0.6 mm), hence it resulted in the same dissolution rate. The hardness and discomfort are increased for the pharmaceutical composition using shell construction (FIGS. 1A, 1B and 1C—shell 2, with a thickness of 1.4-1.8 mm). The construction does not give increased adhesion between shell and matrix. Any deformation of the shell caused the matrix to fall out; therefore the choice of shell material was critical for this construction. This construction would score lower in the rating system compared to other candidates, although it is relatively resistant towards chewability, however if the optimal shell composition was used for the shell construction, preventing the deformability of the construction, then this construction would be OK. The choice to pursue a construction relies on two parameters: shell construction and shell composition. One parameter could have such an effect that it compensates the weaknesses of the other parameter.

Shell construction (see FIGS. 3A, 3B and 3C—shell 202). Outer shell wall thickness approx. 1.0 mm, reinforcement wall thickness approx. 0.5 mm. Matrix volume approx. 244 mm$^3$. The crossed reinforcement walls inside this pharmaceutical composition increased the resistance regarding chewability without increasing the size. These evaluations were subjective evaluations based on chewing. The construction showed good hardness and highly increased discomfort (better than the construction (FIGS. 1A, 1B and 1C—shell 2, with a thickness of 1.4-1.8 mm)). Due to the crossed reinforcement walls the physical adhesion between matrix and shell are slightly increased. The drawback for this construction is the change of dissolution rate in vitro as well as in vivo.

Figures 4A, 4B:
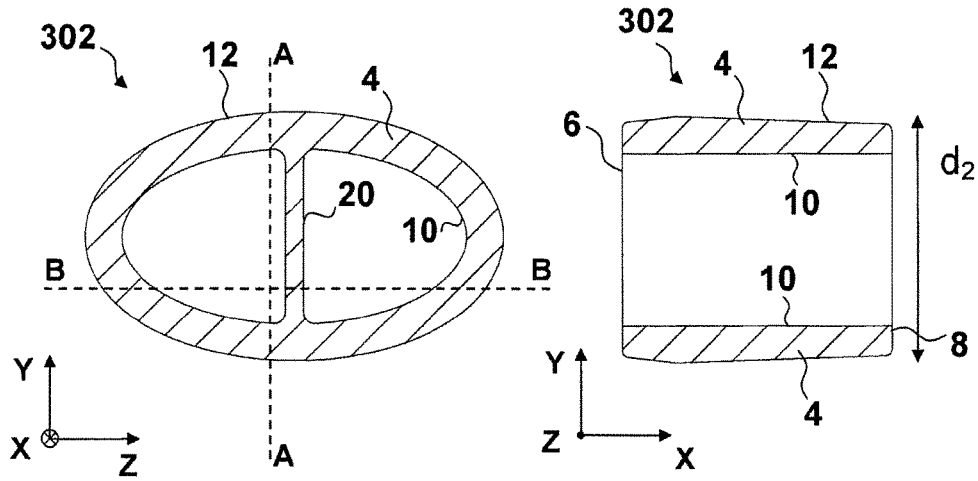
FIGS. 4A-4C schematically illustrate an exemplary shell according to the present invention.
Figure 4C:
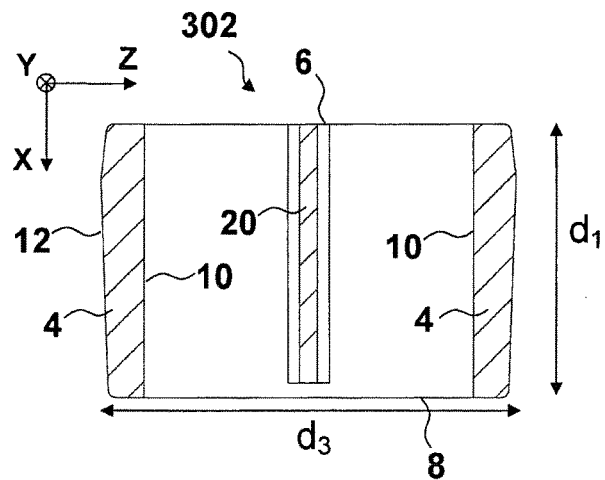

Shell construction (see FIGS. 4A, 4B and 4C—shell 302). As construction (FIGS. 3A, 3B and 3C—shell 202), but only one reinforcement wall. Outer shell wall thickness approx 1.0 mm, reinforcement wall thickness 0.5 mm. Matrix volume approx. 281 mm$^3$. Same pros and cons as construction (FIGS. 3A, 3B and 3C—shell 202).

Shell construction (see FIGS. 5A, 5B and 5C—shell 402). Outer shell wall thickness approx. 1.25 mm, reinforcement wall thickness about 1.0 mm. Matrix volume approx. 305 mm$^3$. In order to be able to fill matrix from one end, an opening in the reinforcement wall was needed. The construction showed good hardness and increased discomfort (same as construction (FIGS. 1A, 1B and 1C—shell 2, with a thickness of 1.4-1.8 mm)). The physical adhesion between shell and matrix was highly increased due to the opening in the reinforcement wall (better than construction (FIGS. 3A, 3B and 3C—shell 202) and construction (FIGS. 4A, 4B and 4C—shell 302)). A pharmaceutical composition with a high hardness, for example shell composition (V), showed very good properties regarding discomfort.

Shell construction (See FIGS. 6A, 6B and 6C—shell 502). As construction (FIGS. 5A, 5B and 5C—shell 402) with two reinforcement walls. Matrix volume approx. 311 mm$^3$. This construction had the same adhesive, and discomforting properties as construction (FIGS. 5A, 5B and 5C—shell 402), the passage between the reinforcement elements was changed to avoid separation of matrix composition in half.

Shell construction (see FIGS. 7A, 7B and 7C—shell 602). Elliptical shape 12×16×8.5 mm. Wall inside as construction (FIGS. 5A, 5B and 5C—shell 402). The outer wall had a minimum thickness of approx. 2.4 mm. Matrix volume approx. 305 mm$^3$. This construction was an attempt to increase the shell thickness as much as possible, and keeping the pharmaceutical composition swallowable. Because of the good physical adhesion achieved in construction (FIGS. 5A, 5B and 5C—shell 402) and construction (FIGS. 6A, 6B and 6C—shell 502) a similar reinforcement wall is provided. The construction shows highly increased hardness and discomfort. The reinforcement wall has been removed from the construction and even without the reinforcement wall (see FIG. 2) this construction showed highly increased discomfort.

Shell construction (see FIGS. 10A, 10B, 10C and 10D—shell 802). Ten matrixes placed in ten cavities of the shell. The volume of each matrix composition is approximately 217 mm$^3$/10×21.7 mm$^3$. This construction forms a number of reinforcement walls between the cavities/lumens, which radically increases the strength of the pharmaceutical composition. The outer shell wall has a thickness between 0.2 and 1.4 mm. Because of the good physical adhesion achieved in construction (FIGS. 5A, 5B and 5C—shell 402) and construction (FIGS. 6A, 6B and 6C—shell 502) a similar reinforcement wall was provided in each lumen. To facilitate production of this shell in large scale machinery, a channel 0.35 mm deep and 0.7 mm wide was placed at the first end between the cavities. This channel ensured a consistent filling of matrix composition into all cavities.

Shell construction (see FIGS. 9A, 9B, 9C and 9D—shell 702). Oval shaped pharmaceutical composition. Elliptic cylinder shaped matrix. Matrix volume approximately 217 mm$^3$, leading to active drug substance of 100 mg. The outer wall had a thickness between 0.7 and 1.9 mm. The construction was based on the construction (FIGS. 1A, 1B and 1C—shell 2, with a thickness of 1.4-1.8 mm). To facilitate oral administration (swallowing), the shape was more rounded. To facilitate production of this construction in large scale machinery, the shell was not equipped with the reinforcement wall, described in construction (FIGS. 5A, 5B and 5C—shell 402) and construction (FIGS. 6A, 6B and 6C—shell 502). Therefore it was crucial to the tamper resistance that a certain adherence between shell and matrix was achieved.

Example 1

Different Shell Constructions were Tested with Shell Composition I

Shell Composition I

| Ethyl Cellulose "20" | 88.0% (w/w) |
|---|---|
| Cetostearyl alcohol | 12.0% (w/w) |

Ethyl Cellulose is a starch derived polymer and is widely used in oral pharmaceutical compositions.

The shell composition was moulded in laboratory scale as well as in large scale production described above. Shells made from the shell compositions above and having construction shell 2 (wall thickness 1.4-1.8 mm), shell 402 and shell 602 were tested in man. The following results were obtained:

| | Shell construction | | |
|---|---|---|---|
| Composition I | Shell 2, wall thickness 1.4-1.8 mm | Shell 402 | Shell 602 |
| Duration | 7 sec | 15 sec | 30 sec |

The constructions shell 2 (wall thickness 1.4-1.8 mm) and shell 602 were also tested in the chewing apparatus. The shell with shell construction 2 (wall thickness 1.4-1.8 mm) had signs after 15 chews and after 75 chews, the shell crushed. The shell construction 602 exhibited good duration, which can be ascribed to the shell construction itself and the hardness that can be obtained from ethyl cellulose if the thickness of shell is sufficient.

In the following examples 2-5, a number of pharmaceutical compositions comprising different shell composition and constructions with the placebo matrix composition, as described above, are tested.

Example 2

Shell Compositions with Different Grades of Ethyl Cellulose and Castor Oil as Plasticizer to Achieve Hard Shell with Better Adherence to Matrix than Shell Composition I Shell Composition II

| Ethyl Cellulose "20" | 88.0% (w/w) |
|---|---|
| Castor Oil | 12.0% (w/w) |

Ethyl Cellulose provided a hard shell, but had the tendency to shrink, which complicated the removal of the shell from the mould and filling of the matrix in the laboratory procedure. This will not become a problem in larger scale production, where matrix and shell are prepared simultaneously and cooled together. Castor oil did not weaken the polymer and made the material soft enough to be able to mould shell constructions 2 (wall thickness 1.4-1.8 mm) and 402 in the laboratory.

| | Shell construction | |
|---|---|---|
| Shell composition II | Shell 2, wall thickness 1.4-1.8 mm | Shell 402 |
| Duration | 30 sec | 30 sec |
| Micro hardness | 11 kPa/mm$^2$ | 11 kPa/mm$^2$ |

The chewability test showed that shell composition II could be described as good in accordance with the criteria described above in shell construction 2 (wall thickness 1.4-1.8 mm) and 402 due to adherence to matrix and a good hardness of the shell.

The micro hardness was measured as described above and this shell composition had a hardness of 11 kPa/mm$^2$, which is quite a lot compared to the other shell compositions that will be described. Accordingly, the shell composition tested has improved properties compared with shell composition I. Thus, choice of plasticizer seems to have impact on the chewability of the shell.

Shell Composition III

| Ethyl Cellulose "100" | 88% (w/w) |
|---|---|
| Castor Oil | 12% (w/w) |

A similar shell composition was prepared with Ethyl Cellulose "100", which has longer polymer chains that could lead to a harder shell.

| | Shell construction | |
|---|---|---|
| Shell composition III | Shell 2 (wall thickness 1.4-1.8 mm) | Shell 402 |
| Duration | 30 sec | 15 sec |

This construction had teeth marks after 15 chew in the chewing apparatus and it crushed after 90 chew.

Accordingly, substituting ethyl cellulose "20" with ethyl cellulose "100" seems to improve the hardness of the shell and the resistance against chewing.

In the chewing apparatus shell composition III showed higher resistance than shell composition I.

This example shows that shell compositions with Ethyl Cellulose 100 form a hard shell.

Example 3

Shell Compositions with Polycaprolactone (IV)

Shell Composition IV

The shells were made of 100% polycaprolactone.

The Polycaprolactone used here has a molecular weight of 80,000, which has a higher tensile strength (measured by texture-analysis), which makes it more resistant towards chewing. It has a melting point around 60° C. No plasticizer was employed.

The shell composition is easy to mould and possess the necessary ductility (i.e. the extent to which materials can be deformed plastically without fracture, such that it will deform and not fracture upon chewing attempts). This polymer demonstrated good adherence to matrix as well, as removal of shell during the subjective tests was difficult compared to other shell compositions. Moreover, the low melting point was found to be an advantage in large scale production.

|  | Shell construction | | |
| --- | --- | --- | --- |
| Shell composition IV | Shell 2 (wall thickness 1.4-1.8 mm) | Shell 402 | Shell 602 |
| Duration | 20 sec | 20 sec | 30 sec |
| Micro hardness | 2 kPa/mm² | 2 kPa/mm² | 2 kPa/mm² |

The penetration technique was carried out as described above on shell construction 2 (wall thickness 1.4-1.8 mm) with matrix composition, but the needle bent before a given pressure could be established. This indicated that the shell polymer forms a shell with high density leading to a hard surface. Moreover, this polymer had a good adherence to the matrix composition.

The low melting point and, low ductility, adherence to matrix composition and density was an advantage with this polymer. It also performed well in chewability test. This polymer may be promising due to its low ductility, which alone gives a hard shell and that lacks of flexibility and adherence.

Example 4

Shell Composition V with Cornpack 200

Shell Composition V

The shells were made of 100% Cornpack 200.

Cornpack 200 is a starch derived polymer, and can consist of a high number of glucose molecules and can have a number of side chains. It has a high melting point, and when moulded it gives a very hard shell. Saliva in the oral cavity contains amylase, an enzyme, which degrades starch to di and tri saccharides and into the final degradation step to maltose and glucose molecules. Corn starch will not degrade considerably, despite the presence of amylase due to the side chains of the polymer when moulded to a hard shell. No plasticizer was employed.

|  | Shell construction | | |
| --- | --- | --- | --- |
| Shell composition V | Shell 2 (wall thickness 1.4-1.8 mm) | Shell 402 | Shell 602 |
| Duration | >2 min | >2 min | >2 min |
| Micro hardness | 11 kPa/mm² | 11 kPa/mm² | 11 kPa/mm² |

The micro hardness of 11 kPa/mm² also indicated a pharmaceutical composition with a hard shell.

This polymer showed much promise because it was almost impossible to chew, and measurements indicated a good hardness.

Example 5

Breaking Force and Texture Analyses—A Comparison of a Tablet Made from Shell Construction 2 (Wall Thickness 1.4-1.8 mm) and Shell Composition IV Versus OxyContin® Tablet A pharmaceutical composition made from shell composition IV and contained in shell construction 2 (wall thickness 1.4-1.8 mm), was used to compare OxyContin® tablet.

The compression technique was used and following results was established

|  | Applied Load | Remarks |
| --- | --- | --- |
| Tablet with shell construction 2 (wall thickness 1.4-1.8 mm) & shell composition IV | Overload at 50 kg (It was not possible to destroy the tablet) | No sign of compression |
| OxyContin ® tablet | NA (disintegrated) | Disintegration |

In the test with compression, the shell also showed a high resistance to the applied pressure, while the conventional, compressed tablet was disintegrated. Further, the shell composition IV showed no sign of compression, possibly due to its low ductility.

Example 6

Resistant to Abuse by Alcohol in a Pharmaceutical Composition Containing Morphine Sulphate with Different Shell Compositions and Constructions A matrix composition (batch no. 066-0169-08-009B) was prepared from the following ingredients:

| Matrix | % (w/w) |
| --- | --- |
| Morphine sulphate pentahydrate | 51.5 |
| PEO 300.000 | 32 |
| BHT | 0.1 |
| Mannitol | 3 |
| PoloXamer 188 | 13.4 |

Two different shell compositions were prepared from the following ingredients

| Shell composition V | % (w/w) |
| --- | --- |
| Cornpack 200 | 100 |

Shell Composition III

| Ethyl Cellulose (grade 100) | 88 |
| --- | --- |
| Castor Oil | 12 |

In addition, two different shell constructions 2 (wall thickness 1.4-1.8 mm) and 602 were prepared using the two different shell compositions, as shown in the table.

| Batch No. | Shell composition | Shell construction |
| --- | --- | --- |
| 08-0226-058 | III | 2 (wall thickness 1.4-1.8 mm) |

-continued

| Batch No. | Shell composition | Shell construction |
|---|---|---|
| 08-0228-085 | III | 602 |
| 08-0230-058 | V | 2 (wall thickness 1.4-1.8 mm) |
| 08-0232-058 | V | 602 |

The four batches were tested using the dissolution tests described in section Methods. Batch No. 08-0226-058 and 08-0228-058 were tested in phosphate buffer pH 6.8 and phosphate buffer pH 6.8 containing ethanol in ratio 60:40 (% v/v). Batch No. 08-0230-058 and 08-0232-058 were tested in phosphate buffer pH 6.8, phosphate buffer pH 6.8 containing ethanol in ratio 60:40 (% v/v) as well as in HCl solution pH 1.2 and HCl solution pH 1.2 containing ethanol in ratio 60:40 (% v/v).

All dissolution profiles showed that the release corresponds to a zero order release. In the table below is shown values for the time to where 50% of the drug is released. For both shell compositions and shell constructions are shown that the $R_{(50)}$ are higher than 1.2, which clarify that the dissolution profiles are much slower in alcohol containing media compared to the same media without alcohol. These results show that it is only the composition of matrix, which affect the release behaviour in the alcohol versus non-alcohol media.

| Batch no. | Media | $t_{50\% (v/v)}$ (min) | $R_{(50)}$ |
|---|---|---|---|
| 08-0226-058 | buffer pH 6.8 | 424 | 1.4 |
| | buffer pH 6.8:EtOH 60:40 (w/w %) | 610 | |
| 08-0230-058 | buffer pH 6.8 | 465 | 1.2 |
| | buffer pH 6.8:EtOH 60:40 (w/w %) | 548 | |
| 08-0228-058 | buffer pH 6.8 | 493 | 1.6 |
| | buffer pH 6.8:EtOH 60:40 (w/w %) | 770 | |
| | HCl solution pH 1.2 | 477 | 2.3 |
| | HCl solution pH 1.2:EtOH 60:40 (w/w %) | 1102 | |
| 08-0232-058 | buffer pH 6.8 | 434 | 1.6 |
| | buffer pH 6.8:EtOH 60:40 (w/w %) | 678 | |
| | HCl solution pH 1.2 | 418 | 1.7 |
| | HCl solution pH 1.2:EtOH 60:40 (w/w %) | 709 | |

CONCLUSION

In conclusion, neither the shell compositions nor the shell constructions affected the dissolution results in relation to abuse resistance related to alcohol.

Example 7

Resistant to Abuse by Alcohol in a Composition Containing Morphine Sulphate with Different Shell Constructions A pharmaceutical composition (batch no. 066-203-09-005B) was prepared from the following ingredients:

| Matrix | % (w/w) |
|---|---|
| Morphine sulphate pentahydrate | 36.0 |
| PEO 200.000 | 22.7 |
| PEO 300.000 | 16.0 |
| HPMC 100.000 | 5.0 |
| Carrageenan 379 | 5.0 |
| BHT | 0.1 |

| Matrix | % (w/w) |
|---|---|
| Mannitol | 3.0 |
| PoloXamer 188 | 12.2 |

The shell composition (batch no. 058-063-000B) was prepared from the following ingredients:

| Shell composition V | % (w/w) |
|---|---|
| PLA | 86.0 |
| PEO 200.000 | 14.0 |

Figure 21:
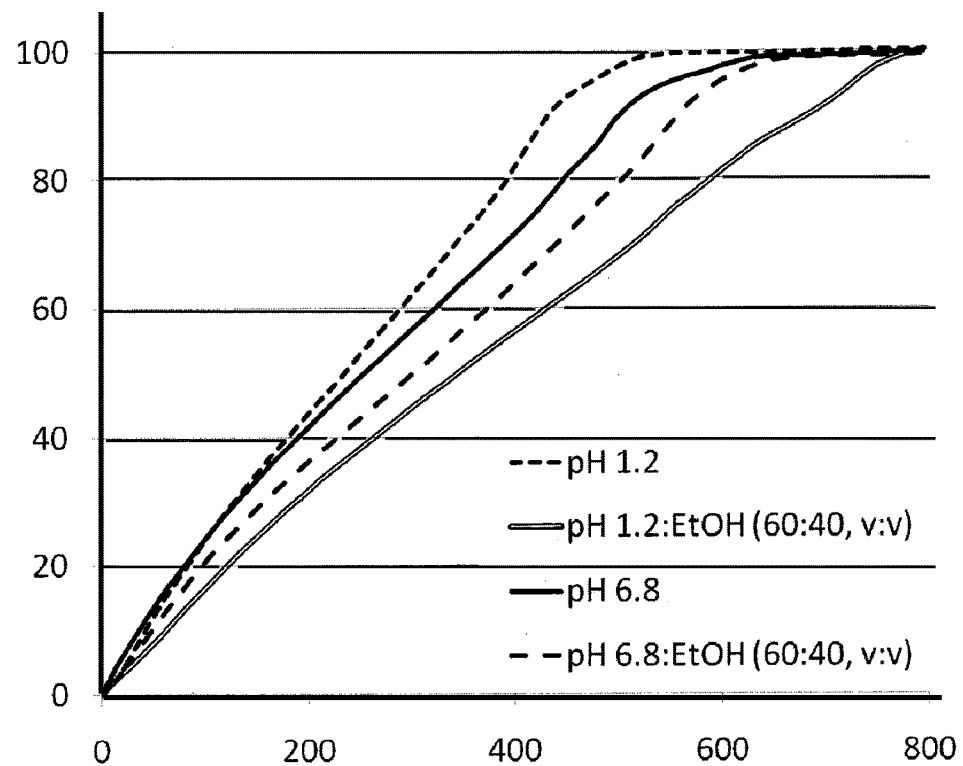
FIG. 21-26 show dissolution profiles of pharmaceutical compositions.

Two shell constructions 702 and 802, respectively, were tested using the dissolution tests described above. Batch No. 1044-059 and 1044-056 were tested in phosphate buffer pH 6.8, phosphate buffer pH 6.8 containing ethanol in ratio 60:40 (% v/v) and Batch No. 1044-056 was additionally tested in HCl solution pH 1.2 and HCl solution pH 1.2 containing ethanol in ratio 60:40 (% v/v). Typical release behaviour (drug release (%) versus time (minutes)) is shown in FIG. 21, when applying shell construction in FIG. 9.

All dissolution profiles showed that the release corresponds to a zero order release. In the table below is shown values for the time to where 50% of the active drug substance is released. Both shell constructions shown that the $R_{(50)}$ are higher than 1.2, which clarify that the dissolution profiles are much slower in alcohol containing media compared to the same media without alcohol. These results show that it is only the composition of matrix, which affect the release behaviour in the alcohol versus non-alcohol media and the shell constructions do not affected the dissolution results.

| Batch no. | Media | $t_{50\% (v/v)}$ (min) | $R_{(50)}$ |
|---|---|---|---|
| 1044-059 (Shell construction 802) | buffer pH 6.8 | 605 | 1.3 |
| | buffer pH 6.8:EtOH 60:40 (% v/v) | 780 | |
| 1044-056 (Shell construction 702) | buffer pH 6.8 | 255 | 1.2 |
| | buffer pH 6.8:EtOH 60:40 (% v/v) | 300 | |
| | HCl solution pH 1.2 | 240 | 1.4 |
| | HCl solution pH 1.2:EtOH 60:40 (% v/v) | 345 | |

Example 8

Tampered Tablets Subjected to Freezing, Microwaving, Burning and Melting Followed by Particle Size Reduction A matrix composition (batch no. 10-0001-066) was prepared from the following ingredients:

| Matrix | % (w/w) |
|---|---|
| Morphine sulphate pentahydrate | 36.0 |
| PEO 300.000 | 16.0 |
| PEO 200.000 | 22.7 |
| Butylhydroxytoluene (BHT) | 0.1 |
| Carrageenan 379 | 5.0 |
| Mannitol | 3.0 |
| PoloXamer 188 | 12.2 |
| HPMC 100.000 | 5.0 |

| Shell composition | % (w/w) |
|---|---|
| Polylactic acid | 86 |
| PEO 200.000 | 14 |

The shell construction of shell 702 is applied.

Dissolution profiles conducted on tampered tablets were compared to dissolution profiles of intact tablets (c.f. protocol on tampering methods).

Tablets Exposed to Freezing

Figure 22:
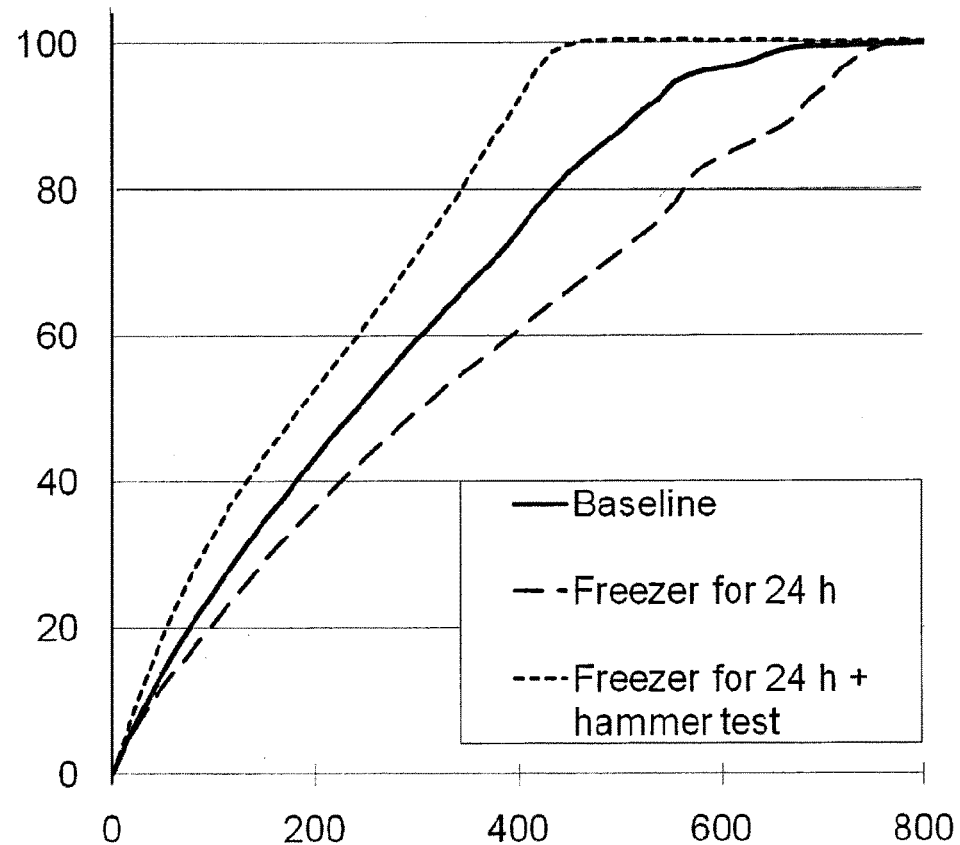

The procedure is described in the protocol as freezing, procedure A through C (A: Intact tablets, B: Intact tablets placed in a freezer at −12° C. for 24 hours, C: Intact tablets placed in a freezer at −12° C. for 24 hours and then subjected to a hammer test). Subsequently all tablets were tested by dissolution described above in buffer pH 6.8. The dissolution profiles (drug release (%) versus time (minutes)) are shown in FIG. 22. As seen in the figure, freezing for 24 hours affect the controlled release mechanism, given that the dissolution profile is slower after freezing. The controlled release mechanism on the frozen tablet knocked with a hammer was affected, given that the dissolution profile is faster than the baseline profile. Conclusively, even though the release rate increases when the tablet has been subjected to freezing and then a hammer, it is not a significant change (such as an instant release behaviour).

Tablets Exposed to Microwaving

Figure 23:
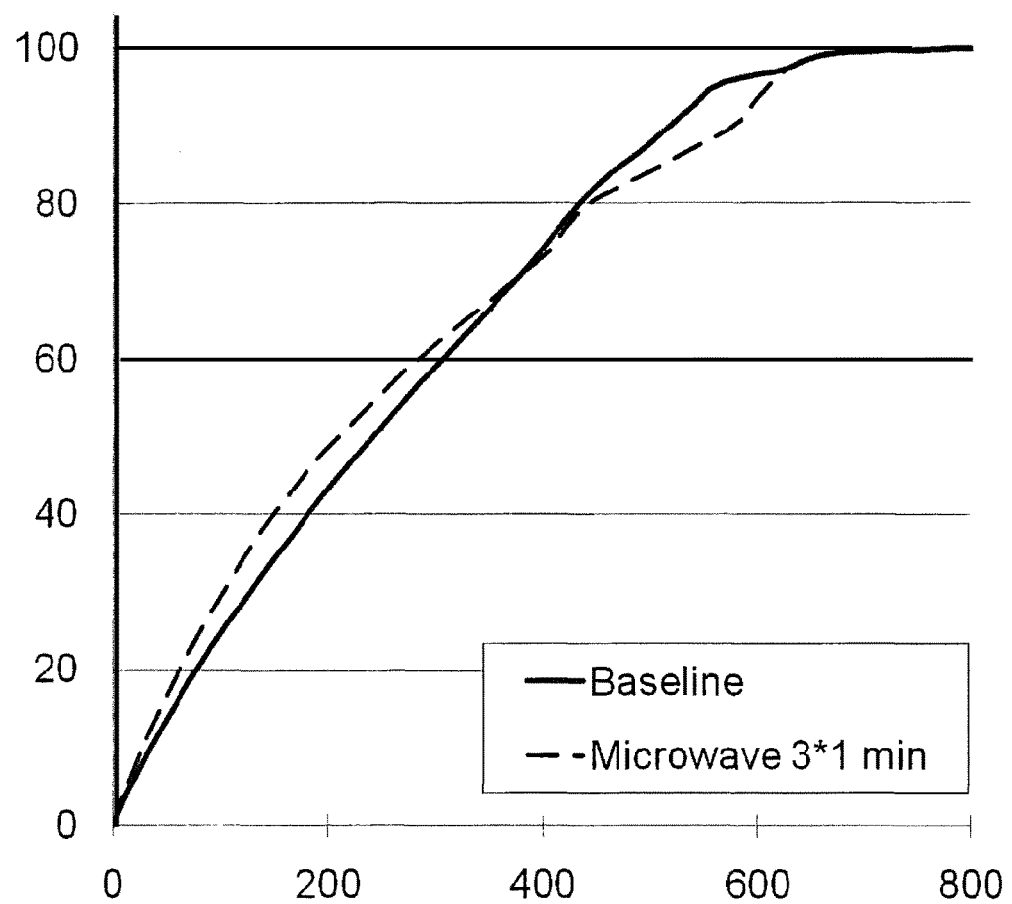

The procedure is described in the protocol as microwaving, procedure A and B (A: Intact tablets, B: Intact tablets placed microwaved 3 times, 1 min. each time, at 800 W). Subsequently all tablets were tested by dissolution described above in buffer pH 6.8. The dissolution profiles are shown in FIG. 23 showing dissolution profile (drug release (%) versus time (minutes)) for baseline (not tampered tablets n=3) and tablets warmed in a microwave for 3 time 1 min (n=3). As seen in the figure, warming tablets for three times 1 min in a microwave oven does not affect the controlled release mechanism, given that the dissolution profile for the tampered tablets is similar to the intact not tampered tablets (named baseline).

Tablets Exposed to Heating by a Gas Burner

Figure 24:
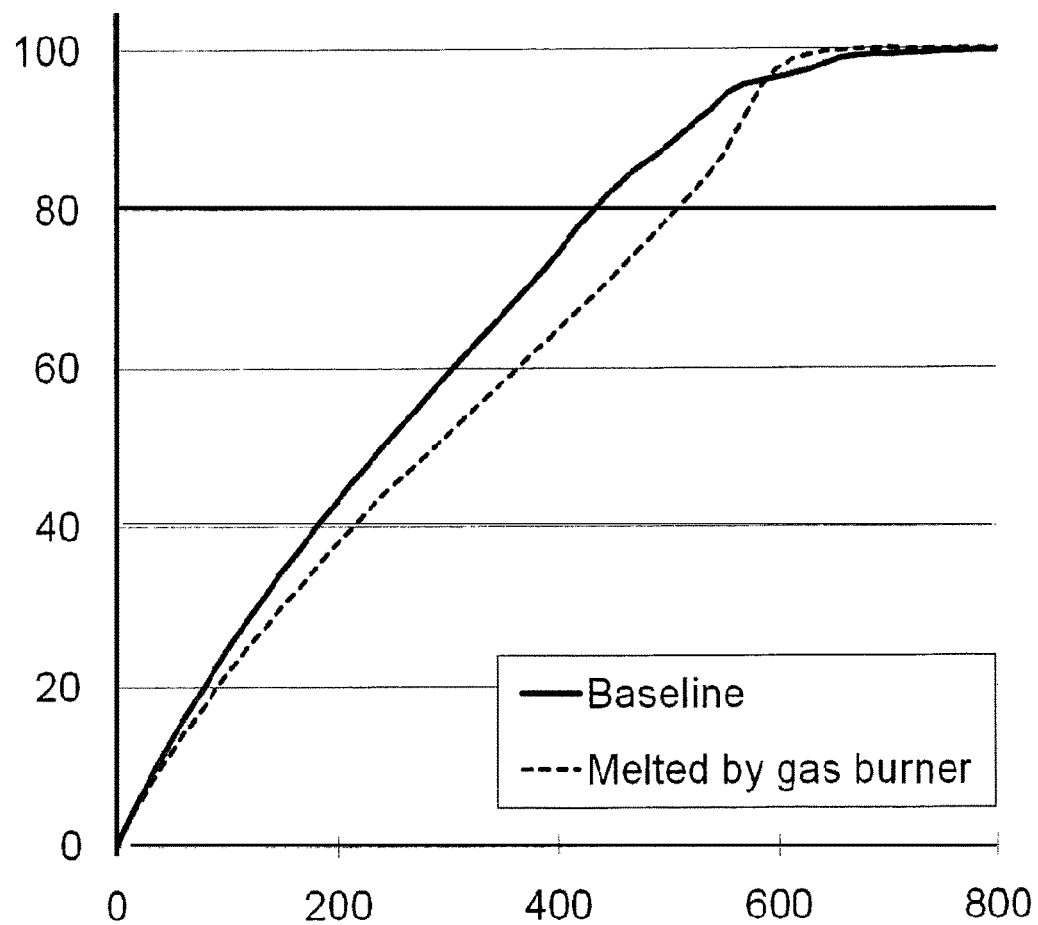

The procedure is described in the protocol as heating by a gas burner, procedure A and B (A: Intact tablets, B: Intact tablets melted with a gas burner for 5 min.). Subsequently all tablets were tested by dissolution described above in buffer pH 6.8. The dissolution profiles are shown in FIG. 24 showing dissolution profile (drug release (%) versus time (minutes)) for baseline (not tampered tablets n=3) and tablets warmed/melted by a gas burner (n=3). As seen in the figure, warming/melting the tablets with a gas burner will only affect the controlled release mechanism by making the release rate slightly lower compared to the intact not tampered tablets (named baseline).

Tablets Exposed to Melting

The procedure is described in the protocol as melting, procedure A and B (A: Intact tablets, B: Intact tablets melted on a heating plate for 20 min. at 180° C.). Subsequently all tablets were tested by dissolution described above in buffer pH 6.8.

Figure 25:
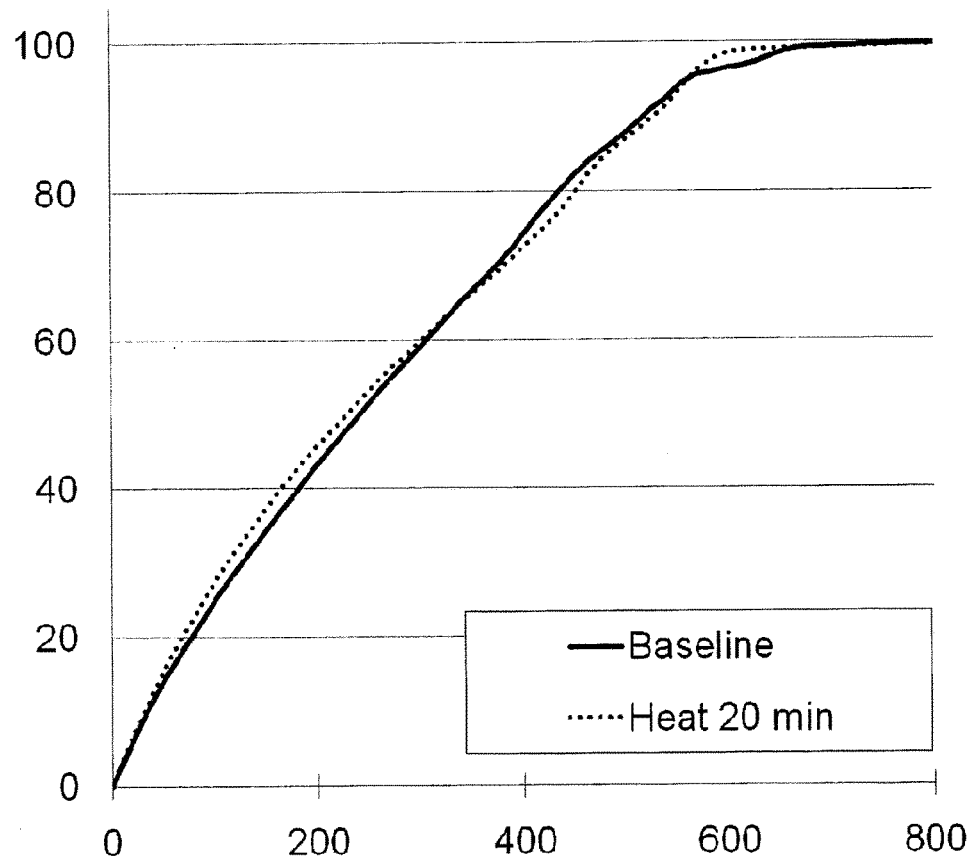

The dissolution profiles are shown in FIG. 25 showing dissolution profile (drug release (%) versus time (minutes)) for baseline (not tampered tablets n=3) and tablets warmed/melted on a heating plate (n=3). As seen in the figure, warming/melting the tablets on a heating plate do not affect the controlled release mechanism, given that the dissolution profile for the tampered tablets is similar to the intact not tampered tablets (named baseline).

Tablets Exposed to Particle Size Reduction

The procedure is described in the protocol as particle size reduction, procedure A through D (A: Intact tablets, B: Intact tablets subjected to physical tampering by use of mechanical or electrical tools, C: Intact tablets placed in a freezer, subjected to microwaving, burning or melting and then subjected to physical tampering by use of mechanical or electrical tools, D: Intact tablets subjected to physical tampering by use of mechanical or electrical tools, followed by particle size analysis). The applied mechanical and electrical tools are listed below with results from the particle size reduction tests. All tests were carried out in triplicate.

| Test no. | Tool name and type | Results |
|---|---|---|
| 1 | Mortar and pestle* | Not possible to disrupt the tablets with the pestle |
| 2 | Hammer | Possible to disrupt the tablets to some extent. The shell stick to the matrix. |
| 3 | Grater* | Not possible to disrupt the tablets with the grater |
| 4 | Food Chopper, Mini Quick 6720 OBH | Not possible to disrupt the tablets before equipment failure. The shell got some marks, but the matrix was not affected |
| 5 | Coffee Grinder, Krups GVX242 | Not possible to disrupt the tablets before equipment failure. The shell got some marks, but the matrix was not affected |

*no further tests were performed with these tampering methods as the tablet was considered as a no tampered intact tablet.

Figure 26:
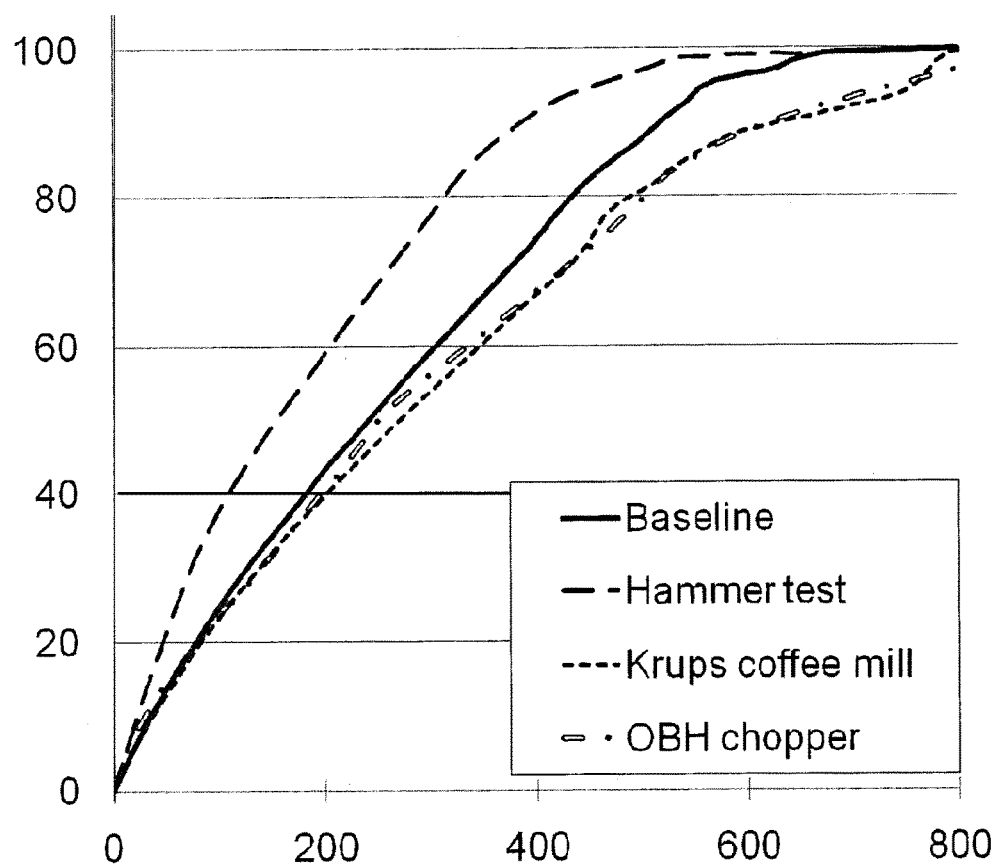

Subsequently all tablets were tested by dissolution described above in buffer pH 6.8. The dissolution profiles from test 2, test 4 and test 5 are shown in FIG. 26 showing dissolution profiles (drug release (%) versus time (minutes)) for baseline (not tampered tablets n=3), hammer test (n=3), milled tablet with Krups coffee mill (n=3) and chopped with OBH chopper (n=3). As seen in the figure, the hammer test affect the controlled release mechanism, by making the release profiles slightly faster than the no tampered tablets (named baseline). Milling the tablet in the coffee grinder or chopping the tablet in the chopper does not affect the controlled release mechanism as the dissolution profile for the tampered tablets is almost similar to the intact not tampered tablets (named baseline).

As it was more or less not possible to reduce the particle size of intact tablets subjected to physical tampering it was decided not to made the extraction, injection and snorting test described in the protocol on tampering methods.

Example 9

Intact Tablets Subjected to Mastication and Physical Tampering by Use of Electrical Tool For the mastication test, the chewing apparatus as described in protocol on tampering methods has been applied on intact tablets and intact tablets has been subjected to physical tampering by use of electronical tool. The abuse deterrence of the tablets is evaluated as a combination of the applied shell construction and shell composition. The measured chew was defined as "dry chewing" as no saliva was present. The chewing machine was calibrated so 44 chews would correspond to 1 minute of chewing. Two identical tablets, from each construction, were tested (duplicates).

The pharmaceutical composition below was applied

| Matrix | % (w/w) |
|---|---|
| Morphine sulphate pentahydrate | 36.0 |
| PEO 300.000 | 16.0 |
| PEO 200.000 | 22.7 |
| Butylhydroxytoluene (BHT) | 0.1 |
| Carrageenan 379 | 5.0 |
| Mannitol | 3.0 |
| PoloXamer 188 | 12.2 |
| HPMC 100.000 | 5.0 |

| Shell composition V | % (w/w) |
|---|---|
| Polylactic acid | 86 |
| PEO 200,000 | 14 |

The shell construction of shell 2 having an outer wall thickness of 0.6 mm is applied). The results are shown below.

| Batch. no. | Tablet no. | No. of chew: 44 (1 min.) | No. of chew: 132 (3 min.) | No. of chew: 220 (5 min) |
|---|---|---|---|---|
| 1563-062 | 1 | Some marks from the piston of the machine were left on the tablet and the shell was still intact. | The shell broke at the end of the tablet | The tablet became flat |
| | 2(*) | | | |

(*)As this tablet was considered a reference before optimizations only one tablet was tested.

The shell construction of shell 2 having an outer wall thickness of 1.4-1.8 mm is applied. The results are shown below.

| Batch. no. | Tablet no. | No. of chew: 44 (1 min.) | No. of chew: 132 (3 min.) | No. of chew: 220 (5 min) |
|---|---|---|---|---|
| 1044-057 | 1 | No signs of marks from the piston of the machine were left on the tablet | A few marks from the piston of the machine were left on the tablet and the shell was still intact. | A few marks from the piston of the machine were left on the tablet and the shell was still intact. |
| | 2 | No signs of marks from the piston of the machine were left on the tablet | A few marks from the piston of the machine were left on the tablet and the shell was still intact. | Some marks from the piston of the machine were left on the tablet and the shell was still intact. |

The shell construction of shell 402 is applied. The results are shown below.

| Batch. no. | Tablet no. | No. of chew: 44 (1 min.) | No. of chew: 132 (3 min.) | No. of chew: 220 (5 min) |
|---|---|---|---|---|
| 1563-062 | 1 | No signs of marks from the piston of the machine were left on the tablet | Some marks from the piston of the machine were left on the tablet and the shell was still intact. | Some marks from the piston of the machine were left on the tablet and the shell was still intact. |
| | 2 | Subsequent to 17 chew, the chewing machine failed to proceeding chews | NA | NA |

The shell construction of shell 502 is applied. The results are shown below.

| Batch. no. | Tablet no. | No. of chew: 44 (1 min.) | No. of chew: 132 (3 min.) | No. of chew: 220 (5 min) |
|---|---|---|---|---|
| 1563-062 | 1 | No signs of marks from the piston of the machine were left on the tablet | Some marks from the piston of the machine were left on the tablet and the shell was still intact. | Some marks from the piston of the machine were left on the tablet and the shell was still intact. |
| | 2 | No signs of marks from the piston of the machine were left on the tablet | Some marks from the piston of the machine were left on the tablet and the shell was still intact. | Some marks from the piston of the machine were left on the tablet and the shell was still intact. |

The shell construction of shell 702 is applied. The results are shown below.

| Batch. no. | Tablet no. | No. of chew: 44 (1 min.) | No. of chew: 132 (3 min.) | No. of chew: 220 (5 min) |
|---|---|---|---|---|
| 1044-056 | 1 | A few signs of marks from the piston of the machine were left on the tablet | A few signs of marks from the piston of the machine were left on the tablet | A few signs of marks from the piston of the machine were left on the tablet |
| | 2 | Subsequent to 6 chew, the chewing machine failed to proceeding chews | NA | NA |

The shell construction of shell 102 is applied. The results are shown below.

| Batch. no. | Tablet no. | No. of chew: 44 (1 min.) | No. of chew: 132 (3 min.) | No. of chew: 220 (5 min) |
|---|---|---|---|---|
| 1044-058 | 1 | No signs of marks from the piston of the machine were left on the tablet | A few marks from the piston of the machine were left on the tablet and the shell was still intact. | Subsequent to 1 chew, the chewing machine failed to proceeding chews |
| | 2 | Subsequent to 1 chew, the chewing machine failed to proceeding chews | NA | NA |

The shell construction of shell 802 is applied. The results are shown below.

| Batch. no. | Tablet no. | No. of chew: 44 (1 min.) | No. of chew: 132 (3 min.) | No. of chew: 220 (5 min) |
|---|---|---|---|---|
| 1044-059 | 1 | Subsequent to 3 chew, the chewing machine failed to proceeding chews | NA | NA |
| | 2 | Subsequent to 2 chew, the chewing machine failed to proceeding chews | NA | NA |

Besides the tests mentioned above the intact tablets were subjected to physical tampering by use of electronical tool (coffee grinder, Krups GVX242).

The construction applied is shown below with the results.

| Batch. no. | Construction (ref. to shell) | Tablet no. | Results |
|---|---|---|---|
| 1563-062 | Shell 402 | 1 | Only few marks on the shell and equipment failure |
| | | 2 | Only few marks on the shell and equipment failure |
| | | 3 | Only few marks on the shell and equipment failure |
| | Shell 502 | 1 | Only few marks on the shell and equipment failure |
| | | 2 | Only few marks on the shell, and matrix pops out. Equipment failure |
| | | 3 | Only few marks on the shell and equipment failure |
| 1044-057 | Shell 2 (wall thickness 1.4-1.8 mm) | 1 | Only few marks on the shell and equipment failure |
| | | 2 | Only few marks on the shell and equipment failure |
| | | 3 | Only few marks on the shell and equipment failure |
| 1044-058 | Shell 102 | 1 | Only few marks on the shell and equipment failure |
| | | 2 | Only few marks on the shell and equipment failure |
| | | 3 | Only few marks on the shell and equipment failure |
| 1044-059 | Shell 802 | 1 | One small piece is chopped off, no other marks on the shell and equipment failure |
| | | 2 | Only few marks on the shell and equipment failure |
| | | 3 | Only few marks on the shell and equipment failure |

Example 10

Gelling Agents to Prevent Injectability of Pharmaceutical Composition (e.g. Tablets) when Melted or Dissolved The purpose of adding gelling agents to the pharmaceutical composition is to make it more physical deterrent, so that it is impossible to inject melted or dissolved tablets (c.f. protocol on tampering methods).

It was chosen to use Acetaminophen as a model drug substance and add 10% (w/w) of the chosen gelling agent in the pharmaceutical composition, which was prepared as described in Methods above.

To attain a measure of how easy it is to inject the melted or dissolved pharmaceutical composition dependent on which gelling agent that has been chosen. The pharmaceutical composition for example tablet, in which the gelling agent has been incorporated, is melted under a candle. Subsequently 1 mL of the liquid is extracted by a syringe with a diameter of ca. 0.5 mm, after which the liquid pressed out with a pressure/weight of the syringe of approximately 3 kg. The time required to press out the liquid is measured illustrating how difficult it is to inject the pharmaceutical composition.

| Composition | % w/w |
|---|---|
| Acetaminophen | 9.0 |
| PoloXamer 188 | 4.5 |
| PEO 200.000 | 76.5 |
| Gelling agent (c.f. the list below) | 10 |

| Gelling agent | Time for required to inject the solution (s) |
|---|---|
| Eudragit L100-55 | 7.3 |
| Guar Gum 400 | 7.6 |
| HPMC 100 000 | 13.7 |
| Carboxy Methyl Cellulose-Na | 13.5 |
| Gelcarin 379 | 25.4 |
| Gelcarin 812 | 15.1 |
| Gellan Gum 400 | 25-35 |

The results are shown above. As seen from the table Gellan Gum 400 and Gelcarin 379 are by far the most efficient gelling agents, followed by Gelcarin 812, HPMC 100 000 and Carboxy Methyl Cellulose-Na. Eudragit L100-55 and Gua Gum 400 were less suitable gelling agents.

Example 11

Plasticizers to Enforce Physical Properties of the Shell Construction I

Pharmaceutical composition were produced as described in Methods by the means of large scale injection moulding with the purpose of investigating the physical properties of the shell composition comprising PLA with different plasticizer and thereby enforcing physical deterrence. Physical deterrence was tested by subjecting the pharmaceutical composition for example tablets to milling in a Krupps coffee grinder. The method applied is described in the protocol on tampering methods.

| Matrix composition | % w/w: |
|---|---|
| Morphine Sulphate pentahydrate | 36.0 |
| PoloXamer 188 | 12.2 |
| PEO 300.000 | 16.0 |
| PEO 200.000 | 22.7 |
| Mannitol | 3.0 |
| BHT | 0.1 |
| HPMC 100.000 | 5 |
| Carrageenan 379 | 5 |

The applied plasticizers and the content are stated below. The shell composition consists of PLA and one or more plasticizers.

| Batch no. of shell material | PLA (% w/w) | PEG 20 000 (% w/w) | PEO 200 000 (% w/w) | PEO 300 000 (% w/w) | PEO 600 000 (% w/w) |
|---|---|---|---|---|---|
| 1049-090A | 86 | 14 | | | |
| 1049-090B | 86 | | 14 | | |
| 1049-090C | 86 | 7 | 7 | | |
| 1049-090D | 86 | 5 | 9 | | |
| 1049-090E | 80 | 20 | | | |
| 1049-090F | 93 | | 7 | | |
| 1049-090G | 86 | | | 14 | |
| 1049-090H | 86 | | | | 14 |

It was assessed whether or not the matrix composition could be removed from the shell. The results are shown below:

| | Coffee mill Krups - Test 1 | | Coffee mill Krups - 30 sec | |
|---|---|---|---|---|
| Batch No | 1 tablet | 5 tablets | 1 tablet | 5 tablets |
| Shell 2, wall thickness 1.4-1.8 mm/ 1049-090 A | 5 sec, shell crushed | 9 sec, shell crushed | Everything in small pieces | Everything in small pieces |
| Shell 2, wall thickness 1.4-1.8 mm/ 1049-090 A | 3 sec, shell crushed | 11 sec, shell crushed | Shell to powder, matrix small pieces | Shell to powder, matrix small and large pieces |
| Shell 2, wall thickness 1.4-1.8 mm/ 1049-090 B | 3 sec, shell crushed | 7 sec, shell didn't came of | Shell and matrix in small pieces | 1 whole tablet, one tablet missing half a shell, one tablet without shell, 2 tablets in small and large pieces |
| Shell 802/ 1049-090 B | 8 sec, shell came of | 15 sec, two whole tablets, three tablets in pieces | Everything in small pieces | Large pieces of shell, matrix in small pieces |
| Shell 802/ 1049-090 B | 15 sec, shell came of | 15 sec, four whole tablets, one tablet in pieces | Large pieces of shell, matrix in small pieces | Large pieces of shell, matrix in small pieces |
| Shell 2, wall thickness 1.4-1.8 mm/ 1049-090 C | 4 sec, shell came of | 7 sec, three whole tablets and two without shell | Everything in small pieces | Not tested |

| Batch No | Coffee mill Krups - Test 1 | | Coffee mill Krups - 30 sec | |
| --- | --- | --- | --- | --- |
| | 1 tablet | 5 tablets | 1 tablet | 5 tablets |
| Shell 2, wall thickness 1.4-1.8 mm)/ 1049-090 C | 15 sec, half a shell came of | 12 sec, three whole tablets but the mill broke down | Small and large pieces | Large pieces, lid on mill broken |

Example 12

Naltrexone

| Matrix composition (placebo) | % w/w |
| --- | --- |
| PEO 200.000 | 43.7% |
| PEO 300.000 | 31.0% |
| Poloxamer 188 | 12.2% |
| Mannitol | 3.0% |
| HPMC 100.000 | 5.0% |
| Carragenan 379 | 5.0% |
| BHT | 0.1% |

| Shell composition | % w/w |
| --- | --- |
| Polylactid acid | 100% |

Total tablet weight was approximately 925 mg

Polylactic acid was injection moulded in a Haake Minijet (Haake MiniJet II, Thermo Electron, Karlsruhe, Germany) as described in Methods. An inner core filled with approximately 25 mg Naltrexone hydrochloride was prepared and closed in both ends with the above mentioned shell composition. The inner core has a size of 8 mm×4.26 mm×2.49 mm. The inner core was placed in the cavity of a larger shell 2 (H: 20 mm; L: 6 mm; B: 6 mm) with the same shell composition and the large shell was filled with placebo matrix composition as described in Methods.

Dissolution tests of naltrexone were performed in accordance to USP 30, NF 25, (711). Apparatus 2 (paddle method). The dissolution medium consisted of phosphate buffer solution pH 6.8. The volume of the dissolution medium was 500 ml and the rotation speed of the paddles was 50 rpm throughout the dissolution rum. The temperature was 37° C. Samples were withdrawn at suitable time intervals and analysed for content of active drug substance by means of HPLC UV detection. Intact tablets n=2 and tablets milled in a Coffee Grinder, Krups GVX242 (n=2) were analyse in dissolution.

The amount of naltrexone was determined by a modified USP method. The technique was reverse phase chromatography, using a Supelco Ascentis Express C18 2.7 µm 4.6*100 mm column. The mobile phase consisted of 1.08 g sodium 1-octane sulphonate, 23.8 g sodium acetate, 1 ml triethylamine, 450 ml methanol and approximately 550 ml water. The HPLC settings were as follows: Isocratic, column temperature 30° C. flow 0.6 ml/min, detection HPLC-UV at 280 nm, injection volume 20 µl with a 6 minutes run time.

During the milling, described above, some naltrexone was spilled which explains the amount found to be less than the 25 mg (i.e. 100%) that was filled in the small inner core, see the results below.

| Sample | | 0.2 hours | 0.5 hours | 0.8 hours | 1.5 hours | 20 hours | 30 hours |
| --- | --- | --- | --- | --- | --- | --- | --- |
| 1 | Intact | ND | ND | ND | ND | ND | ND |
| 2 | Intact | ND | ND | ND | ND | ND | ND |
| 1 | Ground | 34.1% | 36.3% | 36.6% | 37.4% | 39.0% | 34.9% |
| 2 | Ground | 31.5% | 34.2% | 34.7% | 34.9% | 37.1% | 35.9% |

ND: not detectable

The invention claimed is:

1. An abuse resistant oral pharmaceutical composition, comprising a shell resistant to physical tampering and a matrix composition,
wherein the matrix composition is at least partly contained within the shell and comprises an active drug substance and a polyethylene oxide polymer,
wherein the shell comprises an outer shell wall having an inner surface and an outer surface, the outer surface being a double curved surface, wherein the shell extends from a first end to a second end, the shell having a length in a range of from 4 mm to 20 mm, wherein the outer shell wall has a first opening at the first end and a second opening at the second end, the first opening and the second opening having an area in a range of from about 1 mm$^2$ to about 100 mm$^2$ and wherein the outer shell wall is of varying thickness and has a maximum thickness in a range of from 1.0 mm to about 10 mm, the outer shell wall being impermeable to water.

2. The composition of claim 1, wherein the matrix composition comprises one or more polyethylene oxide polymers having a total average molecular weight of from 200,000 to 300,000.

3. The composition of claim 1, wherein the matrix composition further comprises a plasticizer.

4. The composition of claim 1, wherein the matrix composition further comprises a stabilizer.

5. The composition of claim 1, wherein the matrix composition further comprises a gelling agent.

6. The composition of claim 1, wherein the matrix composition further comprises an antioxidant.

7. The composition of claim 1, wherein the shell comprises polylactic acid.

8. The composition of claim 7, wherein the shell further comprises a polyethylene oxide polymer.

9. The composition of claim 1, wherein the active drug substance is selected from morphine, oxycodone, hydrocodone, hydromorphone, oxymorphone, ketorolac, amphetamine, methylphenidate, diazepam, and pharmaceutically acceptable salts thereof.

10. The composition of claim 1, wherein
the active drug substance comprises one or more of morphine and pharmaceutically acceptable salts thereof;
the matrix composition comprises one or more polyethylene oxide polymers having a total average molecular weight of from 200,000 to 300,000; butylated hydroxytoluene; optionally, a poloxamer; and optionally, mannitol; and the shell comprises polylactic acid and, optionally, a polyethylene oxide polymer.

11. The composition of claim 10, wherein the matrix composition further comprises a stabilizer.

12. The composition of claim 1, wherein
the active drug substance comprises one or more of oxycodone and pharmaceutically acceptable salts thereof;
the matrix composition comprises one or more polyethylene oxide polymers having a total average molecular weight of from 200,000 to 300,000; butylated hydroxytoluene; optionally, a poloxamer; optionally, a methacrylic acid-methyl methacrylate (Eudragit®) copolymer; and, optionally, hydroxypropylmethylcellulose; and
the shell comprises polylactic acid and, optionally, a polyethylene oxide polymer.

13. The composition of claim 12, wherein the matrix composition further comprises a stabilizer.

14. The composition of claim 1, wherein
the active drug substance comprises one or more of hydrocodone and pharmaceutically acceptable salts thereof;
the matrix composition comprises one or more polyethylene oxide polymers having a total average molecular weight of from 200,000 to 300,000; butylated hydroxytoluene; optionally, a poloxamer; and, optionally, hydroxypropylmethylcellulose; and
the shell comprises polylactic acid and, optionally, a polyethylene oxide polymer.

15. The composition of claim 14, wherein the matrix composition further comprises a stabilizer.

16. The composition of claim 1, wherein
the active drug substance comprises one or more of hydromorphone and pharmaceutically acceptable salts thereof;
the matrix composition comprises one or more polyethylene oxide polymers having a total average molecular weight of from 200,000 to 300,000; butylated hydroxytoluene; optionally, a poloxamer; and, optionally, hydroxypropylmethylcellulose; and
the shell comprises polylactic acid and, optionally, a polyethylene oxide polymer.

17. The composition of claim 16, wherein the matrix composition further comprises a stabilizer.

18. The composition of claim 1, wherein
the active drug substance comprises one or more of oxymorphone and pharmaceutically acceptable salts thereof;
the matrix composition comprises one or more polyethylene oxide polymers having a total average molecular weight of from 200,000 to 300,000; butylated hydroxytoluene; optionally, a poloxamer; and, optionally, hydroxypropylmethylcellulose; and
the shell comprises polylactic acid and, optionally, a polyethylene oxide polymer.

19. The composition of claim 18, wherein the matrix composition further comprises a stabilizer.

20. The composition of claim 1, wherein
the active drug substance comprises one or more of ketorolac and pharmaceutically acceptable salts thereof;
the matrix composition comprises one or more polyethylene oxide polymers having a total average molecular weight of from 200,000 to 300,000; butylated hydroxytoluene; optionally, a poloxamer; and, optionally, hydroxypropylmethylcellulose; and
the shell comprises polylactic acid and, optionally, a polyethylene oxide polymer.

21. The composition of claim 20, wherein the matrix composition further comprises a stabilizer.

22. The composition of claim 1, wherein
the active drug substance comprises one or more of amphetamine and pharmaceutically acceptable salts thereof;
the matrix composition comprises one or more polyethylene oxide polymers having a total average molecular weight of from 200,000 to 300,000; butylated hydroxytoluene; optionally, a poloxamer; and, optionally, hydroxypropylmethylcellulose; and
the shell comprises polylactic acid and, optionally, a polyethylene oxide polymer.

23. The composition of claim 22, wherein the matrix composition further comprises a stabilizer.

24. The composition of claim 1, wherein
the active drug substance comprises one or more of methylphenidate and pharmaceutically acceptable salts thereof;
the matrix composition comprises one or more polyethylene oxide polymers having a total average molecular weight of from 200,000 to 300,000; butylated hydroxytoluene; optionally, a poloxamer; and, optionally, hydroxypropylmethylcellulose; and
the shell comprises polylactic acid and, optionally, a polyethylene oxide polymer.

25. The composition of claim 24, wherein the matrix composition further comprises a stabilizer.

26. The composition of claim 1, wherein
the active drug substance comprises one or more of diazepam and pharmaceutically acceptable salts thereof;
the matrix composition comprises one or more polyethylene oxide polymers having a total average molecular weight of from 200,000 to 300,000; butylated hydroxytoluene; optionally, a poloxamer; and, optionally, hydroxypropylmethylcellulose; and
the shell comprises polylactic acid and, optionally, a polyethylene oxide polymer.

27. The composition of claim 26, wherein the matrix composition further comprises a stabilizer.

* * * * *